United States Patent
Eagon et al.

(10) Patent No.: US 11,578,071 B2
(45) Date of Patent: Feb. 14, 2023

(54) PREPARATION OF PYRAZOLO[3,4-B]PYRIDINES AS ANTIMALARIALS

(71) Applicant: University of Kentucky Research Foundation, Lexington, KY (US)

(72) Inventors: Scott Charles Eagon, San Luis Obispo, CA (US); Rodney Kiplin Guy, Lexington, KY (US); Jared T. Hammill, Lexington, KY (US)

(73) Assignees: University of Kentucky Research Foundation, Lexington, KY (US); Cal Poly Corporation, San Luis Obispo, CA (US)

(*) Notice: Subject to any disclaimer, the term of this patent is extended or adjusted under 35 U.S.C. 154(b) by 177 days.

(21) Appl. No.: 17/063,498

(22) Filed: Oct. 5, 2020

(65) Prior Publication Data

US 2021/0101901 A1    Apr. 8, 2021

Related U.S. Application Data

(60) Provisional application No. 62/910,882, filed on Oct. 4, 2019.

(51) Int. Cl.
*C07D 471/04* (2006.01)
*C07D 231/56* (2006.01)

(52) U.S. Cl.
CPC ......... *C07D 471/04* (2013.01); *C07D 231/56* (2013.01)

(58) Field of Classification Search
CPC ............................. C07D 471/04; C07D 231/56
See application file for complete search history.

(56) References Cited

U.S. PATENT DOCUMENTS

2009/0286983 A1   11/2009   Almansa Rosales et al.
2017/0121324 A1    5/2017   Ford et al.

FOREIGN PATENT DOCUMENTS

WO    WO2016/210034 A1    12/2016

OTHER PUBLICATIONS

Capper, et al., "Antimalarial 4(1H)-Pyridones Bind to the Qi Site of Cytochrome bc1." Proc. Natl. Acad. Sci. U.S.A., 2015, 112, 755-760.
Zhang, et al., Lead Optimization of 3-Carboxyl-4(1H)-Quinolones to Deliver Orally Bioavailable Antimalarials, J. Med. Chem. 2012, 55, 4205-4219.
Neelarapu, et al., Design and Synthesis of Orally Bioavailable Piperazine Substituted 4(1H)-Quinolones with Potent Antimalarial Activity: Structure-Activity and Structure-Property Relationship Studies, J. Med. Chem. 2018, 61, 1450-1473.
Pubchem-CID: 134139139 Create Date: Jun. 6, 2018 (Jun. 6, 2018) pp. 1-9.

*Primary Examiner* — Shawquia Jackson
(74) *Attorney, Agent, or Firm* — Stites & Harbison PLLC; Mandy Wilson Decker

(57) ABSTRACT

The present invention relates to pyrazolo[3,4-b]pyridine compounds. The present invention further relates to methods for inhibiting *Plasmodium* comprising contacting *Plasmodium* with pyrazolo[3,4-b]pyridine compounds described herein. Also described herein are methods of treating malaria comprising administering pyrazolo[3,4-b]pyridine compounds to a subject in need thereof.

15 Claims, 5 Drawing Sheets

PREPARATION OF PYRAZOLO[3,4-B]PYRIDINES AS ANTIMALARIALS

RELATED APPLICATIONS

This application claims priority from U.S. Provisional Patent Application No. 62/910,882 filed on Oct. 4, 2019 the entire disclosure of which is incorporated herein by this reference.

TECHNICAL FIELD

The present invention relates to pyrazolo[3,4-b]pyridines as anti-malarial compounds and methods using the same.

BACKGROUND

Malaria continues to remain one of the most deadly infectious diseases on the planet. The WHO reported more than 200 million cases 2017 with nearly 435,000 associated deaths, primarily in young children and pregnant women. Despite concerted efforts to combat the spread of Malaria, it continues to have a devastating effect in parts of Asia and Africa. The latest WHO summary, in fact, notes that "no significant progress in reducing global malaria cases was made" from 2015-2017.

Malaria in humans is caused by hematoprotozoan parasites of the genus *Plasmodium*, with *P. falciparum* accounting for the vast majority of fatalities. The *Plasmodium* parasite has a complex life cycle that includes both a liver and erythrocytic stage, significantly increasing the challenge associated with combating infection. While a number of efforts have been made to combat the disease via vaccines and vector control, small-molecule therapeutics remain a critical component of combating malaria. The WHO currently recommends artemisinin-based combination therapy (ACT) to treat complicated forms of infection, but recent reports of emerging resistance against ACTs and a limited number of validated drug targets highlight the need for new treatment options.

SUMMARY

In accordance with the purpose(s) of the invention, as embodied and broadly described herein, the invention, in one aspect, relates to compounds useful as inhibitors of the growth of *Plasmodium*, methods of making same, pharmaceutical compositions comprising same, and methods of treating disorders associated with *Plasmodium*, for example Malaria, using same. Further disclosed are methods and pharmaceutical compositions useful for treating a disease related to *Plasmodium*.

In one aspect, the disclosed compounds can inhibit growth of *Plasmodium*.

Disclosed are methods for the treatment of malaria or other disease associated with *Plasmodium* infection of a subject comprising the step of administering to the subject at least one compound in a dosage and amount effective to treat the disease in the mammal, the compound having a structure represented the following formula:

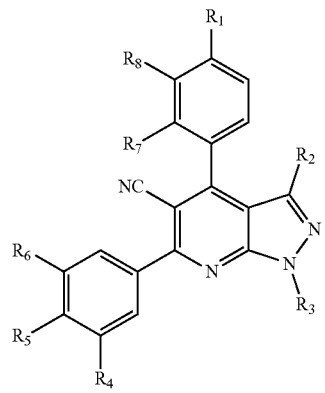

R1 is H, or OH;
R2 is alkyl, aryl, or cycloalkyl;
R3 is substituted or unsubstituted phenyl;
R4 is H, alkyl, or alkoxy;
R5 is H, alkoxy, branched or unbranched alkyl, haloalkyl, halo, cyano, nitro, alkylsulfonyl, or heterocycloalkyl;
R6 is alkyl or may optionally form a 5 or 6 membered heterocyclic ring with R5;
R7 is H, OH, haloalkoxy, nitro, cyano, halo, alkyl, alkylsulfonyl, carboxyl, haloalkyl, alkoxy, ester, or alkynyl; and
R8 is H, or OH;
or a pharmaceutically acceptable salt thereof or a pharmaceutically acceptable derivative thereof.

Also disclosed are methods for inhibiting the growth of *Plasmodium* comprising the step of administering to a subject infected with *Plasmodium* at least one compound at least one compound having a structure represented by the following formula:

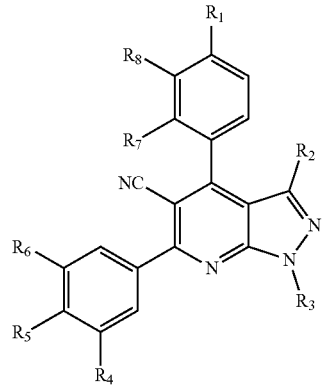

R1 is H, or OH;
R2 is alkyl, aryl, or cycloalkyl;
R3 is substituted or unsubstituted phenyl;
R4 is H, alkyl, or alkoxy;
R5 is H, alkoxy, branched or unbranched alkyl, haloalkyl, halo, cyano, nitro, alkylsulfonyl, or heterocycloalkyl;
R6 is alkyl or may optionally form a 5 or 6 membered heterocyclic ring with R5;
R7 is H, OH, haloalkoxy, nitro, cyano, halo, alkyl, alkylsulfonyl, carboxyl, haloalkyl, alkoxy, ester, or alkynyl; and
R8 is H, or OH;

or a pharmaceutically acceptable salt thereof or a pharmaceutically acceptable derivative thereof.

Also disclosed pharmaceutical compositions comprising a compound having a structure represented by the following formula:

R1 is H, or OH;
R2 is alkyl, aryl, or cycloalkyl;
R3 is substituted or unsubstituted phenyl;
R4 is H, alkyl, or alkoxy;
R5 is H, alkoxy, branched or unbranched alkyl, haloalkyl, halo, cyano, nitro, alkylsulfonyl, or heterocycloalkyl;
R6 is alkyl or may optionally form a 5 or 6 membered heterocyclic ring with R5;
R7 is H, OH, haloalkoxy, nitro, cyano, halo, alkyl, alkylsulfonyl, carboxyl, haloalkyl, alkoxy, ester, or alkynyl; and
R8 is H, or OH;

or a pharmaceutically acceptable salt thereof or a pharmaceutically acceptable derivative thereof.

Also disclosed are methods for making a compound comprising the steps of providing an amine compound having a structure represented by the following formula:

as shown in the Examples below, wherein the variables are defined herein.

Also disclosed are methods for the manufacture of a medicament for inhibiting the growth of *Plasmodium* in a subject comprising combining a compound having a structure represented by the following formula:

R1 is H, or OH;
R2 is alkyl, aryl, or cycloalkyl;
R3 is substituted or unsubstituted phenyl;
R4 is H, alkyl, or alkoxy;
R5 is H, alkoxy, branched or unbranched alkyl, haloalkyl, halo, cyano, nitro, alkylsulfonyl, or heterocycloalkyl;
R6 is alkyl or may optionally form a 5 or 6 membered heterocyclic ring with R5;
R7 is H, OH, haloalkoxy, nitro, cyano, halo, alkyl, alkylsulfonyl, carboxyl, haloalkyl, alkoxy, ester, or alkynyl; and
R8 is H, or OH;

or a pharmaceutically acceptable salt thereof or a pharmaceutically acceptable derivative thereof, with artemisinin-based combination therapy (ACT).

Also disclosed are the products of the disclosed methods for the manufacture of a medicament represented by the following formula:

R1 is H, or OH;
R2 is alkyl, aryl, or cycloalkyl;
R3 is substituted or unsubstituted phenyl;
R4 is H, alkyl, or alkoxy;
R5 is H, alkoxy, branched or unbranched alkyl, haloalkyl, halo, cyano, nitro, alkylsulfonyl, or heterocycloalkyl;
R6 is alkyl or may optionally form a 5 or 6 membered heterocyclic ring with R5;
R7 is H, OH, haloalkoxy, nitro, cyano, halo, alkyl, alkylsulfonyl, carboxyl, haloalkyl, alkoxy, ester, or alkynyl; and
R8 is H, or OH.

Also disclosed are kits comprising a compound having a structure represented by the following formula:

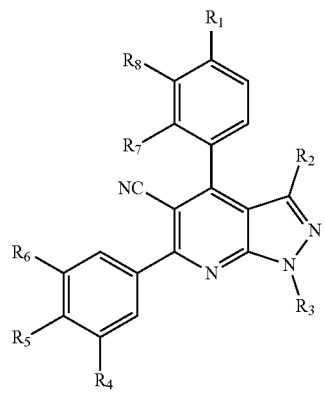

R1 is H, or OH;
R2 is alkyl, aryl, or cycloalkyl;
R3 is substituted or unsubstituted phenyl;
R4 is H, alkyl, or alkoxy;
R5 is H, alkoxy, branched or unbranched alkyl, haloalkyl, halo, cyano, nitro, alkylsulfonyl, or heterocycloalkyl;
R6 is alkyl or may optionally form a 5 or 6 membered heterocyclic ring with R5;
R7 is H, OH, haloalkoxy, nitro, cyano, halo, alkyl, alkylsulfonyl, carboxyl, haloalkyl, alkoxy, ester, or alkynyl; and
R8 is H, or OH;
 or a pharmaceutically acceptable salt thereof or a pharmaceutically acceptable derivative thereof.

Also disclosed are compounds which inhibit the growth of *Plasmodium* having the formula:

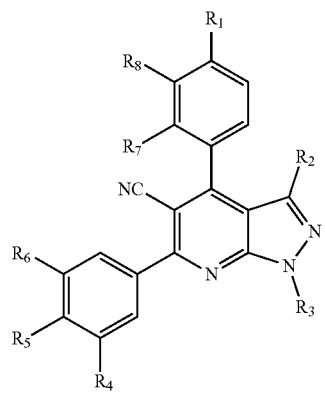

R1 is H, or OH;
R2 is alkyl, aryl, or cycloalkyl;
R3 is substituted or unsubstituted phenyl;
R4 is H, alkyl, or alkoxy;
R5 is H, alkoxy, branched or unbranched alkyl, haloalkyl, halo, cyano, nitro, alkylsulfonyl, or heterocycloalkyl;
R6 is alkyl or may optionally form a 5 or 6 membered heterocyclic ring with R5;
R7 is H, OH, haloalkoxy, nitro, cyano, halo, alkyl, alkylsulfonyl, carboxyl, haloalkyl, alkoxy, ester, or alkynyl; and
R8 is H, or OH.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein.

Figure 1:
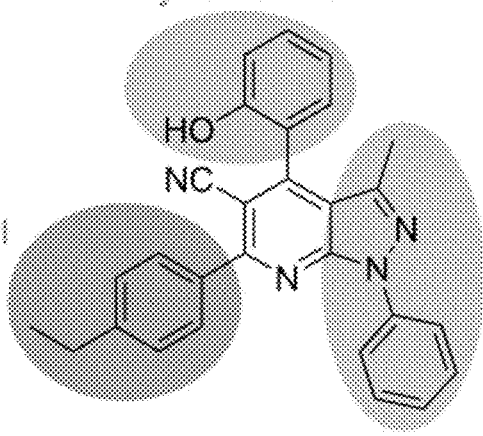
FIG. 1 shows the outline of chemical modifications to probe the structure activity relationships of compounds of the present invention.
Figure 2:
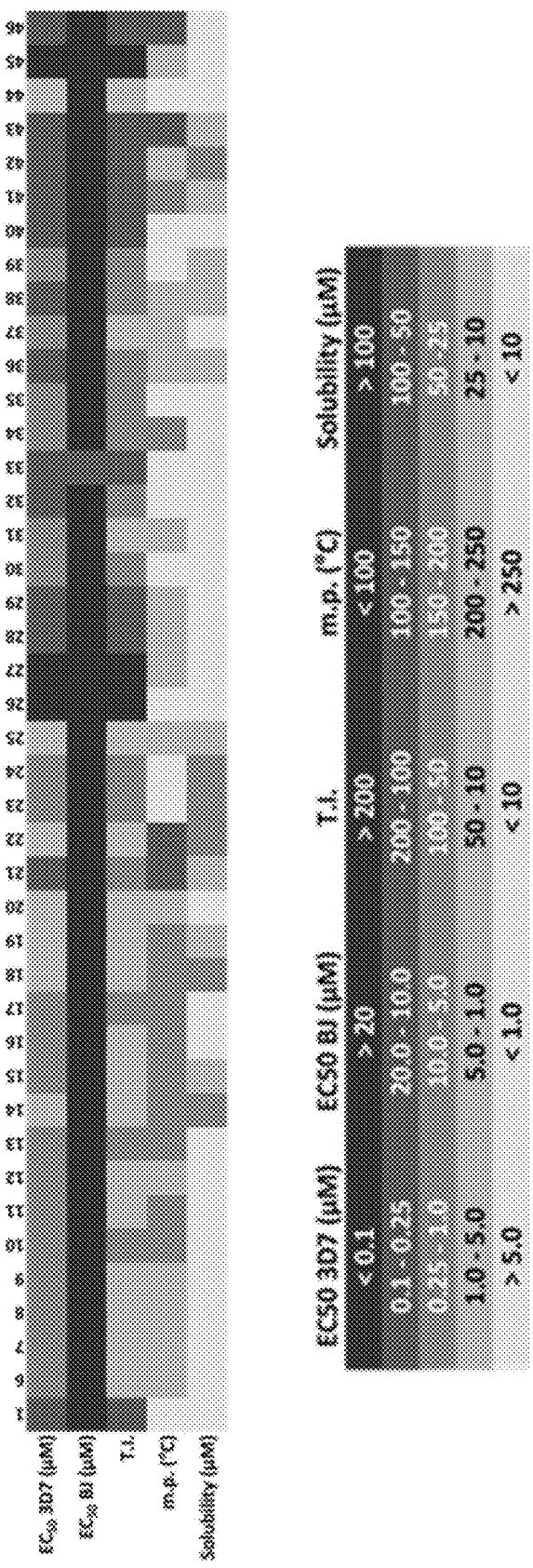
FIG. 2 shows the activity and physiochemical properties of tested compounds.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a biomarker" includes a plurality of such biomarkers, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, width, length, height, concentration or percentage is meant to encompass variations of in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the term "subject" refers to a target of administration. The subject of the herein disclosed methods can be a mammal. Thus, the subject of the herein disclosed methods can include a mouse or human. The term does not denote a particular age or sex.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level if or any particular patient will depend upon a variety of factors including the disorder being treated and the severity of the disorder; the specific composition employed; the age, bodyweight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

In some aspects of the disclosed methods, the subject has been diagnosed with a need for treatment of a disease state associated with *Plasmodium* infection. In some aspects, the disclosed methods can further comprise a step of identifying a subject having a need for treatment of a disclosed disorder.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by inhibiting the growth of *Plasmodium*" means having been subjected to a physical examination by a person of skill, for example, a physician, and found to have a condition that can be diagnosed or treated by a compound or composition that can favorably inhibit the growth of *Plasmodium*. Such a diagnosis can be in reference to a disorder, such as Malaria, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to *Plasmodium* infection) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic.

The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by a formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by a formula —C(O)OH.

The term "ester" as used herein is represented by a formula —OC(O)$A^1$ or C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by a formula -($A^1$O(O)C-$A^2$-C(O)O)$_a$— or -($A^1$O(O)C-$A^2$-OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by a formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by a formula -($A^1$O-$A^2$O)$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by a formula —OH.

The term "ketone" as used herein is represented by a formula -$A^1$C(O)$A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by a formula —$N_3$.

The term "nitro" as used herein is represented by a formula —$NO_2$.

The term "nitrile" as used herein is represented by a formula —CN.

The term "silyl" as used herein is represented by a formula —SiA$^1$A$^2$A$^3$, where A$^1$, A$^2$, and A$^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by a formulas —S(O)A$^1$, —S(O)$_2$A$^1$, —OS(O)$_2$A$^1$, or —OS(O)$_2$OA$^1$, where A$^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by a formula —S(O)$_2$A$^1$, where A$^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by a formula A$^1$S(O)$_2$A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by a formula A$^1$S(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by a formula —SH.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers. Additionally, unless expressly described as "unsubstituted", all substituents can be substituted or unsubstituted.

In some aspects, a structure of a compound can be represented by a formula:

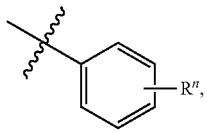

which is understood to be equivalent to a formula:

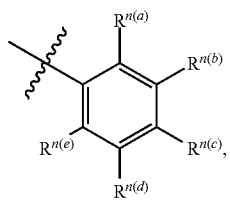

wherein n is typically an integer. That is, R$^n$ is understood to represent five independent substituents, R$^{n(a)}$, R$^{n(b)}$, R$^{n(c)}$, R$^{n(d)}$, R$^{n(e)}$. By "independent substituents," it is meant that each R substituent can be independently defined. For example, if in one instance R$^{n(a)}$ is halogen, then R$^{n(b)}$ is not necessarily halogen in that instance. Likewise, when a group R is defined as four substituents, R is understood to represent four independent substituents, R$^a$, R$^b$, R$^c$, and R$^d$. Unless indicated to the contrary, the substituents are not limited to any particular order or arrangement.

The following abbreviations are used herein. DMF: dimethyl formamide. DMSO: dimethylsulfoxide. DCM: Dichloromethane. MeOH: methanol. CDCl$_3$: Deuterated Chloroform. min: minute(s). h: hour(s). EtOAc: ethyl acetate. EtOH: ethoanol.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Compounds

In one aspect, the invention relates to compounds, or pharmaceutically acceptable derivatives thereof, useful inhibitors of the growth of *Plasmodium falciparum*. In general, it is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using. It is also understood that the disclosed compounds can all be employed as corresponding pharmaceutical compositions.

In one aspect, the invention relates to compounds having a structure represented by the following formula:

$R_1$-$R_5$ is H, hydroxyl, halo, haloalkyl, alkoxy haloalkoxy, carboxyl, alkoxycarbonyl, lower alkyl, sulfonyl, alkylsulfonyl, amino, imino, nitro, cyano, or alkynyl;
$R_6$-$R_7$ is alkyl, unsubstituted or substituted cycloalkyl, substituted or unsubstituted aryl, or substituted or unsubstituted heteroaryl;
$R_8$-$R_{12}$ is H, OH, alkyl, alkoxy, halo, haloalkyl, alkoxy, branched or unbranched alkyl, haloalkyl, halo, cyano, nitro, sulfonyl, alkylsulfonyl, or heterocycloalkyl;
$R_{13}$ is cyano, nitro, imino, or alkynyl; and wherein $R_{10}$ may optionally form a 5 or 6 membered substituted or unsubstituted ring with $R_{11}$ or $R_{10}$ may optionally form a 5 or 6 membered substituted or unsubstituted heterocycle with $R_{11}$.

Also disclosed are compounds of the following formula:

$R_1$-$R_5$ is H, hydroxyl, halo, haloalkyl, alkoxy haloalkoxy, carboxyl, alkoxycarbonyl, lower alkyl, sulfonyl, alkylsulfonyl, amino, imino, nitro, cyano, or alkynyl;
$R_6$-$R_7$ is alkyl, unsubstituted or substituted cycloalkyl, substituted or unsubstituted aryl, or substituted or unsubstituted heteroaryl;
$R_8$-$R_{12}$ is H, OH, alkyl, alkoxy, halo, haloalkyl, alkoxy, branched or unbranched alkyl, haloalkyl, halo, cyano, nitro, sulfonyl, alkylsulfonyl, or heterocycloalkyl; and
wherein $R_{10}$ may optionally form a 5 or 6 membered substituted or unsubstituted ring with $R_{11}$ or $R_{10}$ may optionally form a 5 or 6 membered substituted or unsubstituted heterocycle with $R_{11}$.

Also disclosed are compounds of the following formula:

$R_1$-$R_5$ is H, hydroxyl, halo, haloalkyl, alkoxy haloalkoxy, carboxyl, alkoxycarbonyl, lower alkyl, sulfonyl, alkylsulfonyl, amino, imino, nitro, cyano, or alkynyl;
$R_6$ is methyl;
$R_7$ is phenyl;
$R_8$-$R_9$ is H;
$R_{10}$ is lower alkyl; and
$R_{11}$-$R_{12}$ is H.

Also disclosed are compounds of the following formulas:
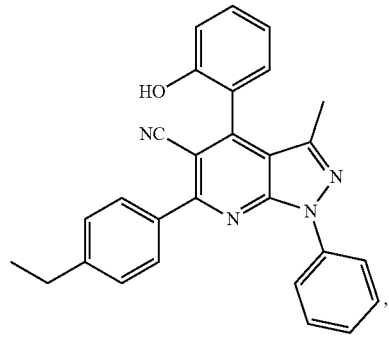
,
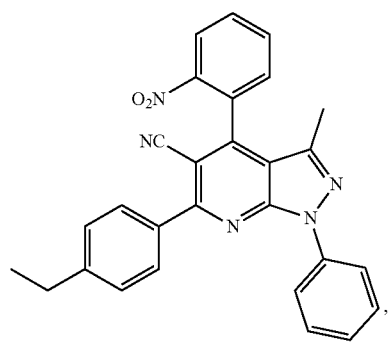
,
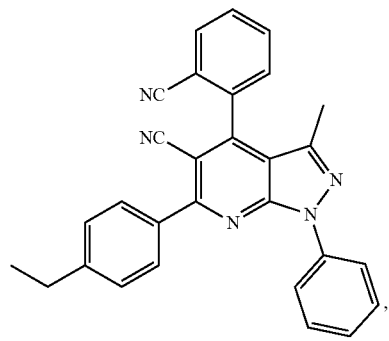
,
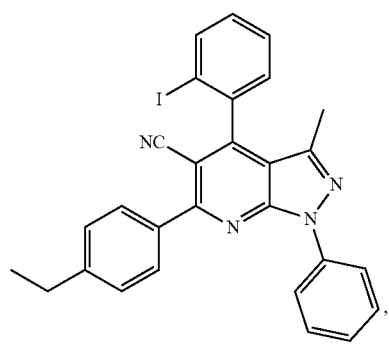
,
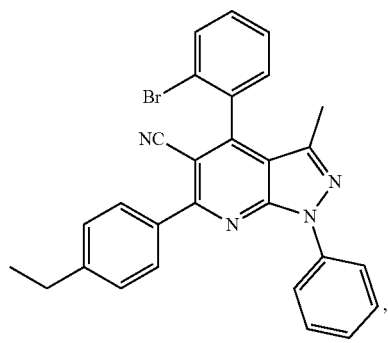
,
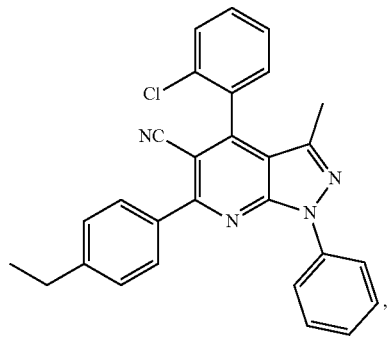
,
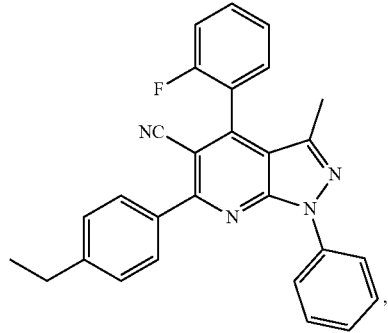
,
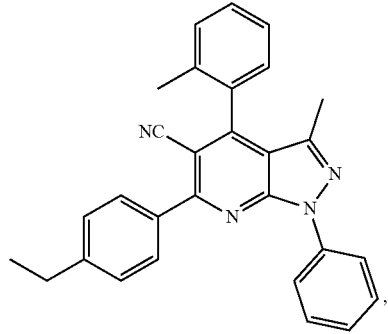
,
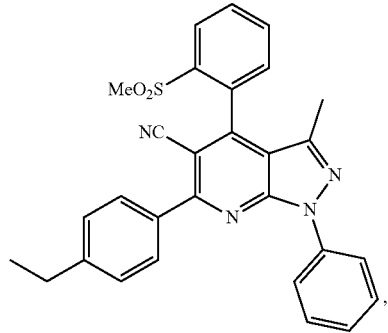
,

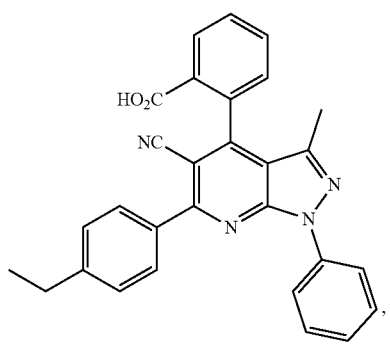
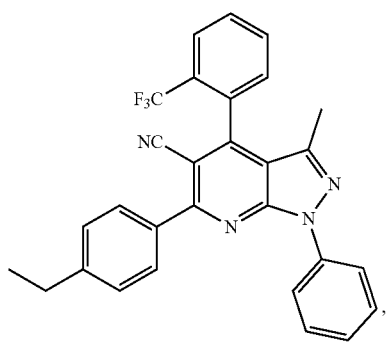
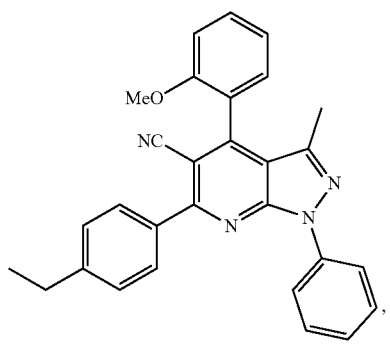
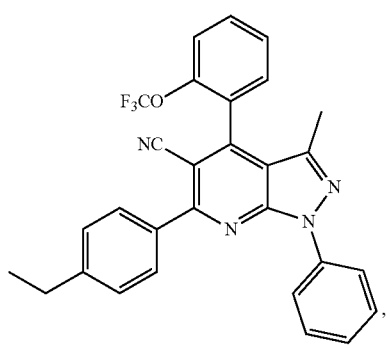
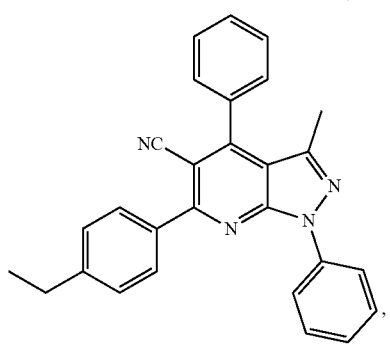
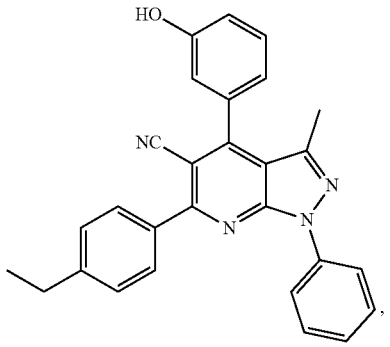
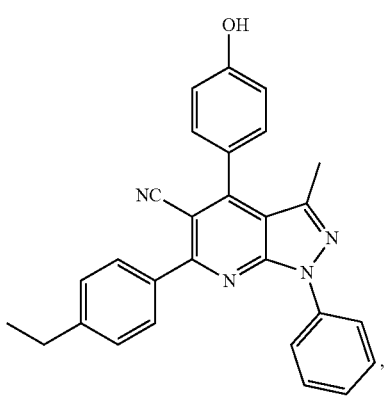
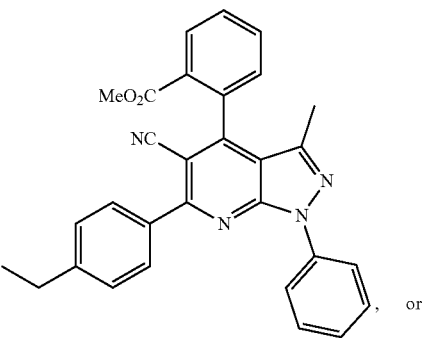
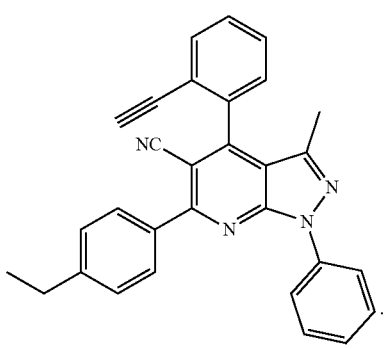

Also disclosed are compounds of the following formula:

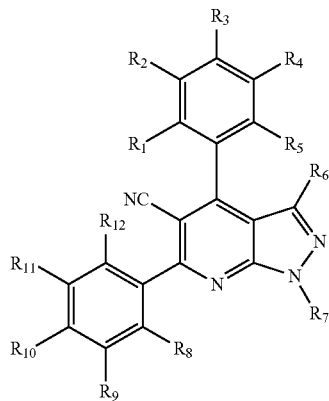

R$_1$ is OH;

R$_2$-R$_5$ is H;

R$_6$ is lower alkyl;

R$_7$ is phenyl;

R$_8$-R$_{12}$ is H, OH, alkyl, alkoxy, halo, haloalkyl, alkoxy, branched or unbranched alkyl, haloalkyl, halo, cyano, nitro, sulfonyl, alkylsulfonyl, or heterocycloalkyl; and Wherein R$_{10}$ may optionally form a 5 or 6 membered substituted or unsubstituted ring with R$_{11}$ or R$_{10}$ may optionally form a 5 or 6 membered substituted or unsubstituted heterocycle with R$_{11}$.

Also disclosed are compounds of the following formulas:

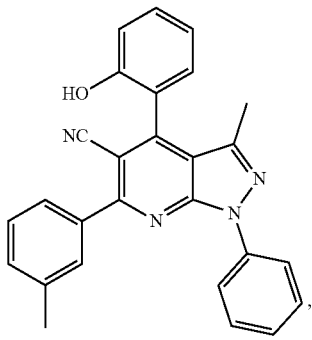

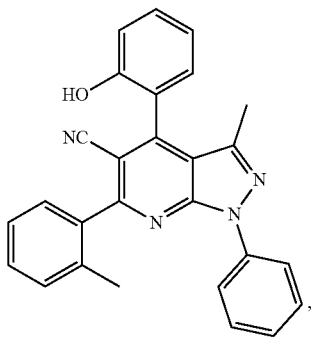

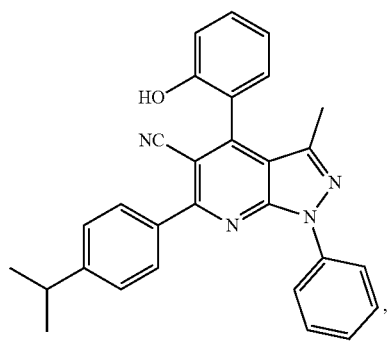

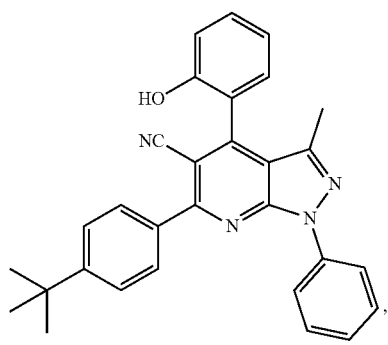

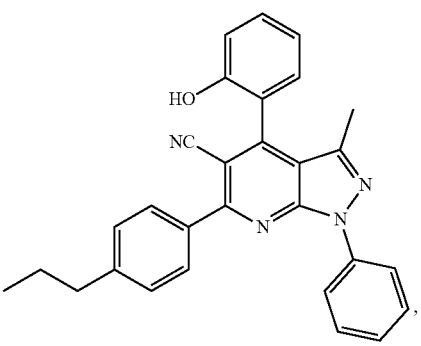

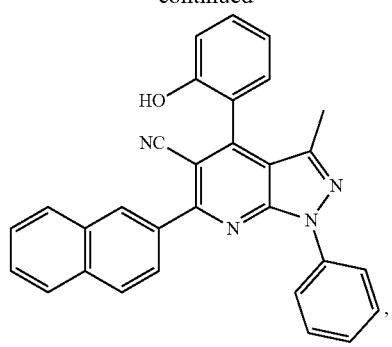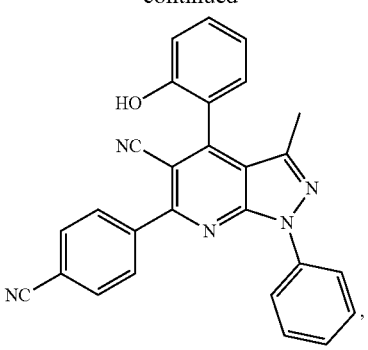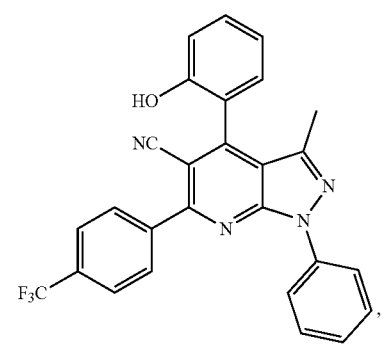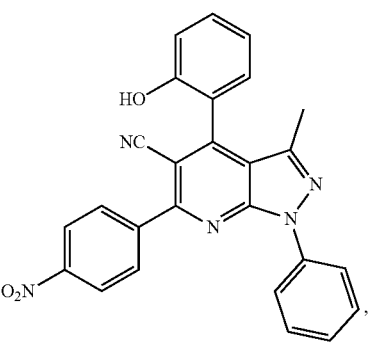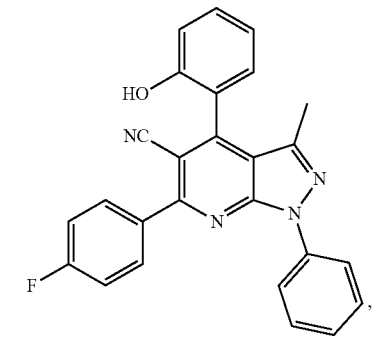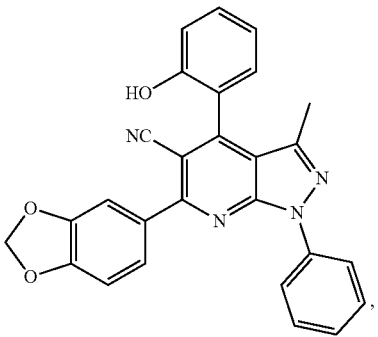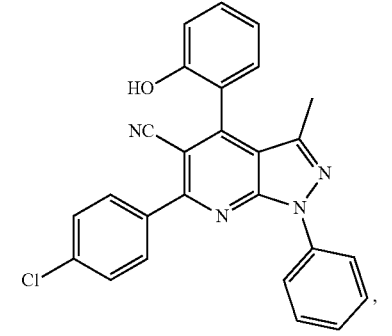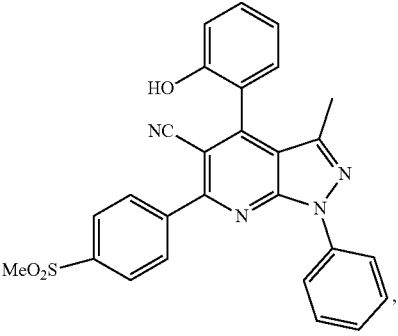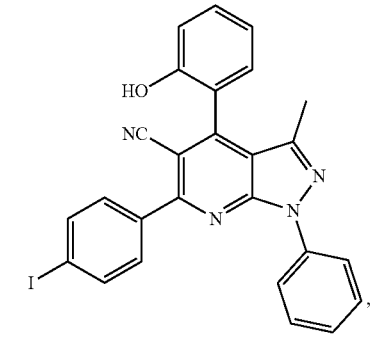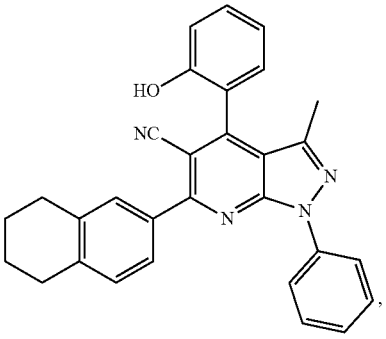

-continued
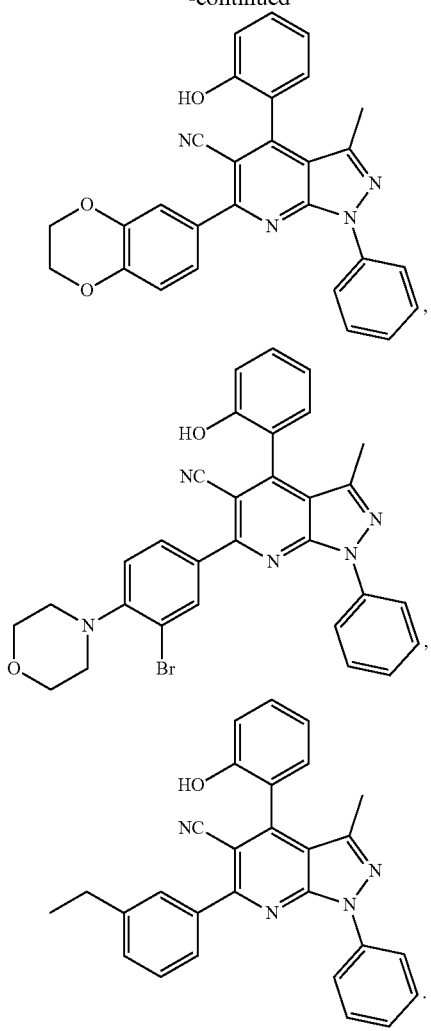
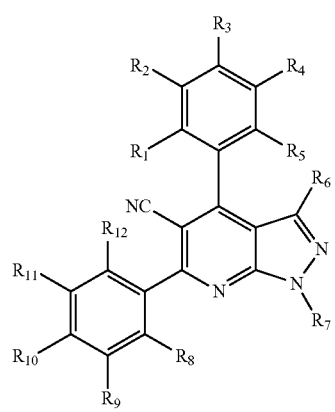
Also disclosed are compounds of the following formula:
R₁ is OH;
R₂-R₅ is H;
R₆-R₇ is alkyl, unsubstituted or substituted cycloalkyl, substituted or unsubstituted aryl, or substituted or unsubstituted heteroaryl;
R₈-R₉ is H;
R₁₀ is lower alkyl; and
R₁₁-R₁₂ is H.
Also disclosed are compounds of the following formula:
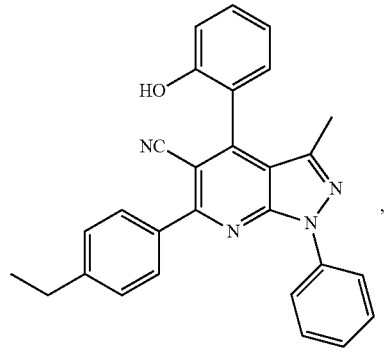
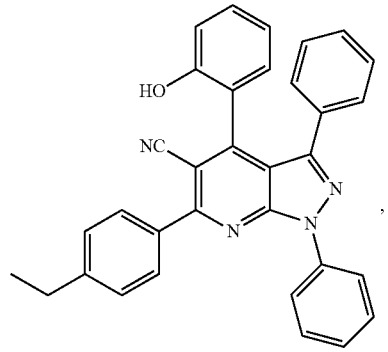
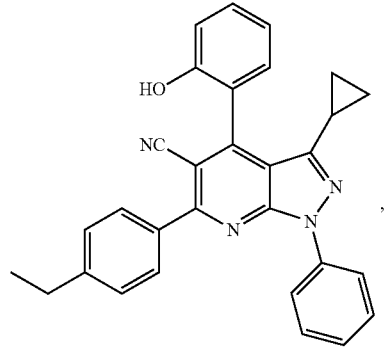
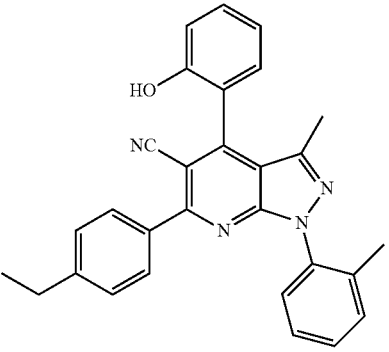

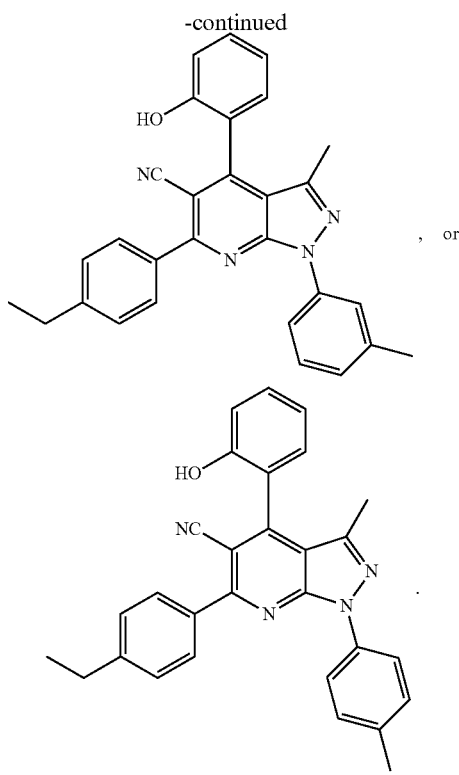

, or

Also disclosed herein is a pharmaceutical composition comprising a compound of the following formula:

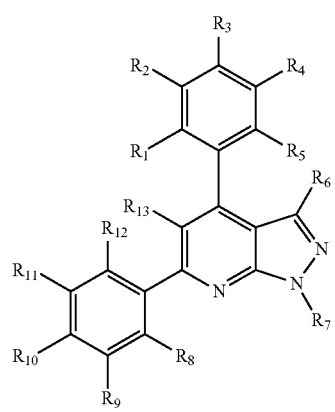

$R_1$-$R_5$ is H, hydroxyl, halo, haloalkyl, alkoxy haloalkoxy, carboxyl, alkoxycarbonyl, lower alkyl, sulfonyl, alkylsulfonyl, amino, imino, nitro, cyano, or alkynyl;
$R_6$-$R_7$ is alkyl, unsubstituted or substituted cycloalkyl, substituted or unsubstituted aryl, or substituted or unsubstituted heteroaryl;
$R_8$-$R_{12}$ is H, OH, alkyl, alkoxy, halo, haloalkyl, alkoxy, branched or unbranched alkyl, haloalkyl, halo, cyano, nitro, sulfonyl, alkylsulfonyl, or heterocycloalkyl;
$R_{13}$ is cyano, nitro, imino, or alkynyl;
Wherein $R_{10}$ may optionally form a 5 or 6 membered substituted or unsubstituted ring with R11 or $R_{10}$ may optionally form a 5 or 6 membered substituted or unsubstituted heterocycle with $R_{11}$; and a pharmaceutically acceptable carrier.

The compounds disclosed herein can include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

The analogs (compounds) of the present disclosure are arranged into several categories to assist the formulator in applying a rational synthetic strategy for the preparation of analogs which are not expressly exampled herein. The arrangement into categories does not imply increased or decreased efficacy for any of the compositions of matter described herein.

Uses

In one aspect the present invention also relates to a method for inhibiting the growth of *Plasmodium* comprising administering to cells infected with *Plasmodium* a compound of the following formula:

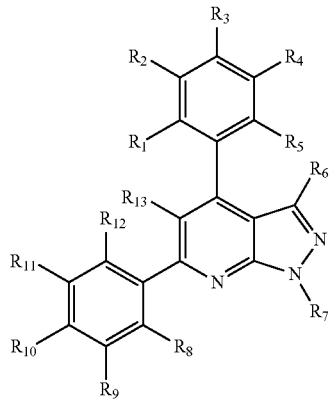

$R_1$-$R_5$ is H, hydroxyl, halo, haloalkyl, alkoxy haloalkoxy, carboxyl, alkoxycarbonyl, lower alkyl, sulfonyl, alkylsulfonyl, amino, imino, nitro, cyano, or alkynyl;
$R_6$-$R_7$ is alkyl, unsubstituted or substituted cycloalkyl, substituted or unsubstituted aryl, or substituted or unsubstituted heteroaryl;
$R_8$-$R_{12}$ is H, OH, alkyl, alkoxy, halo, haloalkyl, alkoxy, branched or unbranched alkyl, haloalkyl, halo, cyano, nitro, sulfonyl, alkylsulfonyl, or heterocycloalkyl;
$R_{13}$ is cyano, nitro, imino, or alkynyl; and
wherein $R_{10}$ may optionally form a 5 or 6 membered substituted or unsubstituted ring with $R_{11}$ or $R_{10}$ may optionally form a 5 or 6 membered substituted or unsubstituted heterocycle with $R_{11}$.

In some embodiments, the invention is further directed towards a method disclosed herein wherein the *Plasmodium* is *Plasmodium falciparum*. In other embodiments, the *Plasmodium* described herein is drug resistant. In some embodiments, *Plasmodium* is resistant to atovaquone. In further embodiments, the cells are in a subject. In some embodiments, the subject is a human.

Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

An amount suitable for inhibiting the growth of *Plasmodium* will generally be about 1 nM to about 100 µM.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed compounds and a pharmaceutically acceptable carrier.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

In such combinations the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be coadministered, either in concomitant therapy or in a fixed combination.

In one aspect, the compound can be employed in combination with anti-Malarial agents, quinine and related agents, chloroquine, amodiaquine, pyrimethamine, proguanil, sulfonamides, mefloquine, atocaquone, primaquine, artemisinin and derivates, halofantrine, doxyclycline, clindamycin, and salts thereof, and combinations thereof, and the like.

In one aspect, the invention relates to a pharmaceutical composition comprising a compound disclosed herein or a pharmaceutically acceptable salt thereof or a pharmaceutically acceptable derivative thereof; and a pharmaceutically acceptable carrier.

In one aspect, the invention relates to pharmaceutical compositions comprising a compound having a structure represented by a compound of the following formula:

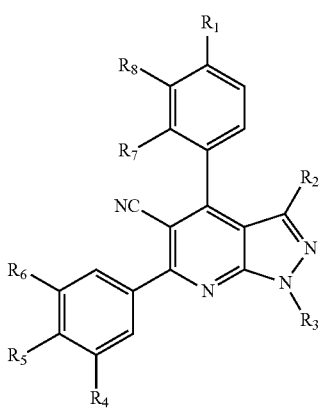

R1 is H, or OH;
R2 is alkyl, aryl, or cycloalkyl;
R3 is substituted or unsubstituted phenyl;
R4 is H, alkyl, or alkoxy;
R5 is H, alkoxy, branched or unbranched alkyl, haloalkyl, halo, cyano, nitro, alkylsulfonyl, or heterocycloalkyl;
R6 is alkyl or may optionally form a 5 or 6 membered heterocyclic ring with R5;
R7 is H, OH, haloalkoxy, nitro, cyano, halo, alkyl, alkylsulfonyl, carboxyl, haloalkyl, alkoxy, ester, or alkynyl; and
R8 is H, or OH;
 or a pharmaceutically acceptable salt thereof or a pharmaceutically acceptable derivative thereof; and a pharmaceutically acceptable carrier.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

$^1$H and $^{13}$C Nuclear Magnetic Resonance (NMR) spectra were obtained on a 300 or 400 MHz instrument using CDCl$_3$, DMSO-d$_6$ or acetone-d$_6$ as the solvent. Chemical shifts were reported as δ values in parts per million (ppm) relative to the solvent. All reactions were performed open to the atmosphere unless indicated otherwise. Analytical thin layer chromatography (TLC) was performed on aluminum-backed 250 μm layer silica plates visualized with either 254 or 365 nm wavelengths. Sonication was performed in an Ultrasonic Cleaner GB928. All solvents were used without purification and no attempts were made to exclude atmospheric moisture. Glassware was dried for at least 1 h in a 90° C. oven prior to use. HRMS was determined using an LCMS system consisting of a Shimadzu Prominence UFLC with LC-20ADXR pumps, SIL-20AXR autosampler, CTO-20AC column oven, and SPD-M20A DAD detector. All HRMS samples were prepared at 1 mg/mL in MeOH, then diluted 1:20 in MeOH for testing with 2 μL injection volume and mass was detected with an ABSciex TripleTOF 5600+ with CDS (Calibrant Delivery System) and DuoSpray Ion Source.

Synthesis of α-Cyanoketones

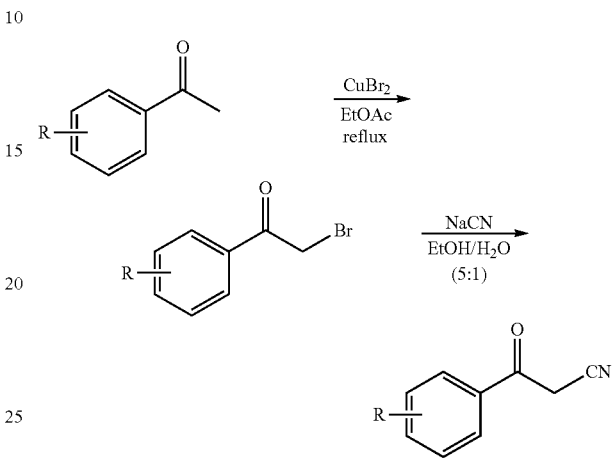

20 mmol of the appropriate acyl ketone was dissolved in 40 mL of ethyl acetate to make a 0.5M solution. 2.6 equivalents of CuBr$_2$ was added and the mixture refluxed with a condenser for 3-5 h until the starting ketone was fully consumed as indicated by TLC or $^1$H NMR. Once the reaction was complete, the mixture was cooled, and then the ethyl acetate was removed under reduced pressure. Hexanes were added to the crude solid and the mixture was sonicated for 5 min. The hexanes were decanted and a fresh volume was added to the remaining solids, again sonicating for 5 min. This process was repeated once more, for a total of 3 extractions. The combined hexane layers, which typically appeared as an amber or light yellow solution, were evaporated under reduced pressure to yield the crude product which typically appeared as yellow or orange oil. Alternatively, a Soxhlet extraction with hexanes overnight (16 h) gives similar isolated yields.

The crude bromoketone oil was next dissolved in a 5:1 mixture of ethanol/water to give a 0.4M solution overall. The solution was cooled over ice, and then 3 equivalents of NaCN were added. The reaction was stirred overnight (16 h), allowing the ice to melt. The solution was then diluted with enough water to roughly double the initial volume. This solution was filtered through a Celite pad to remove suspended solids. This solution was then acidified by adding concentrated HCl to a stirring solution. CAUTION! This will cause the evolution of HCN gas! Only perform in a well-ventilated fume hood! The acidified solution was allowed to stir for 15 minutes. The solution was checked by pH paper to ensure that it was acidic (pH≤2). If not, additional HCl was added, taking the same precautions noted above. Once the solution was acidic, it was transferred to a separatory funnel and extracted 3× with DCM. The organic layers were combined, dried over magnesium sulfate, filtered, and then evaporated under reduced pressure to obtain the final product. Purity was confirmed by $^1$H NMR. If significant impurities are observed, the product can be recrystallized, most typically in isopropanol or toluene.

General Procedure for the Synthesis of Pyrazolo[3,4-b]Pyridines

The following reaction is for 6-(4-tert-butylphenyl)-4-(2-hydroxyphenyl)-3-methyl-1-phenyl-1H-pyrazolo[3,4-b]pyridine-5-carbonitrile (27, CP3-31) on a 1 mmol scale and is representative.

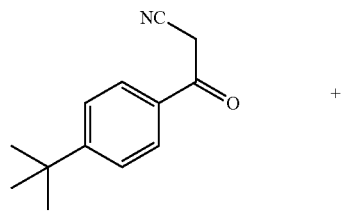

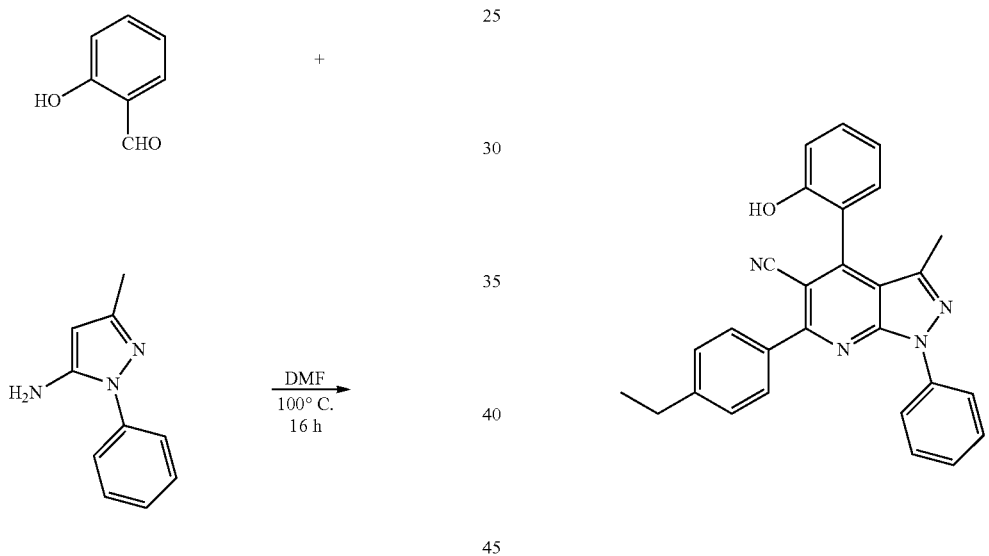

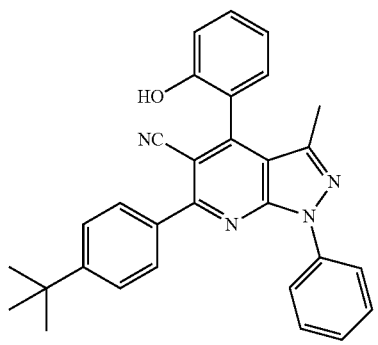

The reagents, 3-(napthalen-2-yl)-3-oxopropanenitrile (195 mg, 1 mmol), 2-hydroxybenzaldehyde (122 mg, 1 mmol), and 3-methyl-1-phenyl-1H-pyrazol-5-amine (173 mg, 1 mmol), were combined in a 50 mL round bottom flask with 5 mL DMF (0.2 M overall). The solution was placed in a 100° C. oil bath and left to stir overnight (~16 h). The solution was then evaporated using a rotary evaporator with an 80° C. water bath to provide the crude as a viscous oil. Once the flask was cooled to room temperature, deionized water (~25 mL) was added to the round bottom and the solution was sonicated for 30 m, or until the product was finely suspended in solution. The suspended product was filtered through a Buchner funnel and washed with 2× deionized water. The isolated crude solid can then be further purified either via trituration, flash chromatography or reverse-phase HPLC. In the case of 27, the crude product was purified via trituration with toluene and dried to provide the product as a fine white powder (240 mg, 52%).

Compounds:

6-(4-Ethylphenyl)-4-(2-hydroxyphenyl)-3-methyl-1-phenyl-1H-pyrazolo[3,4-b]pyridine-5-carbonitrile (1)

Synthesized from 3-(4-ethylphenyl)-3-oxopropanenitrile, 5-amino-3-methyl-1-phenylpyrazole and salicyaldehyde on a 1 mmol scale according to the general procedure for the synthesis of pyrazolo[3,4-b]pyridines. Crude product was purified via flash chromatography on basic alumina using a 3:1 to 1:1 eluent gradient of hexanes/ethyl acetate to yield the final product as an orange powder (106 mg, 25%), m.p. 267-269° C., HRMS (ESI) m/z calculated for $C_{28}H_{22}N_4O$ [M+H]$^+$ 431.1872, found 431.1881.

$^1$H NMR (CDCl$_3$, 400 MHz): δ=1.33 (t, J=7.6 Hz, 3H), 2.23 (s, 3H), 2.78 (q, J=7.6 Hz, 2H), 7.05 (d, J=8.2 Hz, 1H), 7.18 (td, J=7.5, 0.9 Hz, 1H), 7.32-7.41 (m, 4H), 7.47 (td, J 7.8, 1.7 Hz, 1H), 7.54 (t, J=8.0 Hz, 2H), 7.98 (d, J=8.3 Hz, 2H), 8.32 (d, J=7.6 Hz, 2H).

$^{13}$C NMR (CDC$_3$, 101 MHz): δ=13.6, 15.2, 28.8, 29.7, 102.1, 114.2, 116.5, 117.7, 121.0, 121.2, 126.2, 128.1, 129.1, 129.6, 130.4, 131.6, 135.4, 139.0, 144.2, 146.6, 149.2, 150.4, 152.8, 160.7.

6-(4-Ethylphenyl)-3-methyl-4-(2-nitrophenyl)-1-phenyl-1H-pyrazolo[3,4-b]pyridine-5-carbonitrile (6)

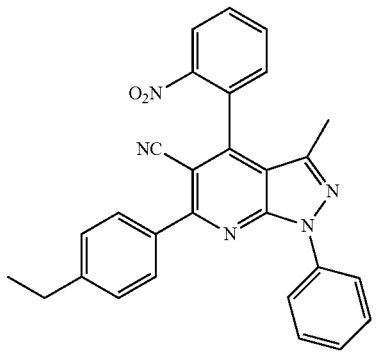 [SMILES: CCc1ccc(-c2nc3c(c(C)nn3-c3ccccc3)c(-c3ccccc3[N+](=O)[O-])c2C#N)cc1]

Synthesized from 3-(4-ethylphenyl)-3-oxopropanenitrile, 5-amino-3-methyl-1-phenylpyrazole and 2-nitrobenzaldehyde on a 0.5 mmol scale according to the general procedure for the synthesis of pyrazolo[3,4-b]pyridines. Crude product was purified via trituration with absolute ethanol to yield the final product as a white powder (211 mg, 28%), m.p. 225-256° C., HRMS (ESI) m/z calculated for $C_{28}H_{21}N_5O_2$ [M+H]$^+$ 460.1773, found 460.1765.

$^1$H NMR (CDCl$_3$, 400 MHz): δ=1.33 (t, J=7.6 Hz, 3H), 2.04 (s, 3H), 2.77 (q, J=7.6 Hz, 2H), 7.37 (m, 3H), 7.55 (m, 3H), 7.84 (m, 1H), 7.92 (m, 1H), 7.99 (d, J=8.3 Hz, 2H), 8.32 (m, 2H), 8.44 (dd, J=8.3, 1.0 Hz, 1H).

$^{13}$C NMR (CDCl$_3$, 101 MHz): δ=13.6, 15.3, 28.8, 100.7, 112.9, 117.1, 121.3, 125.5, 126.5, 128.2, 129.2, 129.6, 129.8, 131.2, 131.4, 134.1, 135.0, 138.8, 143.0, 146.9, 147.5, 149.1, 150.3, 160.3.

4-(2-Cyanophenyl)-6-(4-ethylphenyl)-3-methyl-1-phenyl-1H-pyrazolo[3,4-b]pyridine-5-carbonitrile (7)

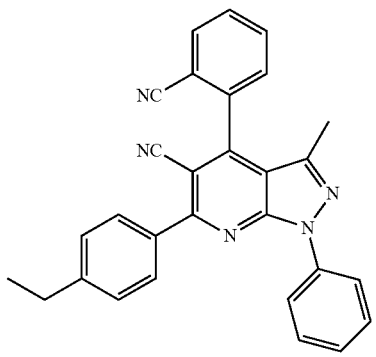 [SMILES: CCc1ccc(-c2nc3c(c(C)nn3-c3ccccc3)c(-c3ccccc3C#N)c2C#N)cc1]

Synthesized from 3-(4-ethylphenyl)-3-oxopropanenitrile, 5-amino-3-methyl-1-phenylpyrazole and 2-cyanobenzaldehyde on a 1 mmol scale according to the general procedure for the synthesis of pyrazolo[3,4-b]pyridines. Crude product was purified via trituration with methanol to yield the final product as a tan powder (65 mg, 15%), m.p. 201-203° C., HRMS (ESI) m/z calculated for $C_{29}H_{21}N_5$ [M+H]$^+$ 440.1875, found 440.1875.

$^1$H NMR (CDCl$_3$, 400 MHz): δ=1.34 (t, J=7.6 Hz, 3H), 2.14 (s, 3H), 2.79 (q, J=7.6 Hz, 2H), 7.35-7.43 (m, 3H), 7.56 (t, J=8.0 Hz, 2H), 7.65 (d, J=7.7 Hz, 1H), 7.77 (m, 1H), 7.89 (m, 1H), 7.98-8.01 (m, 3H), 8.32 (d, J=7.7 Hz, 2H).

$^{13}$C NMR (CDC$_3$, 101 MHz): δ=13.9, 15.2, 28.8, 101.4, 112.9, 113.3, 116.5, 116.9, 121.4, 126.6, 128.2, 129.1, 129.7, 130.0, 130.4, 133.0, 133.3, 135.0, 137.9, 138.7, 143.0, 147.0, 147.8, 150.3, 160.6.

6-(4-Ethylphenyl)-4-(2-iodophenyl)-3-methyl-1-phenyl-1H-pyrazolo[3,4-b]pyridine-5-carbonitrile (8)

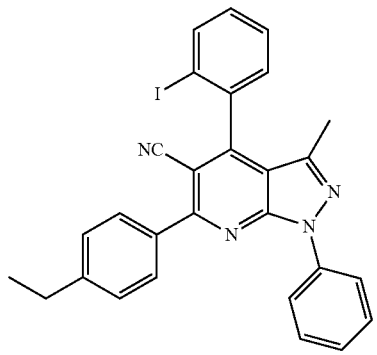 [SMILES: CCc1ccc(-c2nc3c(c(C)nn3-c3ccccc3)c(-c3ccccc3I)c2C#N)cc1]

Synthesized from 3-(4-ethylphenyl)-3-oxopropanenitrile, 5-amino-3-methyl-1-phenylpyrazole and 2-iodobenzaldehyde on a 1 mmol scale according to the general procedure for the synthesis of pyrazolo[3,4-b]pyridines. Crude product was purified via trituration with absolute ethanol to yield the final product as a yellow powder (325 mg, 60%), m.p. 205-207° C., HRMS (ESI) m/z calculated for $C_{28}H_{21}IN_4$ [M+H]$^+$ 541.0889, found 541.0891.

$^1$H NMR (CDCl$_3$, 400 MHz): δ=1.34 (t, J=7.6 Hz, 3H), 2.11 (s, 3H), 2.79 (q, J=7.6 Hz, 2H), 7.49 (m, 8H), 8.06 (m, 3H), 8.38 (d, J=7.7 Hz, 2H).

$^{13}$C NMR (CDC$_3$, 101 MHz): δ=13.7, 15.3, 28.8, 96.9, 101.4, 113.4, 116.9, 121.1, 126.3, 128.1, 128.5, 129.1, 129.1, 129.6, 131.2, 135.2, 139.0, 139.5, 143.7, 146.8, 150.4, 153.7, 160.5.

4-(2-Bromophenyl)-6-(4-ethylphenyl)-3-methyl-1-phenyl-1H-pyrazolo[3,4-b]pyridine-5-carbonitrile (9)

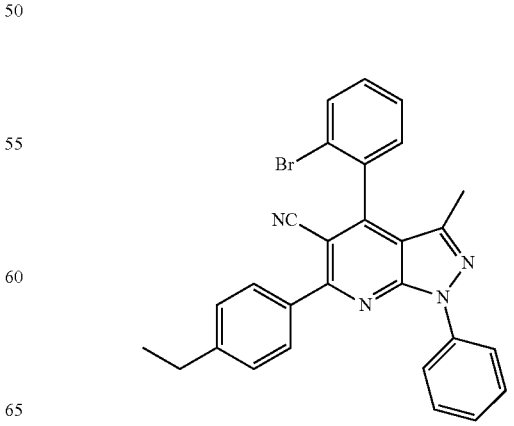

Synthesized from 3-(4-ethylphenyl)-3-oxopropanenitrile, 5-amino-3-methyl-1-phenylpyrazole and 2-bromobenzaldehyde on a 1 mmol scale according to the general procedure for the synthesis of pyrazolo[3,4-b]pyridines. Crude product was purified via trituration with absolute ethanol to yield the final product as an off-white powder (211 mg, 43%), m.p. 208-209° C., HRMS (ESI) m/z calculated for $C_{28}H_{21}BrN_4$ [M+H]$^+$ 493.1028, found 493.1018.

$^1$H NMR (CDCl$_3$, 400 MHz): δ=1.34 (t, J=7.6 Hz, 3H), 2.13 (s, 3H), 2.78 (q, J=7.6 Hz, 2H), 7.48 (m, 8H), 7.84 (d, J=8.1 Hz, 1H), 8.02 (m, 2H), 8.35 (m, 2H).

$^{13}$C NMR (CDC$_3$, 101 MHz): δ=13.4, 15.3, 28.8, 101.5, 113.6, 113.7, 117.0, 117.1, 121.2, 122.2, 126.3, 127.2, 127.8, 128.1, 129.1, 129.6, 130.1, 130.2, 131.3, 131.3, 132.8, 133.2, 133.3, 135.2, 135.4, 138.9, 143.8, 146.8, 149.5, 150.3, 150.9, 160.5.

4-(2-Chlorophenyl)-6-(4-ethylphenyl)-3-methyl-1-phenyl-1H-pyrazolo[3,4-b]pyridine-5-carbonitrile (10)

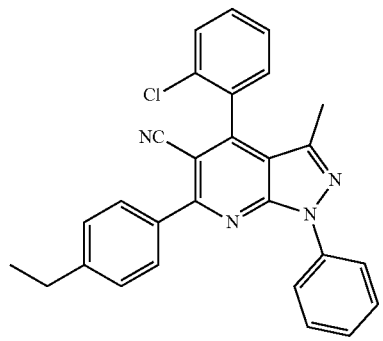 [SMILES: CCc1ccc(-c2nc3c(c(C)nn3-c3ccccc3)c(-c3ccccc3Cl)c2C#N)cc1]

Synthesized from 3-(4-ethylphenyl)-3-oxopropanenitrile, 5-amino-3-methyl-1-phenylpyrazole and 2-chlorobenzaldehyde on a 1 mmol scale according to the general procedure for the synthesis of pyrazolo[3,4-b]pyridines. Crude product was purified via trituration with absolute ethanol to yield the final product as an off-white solid (139 mg, 31%), m.p. 198-199° C., HRMS (ESI) m/z calculated for $C_{28}H_{21}ClN_4$ [M+H]$^+$ 449.1533, found 449.1535.

$^1$H NMR (CDC$_3$, 400 MHz): δ=1.34 (t, J=7.6 Hz, 3H), 2.14 (s, 3H), 2.79 (q, J=7.6 Hz, 2H), 7.5 (m, 9H), 8.01 (d, J=8.3 Hz, 2H), 8.35 (d, J=8.4 Hz, 2H).

$^{13}$C NMR (CDCl$_3$, 101 MHz): δ=13.4, 15.3, 28.8, 101.6, 113.7, 117.1, 121.2, 126.3, 127.2, 128.1, 129.1, 129.6, 130.1, 130.2, 131.3, 132.8, 133.3, 135.2, 138.9, 143.8, 146.8, 149.5, 150.3, 160.5.

6-(4-Ethylphenyl)-4-(2-fluorophenyl)-3-methyl-1-phenyl-1H-pyrazolo[3,4-b]pyridine-5-carbonitrile (11)

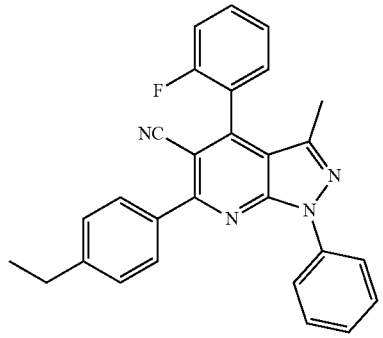 [SMILES: CCc1ccc(-c2nc3c(c(C)nn3-c3ccccc3)c(-c3ccccc3F)c2C#N)cc1]

Synthesized from 3-(4-ethylphenyl)-3-oxopropanenitrile, 5-amino-3-methyl-1-phenylpyrazole and 2-fluorobenzaldehyde on a 0.5 mmol scale according to the general procedure for the synthesis of pyrazolo[3,4-b]pyridines. Crude product was purified via trituration of methanol to yield the final product as a light yellow solid (62 mg, 28%), m.p. 197-199° C., HRMS (ESI) m/z calculated for $C_{28}H_2FN_4$ [M+H]$^+$ 433.1828, found 433.1826.

$^1$H NMR (CDCl$_3$, 400 MHz): δ=1.34 (t, J=7.6 Hz, 3H), 2.22 (s, 3H), 2.79 (q, J=7.6 Hz, 2H), 7.33-7.37 (m, 2H), 7.40-7.44 (m, 3H), 7.53 (m, 3H), 7.63 (m, 1H), 8.00 (m, 2H), 8.33 (m, 2H)

$^{13}$C NMR (CDC$_3$, 101 MHz): δ=13.7, 15.3, 28.8, 102.0, 113.9, 116.3 (d, J=21 Hz), 117.3, 121.3, 121.9 (d, J=16 Hz), 124.6 (d, J=3 Hz), 126.3, 128.1, 129.1, 129.6, 130.9 (d, J=2 Hz), 132.3 (d, J=8 Hz), 135.2, 138.9, 143.7, 146.3, 146.8, 150.2, 158.0, 160.6 (d, J=11 Hz).

6-(4-Ethylphenyl)-3-methyl-4-(2-methylphenyl)-1-phenyl-1H-pyrazolo[3,4-b]pyridine-5-carbonitrile (12)

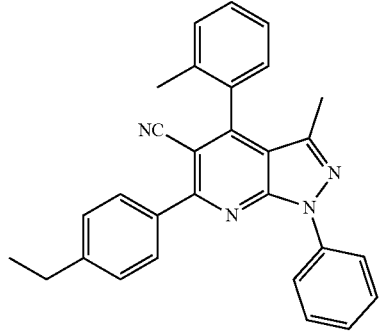 [SMILES: CCc1ccc(-c2nc3c(c(C)nn3-c3ccccc3)c(-c3ccccc3C)c2C#N)cc1]

Synthesized from 3-(4-ethylphenyl)-3-oxopropanenitrile, 5-amino-3-methyl-1-phenylpyrazole and 2-methylbenzaldehyde on a 1 mmol scale according to the general procedure for the synthesis of pyrazolo[3,4-b]pyridines. Crude product was purified via trituration of methanol to yield the final product as a light beige solid (183 mg, 43%), m.p. 203-204° C., HRMS (ESI) m/z calculated for $C_{29}H_{24}N_4$ [M+H]$^+$ 429.2079, found 429.2081.

¹H NMR (CDCl₃, 400 MHz): δ=1.32 (t, J=8.0 Hz, 3H), 2.04 (s, 3H), 2.21 (s, 3H), 2.77 (q, J=8.0 Hz, 2H), 7.31 (m, 2H), 7.39-7.49 (m, 4H), 7.51-7.56 (m, 3H), 8.00 (m, 2H), 8.34 (m, 2H).

¹³C NMR (CDCl₃, 101 MHz): δ=13.5, 15.3, 19.7, 28.8, 101.6, 113.8, 117.3, 121.1, 126.2, 126.6, 128.1, 128.4, 129.1, 129.6, 129.9, 130.6, 133.8, 135.3, 135.4, 139.0, 144.1, 146.7, 150.3, 152.7, 160.6.

6-(4-Ethylphenyl)-4-(2-methanesulfonylphenyl)-3-methyl-1-phenyl-1H-pyrazolo[3,4-b]pyridine-5-carbonitrile (13)

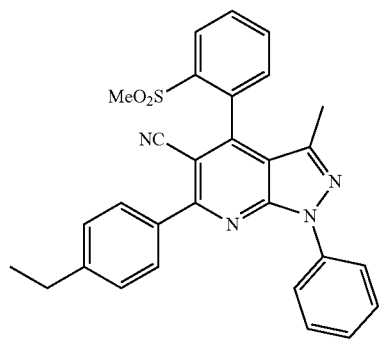 [SMILES: CCc1ccc(-c2nc3c(c(C)nn3-c3ccccc3)c(-c3ccccc3S(C)(=O)=O)c2C#N)cc1]

Synthesized from 3-(4-ethylphenyl)-3-oxopropanenitrile, 5-amino-3-methyl-1-phenylpyrazole and 2-(methylsulfonyl)benzaldehyde on a 1 mmol scale according to the general procedure for the synthesis of pyrazolo[3,4-b]pyridines. The crude product was purified via reverse phase HPLC utilizing a 55%-95% acetonitrile gradient with 0.1% trifluoroacetic acid to isolate the product as a light brown product (50 mg, 10%), m.p. 196-198° C., HRMS (ESI) m/z calculated for C₂₉H₂₄N₄O₂S [M+H]⁺ 493.1698, found 493.1703.

¹H NMR (CDCl₃, 400 MHz): δ=1.32 (t, 3H, J=7.6 Hz), 2.02 (s, 3H), 2.77 (m, 2H, J=7.7 Hz), 3.13 (s, 3H), 7.32 (t, 1H, J=8.1 Hz), 7.40 (d, 2H, J=8.1 Hz), 7.53 (m, 3H, J=8.1 Hz), 7.85 (m, 2H), 7.97 (d, 2H, J=8.2 Hz), 8.31 (t, 3H, J=12 Hz).

¹³C NMR (CDC₃, 101 MHz): δ=14.0, 15.6, 45.3, 101.4, 115.0, 118.3, 121.6, 128.5, 129.4, 129.9, 130.6, 131.3, 131.4, 134.2, 135.3, 139.2, 139.6, 144.3, 147.2, 150.2, 150.2, 160.1.

2-[5-Cyano-6-(4-ethylphenyl)-3-methyl-1-phenyl-1H-pyrazolo[3,4-b]pyridin-4-yl]benzoic acid (14)

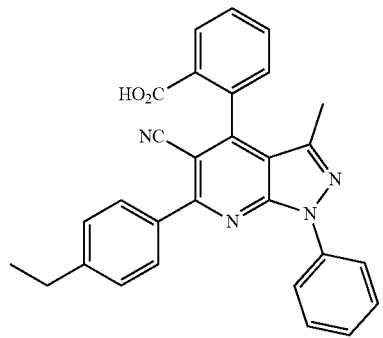 [SMILES: CCc1ccc(-c2nc3c(c(C)nn3-c3ccccc3)c(-c3ccccc3C(=O)O)c2C#N)cc1]

Synthesized from 3-(4-ethylphenyl)-3-oxopropanenitrile, 5-amino-3-methyl-1-phenylpyrazole and 2-carboxybenzaldehyde on a 1 mmol scale according to the general procedure for the synthesis of pyrazolo[3,4-b]pyridines. The crude product was purified via trituration with methanol to yield the final product as an off-white solid (110 mg, 39%), m.p. 198-200° C., HRMS (ESI) m/z calculated for C₂₉H₂₂N₄O₂ [M+H]⁺ 459.1821, found 459.1823.

¹H NMR (CDCl₃, 400 MHz): δ=1.32 (t, J=7.6 Hz, 3H), 1.99 (s, 3H), 2.76 (q, J=7.6 Hz, 2H), 7.31-7.35 (m, 1H), 7.39 (m, 2H), 7.43 (m, 1H), 7.53 (t, J=7.9 Hz, 2H), 7.69 (m, 1H), 7.79 (m, 1H), 7.97 (d, J=8.2 Hz, 2H), 8.30-8.35 (m, 3H)

¹³C NMR (CDC₃, 101 MHz): δ=13.7, 15.3, 28.8, 101.1, 113.5, 117.5, 121.2, 128.1, 128.3, 129.1, 129.6, 130.0, 130.2, 133.3, 135.3, 136.2, 139.0, 143.6, 146.6, 150.2, 152.7, 160.1, 169.2.

6-(4-Ethylphenyl)-3-methyl-1-phenyl-4-[2-(trifluoromethyl)phenyl]-1H-pyrazolo[3,4-b]pyridine-5-carbonitrile (15)

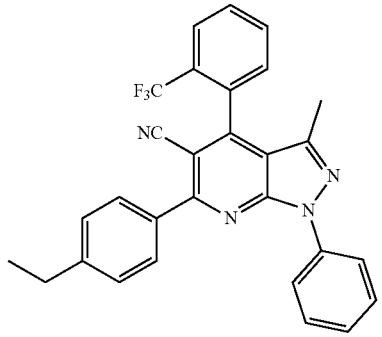 [SMILES: CCc1ccc(-c2nc3c(c(C)nn3-c3ccccc3)c(-c3ccccc3C(F)(F)F)c2C#N)cc1]

Synthesized from 3-(4-ethylphenyl)-3-oxopropanenitrile, 5-amino-3-methyl-1-phenylpyrazole and 2-(triflurormethyl)benzaldehyde on a 0.5 mmol scale according to the general procedure for the synthesis of pyrazolo[3,4-b]pyridines. The crude product was purified via trituration with methanol to yield the final product as an off-white solid (128 mg, 53%), m.p. 193-195° C., HRMS (ESI) m/z calculated for C₂₉H₂₁F₃N₄ [M+H]⁺ 483.1796, found 483.1797.

¹H NMR (CDCl₃, 400 MHz): δ=1.34 (t, J=7.6 Hz, 3H), 2.01 (s, 3H), 2.78 (q, J=7.6 Hz, 2H), 7.35 (m, 1H), 7.42 (d, J=8.3 Hz, 2H), 7.48 (d, J=7.0 Hz, 1H), 7.55 (t, J=8.0 Hz, 2H), 7.78 (m, 2H), 7.99 (m, 3H), 8.35 (d, J=7.7 Hz, 2H)

¹³C NMR (CDC₃, 101 MHz): δ=13.3, 15.3, 28.8, 102.1, 114.0, 117.0, 121.1, 123.5 (q, J=257 Hz), 126.3, 126.8 (q, J=5.0 Hz), 128.2, 128.6, 129.0, 129.1, 129.6, 130.1 (d, J=11 Hz), 132.1, 132.7, 135.0, 138.9, 143.7, 146.8, 149.3, 149.9, 160.0.

6-(4-Ethylphenyl)-4-(2-methoxyphenyl)-3-methyl-1-phenyl-1H-pyrazolo[3,4-b]pyridine-5-carbonitrile (16)

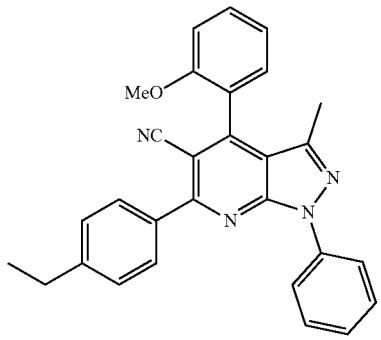 [SMILES: CCc1ccc(-c2nc3c(c(C)nn3-c3ccccc3)c(-c3ccccc3OC)c2C#N)cc1]

Synthesized from 3-(4-ethylphenyl)-3-oxopropanenitrile, 5-amino-3-methyl-1-phenylpyrazole and 2-methoxybenzaldehyde on a 1 mmol scale according to the general procedure for the synthesis of pyrazolo[3,4-b]pyridines. The crude product was purified via trituration with absolute ethanol to yield the final product as an off-white powder (164 mg, 35%), m.p. 196-198° C., HRMS (ESI) m/z calculated for $C_{29}H_{24}N_4O$ $[M+H]^+$ 455.2028, found 445.2038.

$^1$H NMR (CDCl$_3$, 400 MHz): δ=1.33 (t, J=7.6 Hz, 3H), 2.16 (s, 3H), 2.78 (q, J=7.6 Hz, 2H), 3.86 (s, 3H), 7.18 (m, 2H), 7.36 (m, 4H), 7.57 (m, 3H), 7.99 (d, J=8.2 Hz, 2H), 8.34 (d, J=7.8 Hz, 2H).

$^{13}$C NMR (CDC$_3$, 101 MHz): δ=13.8, 15.3, 28.8, 55.7, 102.2, 111.4, 114.3, 120.8, 121.1, 123.0, 126.1, 128.0, 129.1, 129.6, 130.4, 131.6, 135.5, 139.1, 144.2, 146.5, 149.9, 150.4, 156.5, 160.5.

6-(4-Ethylphenyl)-3-methyl-1-phenyl-4-[2-(trifluoromethoxy)phenyl]-1H-pyrazolo[3,4-b]pyridine-5-carbonitrile (17)

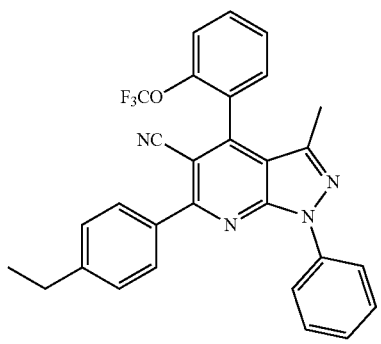 [SMILES: CCc1ccc(-c2nc3c(c(C)nn3-c3ccccc3)c(-c3ccccc3OC(F)(F)F)c2C#N)cc1]

Synthesized from 3-(4-ethylphenyl)-3-oxopropanenitrile, 5-amino-3-methyl-1-phenylpyrazole and 2-trifluoromethoxybenzaldehyde on a 1 mmol scale according to the general procedure for the synthesis of pyrazolo[3,4-b]pyridines. The crude product was purified via trituration with absolute ethanol to yield the final product as an off-white flakey solid (131 mg, 26%), m.p. 160-162° C., HRMS (ESI) m/z calculated for $C_{29}H_{21}F_3N_4O$ $[M+H]^+$ 499.1745, found 499.1743.

$^1$H NMR (CDCl$_3$, 400 MHz): δ=1.34 (t, J=7.6 Hz, 3H), 2.15 (s, 3H), 2.78 (q, J=7.6 Hz, 2H), 7.35 (m, 1H), 7.42 (d, J=8.3 Hz, 2H), 7.54 (m, 5H), 7.69 (m, 1H), 8 (m, 2H), 8.35 (d, J=7.7 Hz, 2H).

$^{13}$C NMR (CDC$_3$, 101 MHz): δ=13.5, 15.3, 28.8, 102.0, 113.8, 117.0, 119.0, 121.2, 121.2, 126.3, 127.1, 127.6, 128.1, 129.1, 129.6, 131.0, 131.8, 135.1, 138.9, 143.6, 146.3, 146.8, 147.0, 150.2, 160.4.

6-(4-Ethylphenyl)-3-methyl-1,4-diphenyl-1H-pyrazolo[3,4-b]pyridine-5-carbonitrile (18)

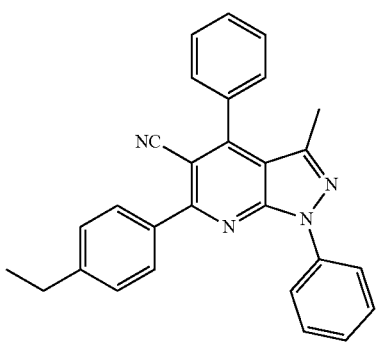 [SMILES: CCc1ccc(-c2nc3c(c(C)nn3-c3ccccc3)c(-c3ccccc3)c2C#N)cc1]

Synthesized from 3-(4-ethylphenyl)-3-oxopropanenitrile, 5-amino-3-methyl-1-phenylpyrazole and benzaldehyde on a 1 mmol scale according to the general procedure for the synthesis of pyrazolo[3,4-b]pyridines. The crude product was purified via trituration with methanol to yield the final product as a fine white powder (115 mg, 28%), m.p. 198-199° C., HRMS (ESI) m/z calculated for $C_{28}H_{22}N_4$ $[M+H]^+$ 415.1922, found 415.1923.

$^1$H NMR (CDC$_3$, 400 MHz): δ=1.33 (t, J=7.6 Hz, 3H), 2.16 (s, 3H), 2.78 (q, J=7.6 Hz, 2H), 7.33-7.36 (m, 1H), 7.41 (d, J=8.1 Hz, 2H), 7.52-7.56 (m, 4H), 7.61-7.63 (m, 3H), 7.98 (d, J=8.2 Hz, 2H), 8.33 (d, J=8.6 Hz, 2H).

$^{13}$C NMR (CDC$_3$, 101 MHz): δ=14.6, 15.2, 28.8, 101.3, 113.6, 117.7, 121.2, 126.3, 128.1, 128.6, 128.9, 129.1, 129.6, 129.9, 134.1, 135.4, 139.0, 143.9, 146.7, 150.3, 152.7, 160.6.

6-(4-Ethylphenyl)-4-(3-hydroxyphenyl)-3-methyl-1-phenyl-1H-pyrazolo[3,4-b]pyridine-5-carbonitrile (19)

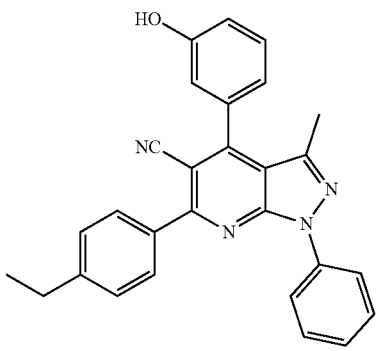 [SMILES: CCc1ccc(-c2nc3c(c(C)nn3-c3ccccc3)c(-c3cccc(O)c3)c2C#N)cc1]

Synthesized from 3-(4-ethylphenyl)-3-oxopropanenitrile, 5-amino-3-methyl-1-phenylpyrazole and 3-hydroxybenzaldehyde on a 1 mmol scale according to the general procedure for the synthesis of pyrazolo[3,4-b]pyridines. The crude product was purified via trituration with methanol to yield the final product as an off-white solid (35 mg, 8%), m.p. 172-174° C., HRMS (ESI) m/z calculated for $C_{28}H_{22}N_4O$ [M+H]$^+$ 431.1872, found 431.1873.

$^1$H NMR (CDCl$_3$, 400 MHz): δ=1.33 (t, J=7.6 Hz, 3H), 2.2 (s, 3H), 2.78 (q, J=7.6 Hz, 2H), 5.30 (br s, 1H), 6.99 (s, 1H), 7.07 (m 2H), 7.34 (m, 1H), 7.41 (d, J=8.2, 2H), 7.47 (t, J=7.9 Hz, 1H), 7.54 (m, 2H), 7.97 (d, J=8.2, 2H), 8.32 (m, 2H).

$^{13}$C NMR (CDCl$_3$, 101 MHz): δ=14.4, 15.2, 28.8, 101.0, 113.5, 115.9, 117.1, 117.7, 121.3, 126.3, 128.1, 129.1, 129.6, 130.0, 135.3, 138.8, 144.1, 146.7, 150.3, 152.4, 155.9, 160.6.

6-(4-Ethylphenyl)-4-(4-hydroxyphenyl)-3-methyl-1-phenyl-1H-pyrazolo[3,4-b]pyridine-5-carbonitrile (20)

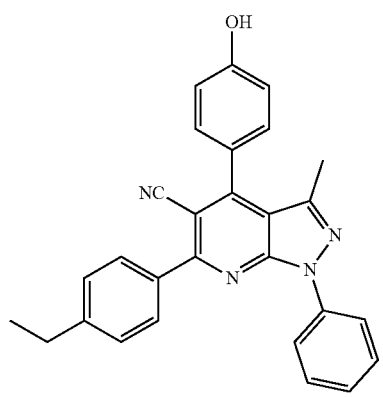 [SMILES: CCc1ccc(-c2nc3c(c(C)nn3-c3ccccc3)c(-c3ccc(O)cc3)c2C#N)cc1]

Synthesized from 3-(4-ethylphenyl)-3-oxopropanenitrile, 5-amino-3-methyl-1-phenylpyrazole and 4-hydroxybenzaldehyde on a 1 mmol scale according to the general procedure for the synthesis of pyrazolo[3,4-b]pyridines. The crude product was purified via trituration with ethanol to yield the final product as an off-white solid (180 mg, 42%), m.p. 238-240° C., HRMS (ESI) m/z calculated for $C_{28}H_{22}N_4O$ [M+H]$^+$ 431.1872, found 431.1875.

$^1$H NMR (CDCl$_3$, 400 MHz): δ=1.34 (t, J=7.6 Hz, 3H), 2.23 (s, 3H), 2.78 (q, J=7.6 Hz, 2H), 5.37 (br s, 1H), 7.05 (d, J=8.6 Hz, 2H), 7.34 (m, 1H), 7.43 (dd, J=15.5, 8.5 Hz, 4H), 7.54 (t, J=8.1 Hz, 2H), 7.97 (m, 2H), 8.33 (d, J=7.7 Hz, 2H).

$^{13}$C NMR (CDC$_3$, 101 MHz): δ=14.8, 15.3, 28.8, 101.2, 113.8, 115.7, 118.2, 121.3, 126.0, 126.3, 128.1, 129.1, 129.6, 130.6, 135.4, 138.9, 144.1, 146.7, 150.4, 152.9, 157.45, 160.8.

Methyl 2-[5-cyano-6-(4-ethylphenyl)-3-methyl-1-phenyl-1H-pyrazolo[3,4-b]pyridin-4-yl]benzoate (21)

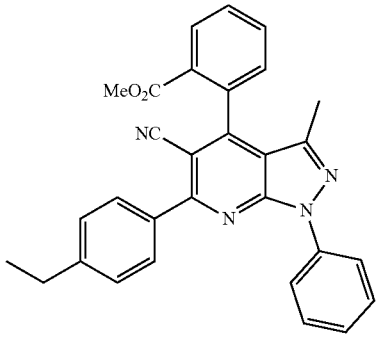 [SMILES: CCc1ccc(-c2nc3c(c(C)nn3-c3ccccc3)c(-c3ccccc3C(=O)OC)c2C#N)cc1]

Synthesized from 3-(4-ethylphenyl)-3-oxopropanenitrile, 5-amino-3-methyl-1-phenylpyrazole and methyl-2-formyl-benzenecarboxylate on a 1 mmol scale according to the general procedure for the synthesis of pyrazolo[3,4-b]pyridines. The crude product was purified via trituration with ethanol to provide the final product as a tan powder (34 mg, 7%), m.p. 141-143° C., HRMS (ESI) m/z calculated for $C_{30}H_{24}N_4O_3$ [M+H]$^+$ 473.1977, found 473.1976.

$^1$H NMR (CDCl$_3$, 400 MHz): δ=1.32 (t, J=7.6 Hz, 3H), 1.99 (s, 3H), 2.76 (q, J=7.7 Hz, 2H), 3.73 (s, 3H), 7.32 (d, J=8.0 Hz, 1H), 7.40 (m, 3H), 7.52 (t, J=7.8 Hz, 2H), 7.69 (d, J=8.0 Hz, 1H), 7.75 (d, J=8.0 Hz, 1H), 7.99 (d, J=8.0 Hz, 2H), 8.33 (m, 3H).

$^{13}$C NMR (CDCl$_3$, 101 MHz): δ=13.7, 15.3, 28.8, 52.3, 101.0, 113.5, 117.5, 121.1, 126.1, 128.1, 129.1, 129.1, 129.3, 129.6, 129.9, 130.2, 131.2, 132.6, 135.4, 139.1, 143.6, 146.6, 150.2, 153.1, 160.1, 165.8.

6-(4-Ethylphenyl)-4-(2-ethynylphenyl)-3-methyl-1-phenyl-1H-pyrazolo[3,4-b]pyridine-5-carbonitrile (22)

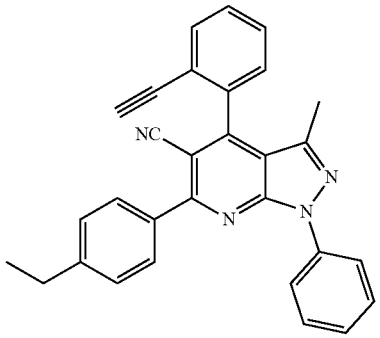 [SMILES: C#Cc1ccccc1-c1c(C#N)c(-c2ccc(CC)cc2)nc2c1c(C)nn2-c1ccccc1]

Synthesized from 3-(4-ethylphenyl)-3-oxopropanenitrile, 5-amino-3-methyl-1-phenylpyrazole and methyl-2-formyl-benzenecarboxylate on a 1 mmol scale according to the general procedure for the synthesis of pyrazolo[3,4-b]pyridines. The crude product was purified via trituration with methanol to yield the final product as an off-white solid (18 mg, 4%), m.p. 148-150° C., HRMS (ESI) m/z calculated for $C_{30}H_{22}N_4$ [M+H]$^+$ 439.1922, found 439.1919.

¹H NMR (CDCl₃, 400 MHz): δ=1.32 (t, J=7.6 Hz, 3H), 2.14 (s, 3H), 2.77 (q, J=7.6 Hz, 2H), 2.95 (s, 1H), 7.33 (t, J=7.8 Hz, 1H), 7.40 (d, J=8.1 Hz, 2H), 7.56 (m, 1H), 7.51-7.60 (m, 4H), 7.77 (m, 1H), 8.00 (m, 2H), 8.36 (d, J=7.8 Hz, 2H).

¹³C NMR (CDC₃, 101 MHz): δ=13.8, 15.3, 28.8, 80.8, 82.0, 101.6, 113.8, 117.3, 121.0, 121.7, 126.2, 128.1, 128.8, 129.1, 129.1, 129.6, 129.8, 133.3, 135.3, 137.1, 139.0, 144.1, 146.7, 150.2, 150.9, 160.4.

4-(2-Hydroxyphenyl)-3-methyl-6-(4-methylphenyl)-1-phenyl-1H-pyrazolo[3,4-b]pyridine-5-carbonitrile (23)

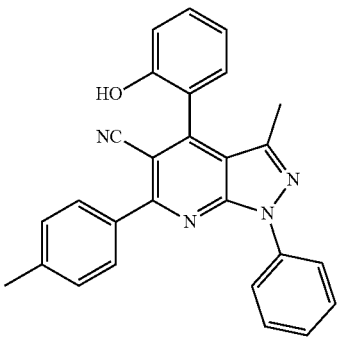

Synthesized from 3-(4-methylphenyl)-3-oxopropanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with acetone to yield the final product as a fine white powder (49 mg, 12%), m.p. 269-270° C., HRMS (ESI) m/z calculated for C₂₇H₂₀N₄O [M+H]⁺ 417.1715, found 417.1718.

¹H NMR (CDCl₃, 400 MHz): δ=2.23 (s, 3H), 2.48 (s, 3H), 7.04 (d, J=8.2 Hz, 1H), 7.18 (td, J=7.5, 2.0 Hz, 1H), 7.40-7.31 (m, 4H), 7.47 (m, 1H), 7.51-7.58 (m, 2H), 7.95 (d, J=8.2 Hz, 2H), 8.32 (dd, J=8.7, 1.1 Hz, 2H).

¹³C NMR (acetone-d₆, 101 MHz): δ=12.8, 20.4, 102.6, 114.4, 116.1, 117.1, 119.8, 120.8, 121.5, 126.0, 129.0, 129.0, 129.5, 130.4, 131.4, 135.6, 139.2, 140.2, 144.3, 150.2, 150.2, 154.4, 160.4.

4-(2-hydroxyphenyl)-3-methyl-6-(3-methylphenyl)-1-phenyl-1H-pyrazolo[3,4-b]pyridine-5-carbonitrile (24)

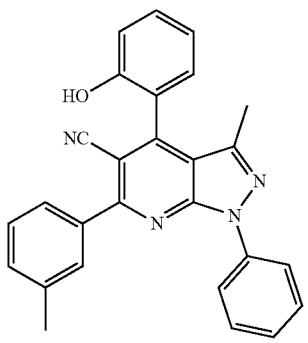 [SMILES: Cc1cccc(-c2nc3c(c(C)nn3-c3ccccc3)c(-c3ccccc3O)c2C#N)c1]

Synthesized from 3-methylbenzoylacetonitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via flash chromatography using a 2:1 to 1:1 gradient of hexanes/ethyl acetate to yield the final product as a yellow powder (126 mg, 31% yield), m.p. 261-262° C., HRMS (ESI) m/z calculated for C₂₇H₂N₄O [M+H]⁺ 417.1715, found 417.1717.

¹H NMR (CDC₃, 400 MHz): δ=2.21 (s, 3H), 2.48 (s, 3H), 6.99 (d, J=7.5 Hz, 1H), 7.15 (t, J=1.0 Hz, 1H), 7.34 (m, 3H), 7.44 (m, 2H), 7.52 (m, 2H), 7.8 (d, J=2.4 Hz, 2H), 8.29 (d, J=7.6 Hz, 2H).

¹³C NMR (CDC₃, 101 MHz): δ=13.7, 21.5, 102.3, 114.3, 116.4, 117.7, 120.7, 121.3, 126.3, 126.7, 128.4, 129.1, 130.2, 130.3, 130.9, 131.6, 137.9, 138.2, 138.8, 144.4, 149.6, 150.3, 153.1, 161.0.

4-(2-hydroxyphenyl)-3-methyl-6-(2-methylphenyl)-1-phenyl-1H-pyrazolo[3,4-b]pyridine-5-carbonitrile (25)

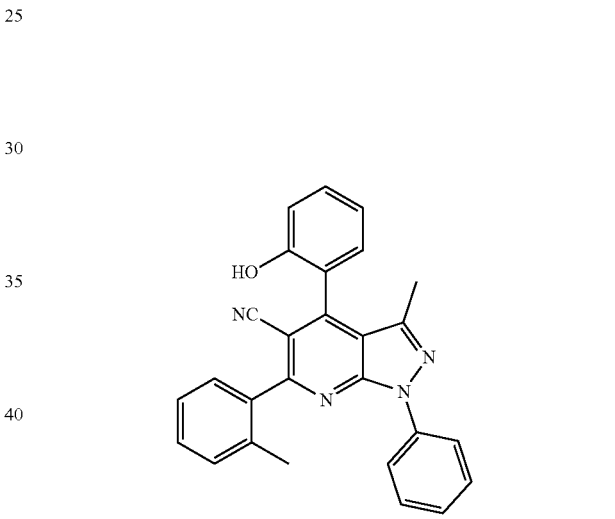

Synthesized from 3-(2-methylphenyl)-3-oxopropanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via reverse phase HPLC utilizing a 55%-95% acetonitrile gradient with 0.1% trifluoroacetic acid to isolate the product as a fine yellow powder (24 mg, 6%), m.p. 243-244° C., HRMS (ESI) m/z calculated for C₂₇H₂₀N₄O [M+H]⁺ 417.1715, found 417.1713.

¹H NMR (CDCl₃, 400 MHz): δ=2.24 (s, 3H), 2.39 (s, 3H), 6.91 (dd, J=8.3, 0.6 Hz, 1H), 7.13 (td, J=7.5, 1.1 Hz, 1H), 7.28-7.43 (m, 6H), 7.45-7.52 (m, 3H), 8.23 (m, 2H).

¹³C NMR (CDC₃, 101 MHz): δ=13.8, 20.0, 104.2, 114.2, 116.4, 117.0, 121.0, 121.3, 125.8, 126.4, 129.1, 129.6, 129.8, 130.5, 130.7, 131.7, 136.4, 137.9, 138.8, 144.3, 148.3, 148.4, 150.1, 152.8, 162.1.

4-(2-hydroxyphenyl)-3-methyl-1-phenyl-6-[4-(propan-2-yl)phenyl]-1H-pyrazolo[3,4-b]pyridine-5-carbonitrile (26)

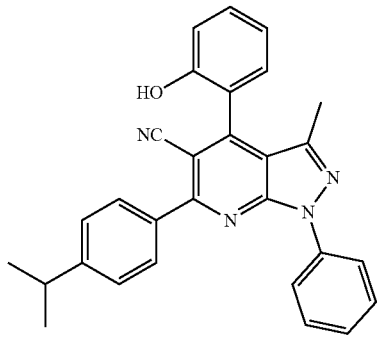 [SMILES: Cc1nn(-c2ccccc2)c2nc(-c3ccc(C(C)C)cc3)c(C#N)c(-c3ccccc3O)c12]

Synthesized from 3-oxo-3-[4-(propan-2-yl)phenyl]propanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with methanol to yield the final product as an off-white powder (93 mg, 21%), m.p. 265-267° C., HRMS (ESI) m/z calculated for $C_{29}H_{24}N_4O$ [M+H]$^+$ 445.2028, found 445.2029.

$^1$H NMR (CDCl$_3$, 400 MHz): δ=1.34 (d, J=6.8 Hz, 6H), 2.23 (s, 1H), 3.03 (m, 1H), 5.15 (s, 1H), 7.04 (d, J=8.2 Hz, 1H), 7.19 (m, J=7.5 Hz, 1H), 7.36 (m, 2H) 7.43 (d, J=8.2 Hz, 2H), 7.48 (m, 1H), 7.54 (t, J=8.0 Hz, 2H), 8.00 (d, J=8.3 Hz, 2H), 8.33 (m, 2H).

$^{13}$C NMR (DMSO-d$_6$, 101 MHz): δ=13.7, 24.1, 33.8, 102.5, 114.5, 116.5, 118.0, 119.6, 121.3, 121.4, 126.8, 127.0, 129.7, 129.9, 130.7, 131.9, 135.8, 138.9, 144.6, 150.1, 150.9, 151.1, 155.0, 160.5.

6-(4-tert-butylphenyl)-4-(2-hydroxyphenyl)-3-methyl-1-phenyl-1H-pyrazolo[3,4-b]pyridine-5-carbonitrile (27)

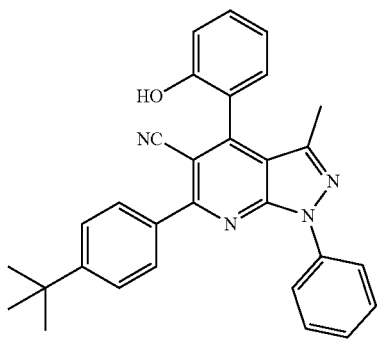 [SMILES: Cc1nn(-c2ccccc2)c2nc(-c3ccc(C(C)(C)C)cc3)c(C#N)c(-c3ccccc3O)c12]

Synthesized from 3-(4-tert-butylphenyl)-3-oxopropanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with toluene to yield the final product as a fine white powder (240 mg, 52%), m.p. 219-221° C., HRMS (ESI) m/z calculated for $C_3H_{26}N_4O$ [M+H]$^+$ 459.2185, found 459.2180.

$^1$H NMR (CDCl$_3$, 400 MHz): δ=1.42 (s, 9H), 2.19 (s, 3H), 2.23 (s, 1H), 7.06 (d, J=8.2 Hz, 1H), 7.19 (t, J=7.5 Hz, 1H), 7.33-7.39 (m, 2H), 7.49 (m, 1H), 7.52-7.61 (m, 4H), 8.02 (d, J=8.7 Hz, 2H), 8.33 (d, J=7.6 Hz, 2H).

$^{13}$C NMR (CDC$_3$, 101 MHz): δ=13.6, 31.2, 34.9, 102.1, 114.1, 116.4, 117.7, 121.1, 121.3, 125.5, 126.2, 129.1, 129.4, 130.4, 131.6, 135.0, 138.9, 144.2, 149.1, 149.1, 150.4, 152.7, 153.5, 160.5.

4-(2-hydroxyphenyl)-3-methyl-1-phenyl-6-(4-propylphenyl)-1H-pyrazolo[3,4-b]pyridine-5-carbonitrile (28)

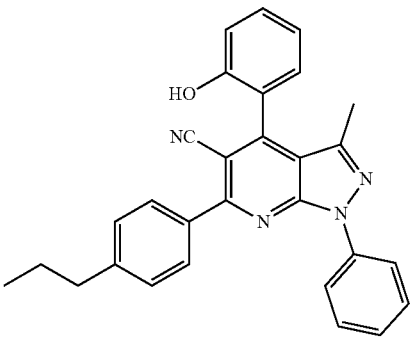 [SMILES: CCCc1ccc(-c2nc3c(c(C)nn3-c3ccccc3)c(-c3ccccc3O)c2C#N)cc1]

Synthesized from 3-oxo-3-(4-propylphenyl)propanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with isopropanol to yield the final product as an off-white powder (256 mg, 58%), m.p. 240-241° C., HRMS (ESI) m/z calculated for $C_{29}H_{24}N_4O$ [M+H]$^+$ 445.2028, found 445.2025.

$^1$H NMR (CDCl$_3$, 400 MHz): δ=0.96 (t, J=7.3 Hz, 3H), 1.68 (m, 2H), 2.13 (s, 3H), 2.68 (t, J=7.6 Hz, 2H), 7.04 (t, J=7.3 Hz, 1H), 7.15 (d, J=8.3 Hz, 1H), 7.41 (m, 5H), 7.59 (t, J=7.9 Hz, 2H), 7.88 (d, J=8.1 Hz, 2H), 8.23 (d, J=7.7 Hz, 2H), 10.15 (s, 1H).

$^{13}$C NMR (DMSO-d$_6$, 101 MHz): δ=13.7, 14.2, 24.3, 37.5, 102.5, 114.4, 116.5, 117.9, 119.5, 121.3, 121.5, 126.9, 128.9, 129.8, 130.6, 131.8, 135.7, 138.9, 144.6, 145.0, 150.1, 151.0, 155.1, 160.5.

4-(2-hydroxyphenyl)-3-methyl-6-(naphthalen-2-yl)-1-phenyl-1H-pyrazolo[3,4-b]pyridine-5-carbonitrile (29)

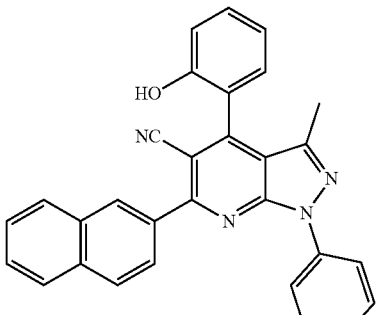

Synthesized from 3-(naphthalen-2-yl)-3-oxopropanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via flash chromatography with alumina and a 3:2 hexanes/ethyl acetate eluent to yield the final product as a fine white powder (48 mg, 11%), m.p. 241-242° C., HRMS (ESI) m/z calculated for $C_{30}H_{20}N_4O$ [M+H]$^+$ 453.1715, found 453.1713.

$^1$H NMR (CDCl$_3$, 400 MHz): δ=2.26 (s, 3H), 7.07 (dd, J=8.4, 0.8 Hz, 1H), 7.21 (td, J=7.5, 2.0 Hz, 1H), 7.35 (m, 1H), 7.41 (dd, J=7.5, 1.6 Hz, 1H), 7.47-7.61 (m, 5H), 7.94 (d, J=7.3 Hz, 1H), 8.00-8.06 (m, 2H), 8.14 (dd, J=8.5, 1.9 Hz, 1H), 8.36 (dd, J=8.7, 1.2 Hz, 2H), 8.56 (s, 1H).

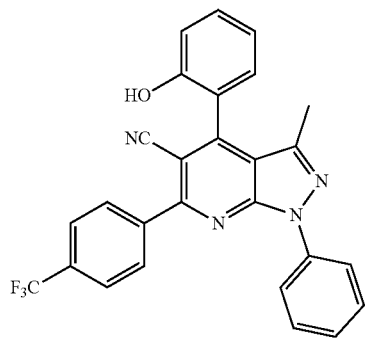 [SMILES: Cc1nn(-c2ccccc2)c2nc(-c3ccc(C(F)(F)F)cc3)c(C#N)c(-c3ccccc3O)c12]

$^{13}$C NMR (CDC$_3$, 101 MHz): δ=13.7, 102.5, 114.3, 116.5, 117.6, 121.1, 121.2, 126.3, 126.5, 126.6, 127.3, 127.7, 128.3, 129.0, 129.1, 129.8, 130.4, 131.7, 132.9, 134.0, 135.3, 138.9, 144.3, 150.4, 152.7, 160.6, 175.3.

4-(2-hydroxyphenyl)-3-methyl-1-phenyl-6-[4-(trifluoromethyl)phenyl]-1H-pyrazolo[3,4-b]pyridine-5-carbonitrile (30)

Synthesized from 3-oxo-3-[4-(trifluoromethyl)phenyl]propanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with methanol to yield the final product as an off-white powder (56 mg, 12%), m.p. 254-256° C., HRMS (ESI) m/z calculated for $C_{27}H_{17}F_3N_4O$ [M+H]$^+$ 471.1432, found 471.1428.

$^1$H NMR (CDCl$_3$, 400 MHz): δ=2.25 (s, 3H), 5.21 (s, 1H), 7.05 (d, J=8.2 Hz, 1H), 7.2 (td; J=7.5, 0.9 Hz; 1H), 7.36 (m, 2H), 7.49 (m, 1H), 7.55 (m 2H), 7.84 (d, J=8.2 Hz, 2H), 8.16, (d, J=8.1 Hz, 2H), 8.29 (m, 2H).

$^{13}$C NMR (DMSO-d$_6$, 101 MHz): δ=13.7, 102.3, 114.4, 116.0, 117.0, 119.1, 120.5, 121.1, 124.0 (q, J=270 Hz), 125.4 (q, J=4.0 Hz), 126.5, 129.2, 130.1 (q, J=31 Hz), 130.2, 130.2, 131.5, 138.1, 141.5, 144.2, 149.4, 150.4, 154.4, 158.6.

6-(4-fluorophenyl)-4-(2-hydroxyphenyl)-3-methyl-1-phenyl-1H-pyrazolo[3,4-b]pyridine-5-carbonitrile (31)

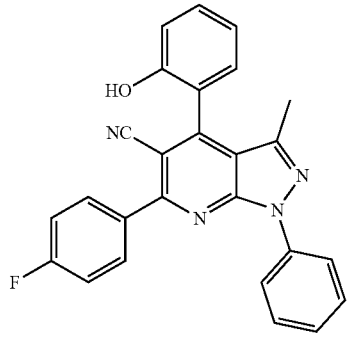

Synthesized from 3-(4-fluorophenyl)-3-oxopropanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with methanol to yield the final product as an off-white powder (131 mg, 32%), m.p. 234-236° C., HRMS (ESI) m/z calculated for $C_{26}H_{17}FN_4O$ [M+H]$^+$ 421.1464, found 421.1461.

$^1$H NMR (CDCl$_3$, 400 MHz): δ=2.25 (s, 3H), 5.21 (s, 1H), 7.05 (d, J=8.8 Hz, 1H), 7.20 (t, J=8.1 Hz, 1H), 7.37 (d, J=7.5 Hz, 2H), 7.50 (d, J=2.6 Hz, 1H), 7.53 (s, 1H), 7.57 (s, 1H), 7.84 (d, J=8.9 Hz, 2H), 8.17 (s, 2H), 8.30 (s, 2H).

$^{13}$C NMR (DMSO-d$_6$, 101 MHz): δ=13.7, 102.7, 114.6, 115.9, 116.1, 116.5, 117.8, 119.7, 121.2, 121.6, 127.0, 129.8, 130.7, 132.0, 132.2 (d, J=8 Hz), 134.7 (d, J=3 Hz), 138.8, 144.7, 150.4 (d, J=90 Hz), 155.0, 159.5, 163.7 (d, J=250 Hz).

6-(4-chlorophenyl)-4-(2-hydroxyphenyl)-3-methyl-1-phenyl-1H-pyrazolo[3,4-b]pyridine-5-carbonitrile (32)

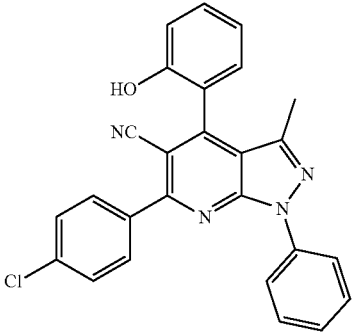 [SMILES: Cc1nn(-c2ccccc2)c2nc(-c3ccc(Cl)cc3)c(C#N)c(-c3ccccc3O)c12]

Synthesized from 3-(4-chlorophenyl)-3-oxopropanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with ethyl acetate to yield the final product as a fine white powder (95 mg, 28%), m.p. 281-282° C., HRMS (ESI) m/z calculated for $C_{26}H_{17}ClN_4O$ [M+H]$^+$ 437.1169, found 437.1159.

¹H NMR (CDCl₃, 400 MHz): δ=2.23 (s, 3H), 7.04 (d, J=7.6 Hz, 1H), 7.18 (m, 1H), 7.34 (m, 2H), 7.48 (m, 1H), 7.53 (m, 4H), 7.99 (m, 2H), 8.28 (m, 2H).

¹³C NMR (DMSO-d₆, 101 MHz): δ=13.1, 102.1, 114.1, 115.9, 117.1, 119.1, 120.6, 121.0, 126.4, 128.5, 129.2, 130.1, 131.1, 131.4, 135.1, 136.5, 138.2, 144.1, 149.4, 150.4, 154.4, 158.7.

4-(2-hydroxyphenyl)-6-(4-iodophenyl)-3-methyl-1-phenyl-1H-pyrazolo[3,4-b]pyridine-5-carbonitrile (33)

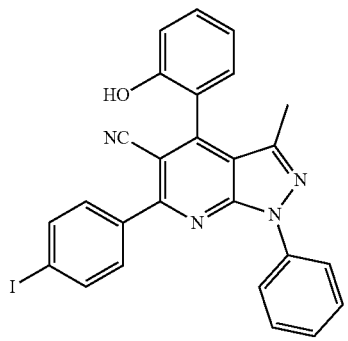 [SMILES: Cc1nn(-c2ccccc2)c2nc(-c3ccc(I)cc3)c(C#N)c(-c3ccccc3O)c12]

Synthesized from 3-(4-iodophenyl)-3-oxopropanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with ethanol to yield the final product as a fine white powder (271 mg, 51%), m.p. 289-291° C., HRMS (ESI) m/z calculated for $C_{26}H_{17}IN_4O$ [M+H]⁺ 529.0525, found 529.0521.

¹H NMR (CDCl₃, 400 MHz): δ=2.24 (s, 3H), 7.04 (d, J=8.2 Hz, 1H), 7.19 (m, 1H), 7.32-7.39 (m, 2H), 7.49 (m, 1H), 7.52-7.58 (m, 2H), 7.79 (d, J=8.4 Hz, 2H), 7.92 (d, J=8.6 Hz, 2H), 8.29 (d, J=7.5 Hz, 2H).

¹³C NMR (CDC₃, 101 MHz): δ=13.6, 97.0, 102.1, 114.4, 116.4, 117.3, 121.0, 121.3, 121.3, 126.4, 129.1, 130.4, 131.2, 131.8, 137.4, 137.8, 138.8, 144.2, 149.1, 150.2, 152.5, 159.5.

6-(4-cyanophenyl)-4-(2-hydroxyphenyl)-3-methyl-1-phenyl-1H-pyrazolo[3,4-b]pyridine-5-carbonitrile (34)

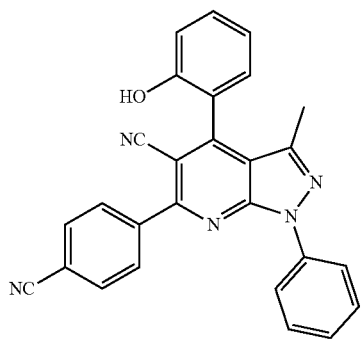 [SMILES: Cc1nn(-c2ccccc2)c2nc(-c3ccc(C#N)cc3)c(C#N)c(-c3ccccc3O)c12]

Synthesized from 4-(2-cyanoacetyl)benzonitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with methanol to yield the final product as a fine white powder (212 mg, 50%), m.p. 165-166° C., HRMS (ESI) m/z calculated for $C_{27}H_{17}N_5O$ [M+H]⁺ 428.1511, found 428.1500.

¹H NMR (CDCl₃, 400 MHz): δ=2.16 (s, 3H), 7.1 (m, 2H), 7.44 (m, 3H), 7.6 (t, J=7.9 Hz, 2H), 8.16 (m, 6H), 10.13 (s, 1H).

¹³C NMR (DMSO-d₆, 101 MHz): δ=13.7, 102.8, 113.2, 115.0, 116.5, 117.5, 118.8, 119.7, 121.0, 121.6, 127.0, 129.7, 130.7, 130.8, 132.1, 132.9, 138.7, 142.4, 144.8, 149.9, 151.0, 155.0, 158.7.

4-(2-hydroxyphenyl)-3-methyl-6-(4-nitrophenyl)-1-phenyl-1H-pyrazolo[3,4-b]pyridine-5-carbonitrile (35)

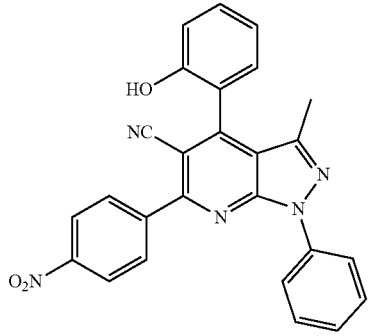 [SMILES: Cc1nn(-c2ccccc2)c2nc(-c3ccc([N+](=O)[O-])cc3)c(C#N)c(-c3ccccc3O)c12]

Synthesized from 3-(4-nitrophenyl)-3-oxopropanenitrile, 5-amino-3-methyl-1-phenylpyrazole and 2-hydroxybenzaldehyde on a 8.5 mmol scale according to the general procedure for the synthesis of pyrazolo[3,4-b]pyridines. The crude product was purified via trituration with acetonitrile to yield the final product as a fine light yellow powder (692 mg, 18%), m.p. 257-258° C., HRMS (ESI) m/z calculated for $C_{26}H_{17}N_5O_3$ [M+H]⁺ 448.1409, found 448.1409.

¹H NMR (CDCl₃, 400 MHz): δ=2.25 (s, 3H), 5.19 (s, 1H), 7.04 (d, J=7.6 Hz, 1H), 7.17-7.21 (m, 1H), 7.35-7.38 (m, 2H), 7.47-7.57 (m, 3H), 8.20-8.22 (m, 2H), 8.25-8.27 (m, 2H), 8.41-8.43 (m, 2H).

¹³C NMR (DMSO-d₆, 101 MHz): δ=13.7, 102.9, 114.9, 116.5, 117.5, 129.7, 120.9, 121.7, 125.1, 127.2, 129.8, 130.7, 131.4, 132.1, 138.6, 144.1, 144.8, 148.8, 149.8, 151.0, 155.0, 158.5.

6-(2H-1,3-benzodioxol-5-yl)-4-(2-hydroxyphenyl)-3-methyl-1-phenyl-1H-pyrazolo[3,4-b]pyridine-5-carbonitrile (36)

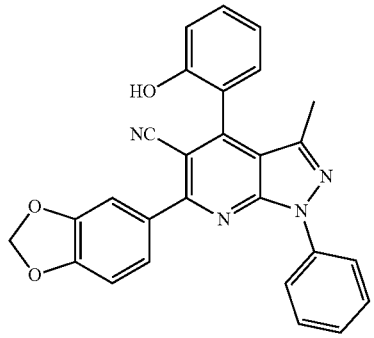 [SMILES: Cc1nn(-c2ccccc2)c2nc(-c3ccc4c(c3)OCO4)c(C#N)c(-c3ccccc3O)c12]

Synthesized from 3-(2H-1,3-benzodioxol-5-yl)-3-oxopropanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with methanol to yield the final product as an off-white powder (87 mg, 20%), m.p. 240-242° C., HRMS (ESI) m/z calculated for $C_{27}H_{18}N_4O_3$ [M+H]$^+$ 447.1457, found 447.1452.

$^1$H NMR (CDCl$_3$, 400 MHz): δ=2.20 (s, 3H), 6.08 (m, 3H, CH$_2$(O)$_2$ & OH), 6.96 (m, 2H), 7.14 (m, 1H), 7.34 (m, 2H), 7.42 (m, 1H), 7.55 (m, 4H), 8.26 (d, J=7.6 Hz, 2H).

$^{13}$C NMR (CDC$_3$, 75 MHz): δ=13.7, 101.6, 101.9, 108.3, 109.9, 114.1, 116.4, 117.8, 120.9, 121.1, 121.3, 124.4, 126.4, 129.2, 130.4, 131.7, 131.9, 138.7, 144.4, 148.0, 149.5, 149.6, 150.2, 152.8, 160.0.

4-(2-hydroxyphenyl)-6-(4-methanesulfonylphenyl)-3-methyl-1-phenyl-1H-pyrazolo[3,4-b]pyridine-5-carbonitrile (37)

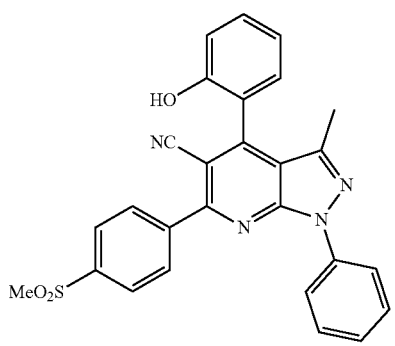 [SMILES: Cc1nn(-c2ccccc2)c2nc(-c3ccc(S(C)(=O)=O)cc3)c(C#N)c(-c3ccccc3O)c12]

Synthesized from 3-(4-methanesulfonylphenyl)-3-oxopropanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with ethyl acetate to yield the final product as a fine white powder (77 mg, 16%), m.p. 222-224° C., HRMS (ESI) m/z calculated for $C_{27}H_2N_4O_3S$ [M+H]$^+$ 481.1334, found 481.1333.

$^1$H NMR (CDCl$_3$, 400 MHz): δ=2.26 (s, 3H), 3.15 (s, 3H), 7.06 (d, J=7.1 Hz, 1H), 7.2 (t, J=7.5 Hz, 1H), 7.34-7.40 (m, 2H), 7.47-7.59 (m, 3H), 8.12-8.17 (m, 2H), 8.20-8.31 (m, 4H).

$^{13}$C NMR (CDCl$_3$, 101 MHz): δ=13.7, 44.5, 102.3, 114.9, 116.4, 117.0, 120.9, 121.3, 121.4, 126.6, 127.6, 129.2, 130.4, 130.6, 131.9, 138.7, 141.8, 143.0, 144.4, 149.4, 150.1, 152.5, 158.3.

4-(2-hydroxyphenyl)-3-methyl-1-phenyl-6-(5,6,7,8-tetrahydronaphthalen-2-yl)-1H-pyrazolo[3,4-b]pyridine-5-carbonitrile (38)

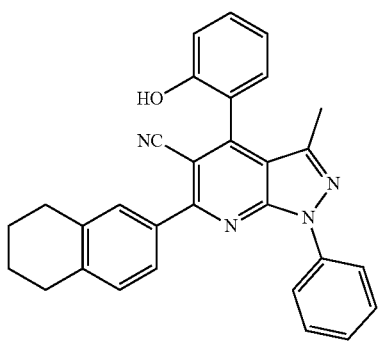 [SMILES: Cc1nn(-c2ccccc2)c2nc(-c3ccc4c(c3)CCCC4)c(C#N)c(-c3ccccc3O)c12]

Synthesized from 3-oxo-3-(5,6,7,8-tetrahydronaphthalen-2-yl)propanenitrile, 5-amino-3-methyl-1-phenylpyrazole and 2-hydroxybenzaldehyde on a 1 mmol scale according to the general procedure for the synthesis of pyrazolo[3,4-b] pyridines. The crude product was purified via trituration with methanol to yield the final product as a light brown powder (58 mg, 13%), m.p. 236-238° C., HRMS (ESI) m/z calculated for $C_3H_{24}N_4O$ [M+H]+ 457.2028, found 457.2034.

$^1$H NMR (CDCl$_3$, 400 MHz): δ=1.54 (s, 1H), 1.87 (m, 4H), 2.21 (s, 3H), 2.89 (m, 4H), 7.03 (d, 1H J=8.0 Hz,), 7.17 (s, 1H), 7.23 (d, 1H, J=8.0 Hz), 7.36 (t, 2H, J=7.6 Hz), 7.46 (s, 1H), 7.52 (t, 2H, J=8.0 Hz), 7.73 (d, 2H, J=12 Hz), 8.32 (d, 2H, J=8.0 Hz).

$^{13}$C NMR (CDC$_3$, 101 MHz): δ=13.3, 22.7, 22.8, 29.1, 29.2, 102.0, 113.8, 116.1, 117.3, 120.9, 121.0, 125.9, 126.3, 128.8, 129.0, 129.0, 130.0, 130.1, 131.3, 134.9, 137.1, 138.7, 139.4, 143.9, 148.5, 150.1, 152.3, 160.7.

6-(2,3-dihydro-1,4-benzodioxin-6-yl)-4-(2-hydroxyphenyl)-3-methyl-1-phenyl-1H-pyrazolo[3,4-b]pyridine-5-carbonitrile (39)

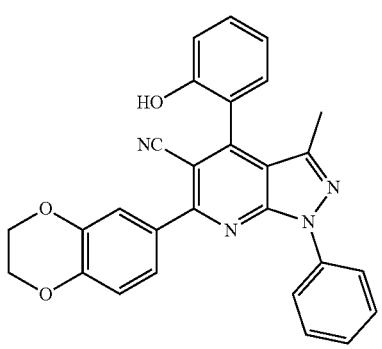 [SMILES: Cc1nn(-c2ccccc2)c2nc(-c3ccc4c(c3)OCCO4)c(C#N)c(-c3ccccc3O)c12]

Synthesized from 3-(2,3-dihydro-1,4-benzodioxin-6-yl)-3-oxopropanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via reverse-phase HPLC using a 35:65 water/acetonitrile eluent (0.1% TFA) to yield the final product as an off-white powder (30 mg, 7%), m.p. 293-294° C., HRMS (ESI) m/z calculated for $C_{28}H_{20}N_4O_3$ [M+H]+ 461.1613, found 461.1611.

$^1$H NMR (CDCl$_3$, 400 MHz): δ=2.12 (s, 3H), 4.34 (s, 4H), 7.07 (m, 3H), 7.43 (m, 5H), 7.59 (t, J=8.0 Hz, 2H), 8.22 (d, J=7.6 Hz, 2H), 10.03 (s, 1H).

$^{13}$C NMR (DMSO-d$_6$, 101 MHz): δ=13.7, 64.6, 64.9, 102.3, 114.3, 116.5, 117.6, 117.9, 118.6, 119.6, 121.3, 121.5, 123.1, 126.9, 129.7, 130.7, 131.2, 131.9, 138.9, 143.7, 144.6, 145.9, 150.1, 150.9, 154.9, 159.7.

6-[3-bromo-4-(morpholin-4-yl)phenyl]-4-(2-hydroxyphenyl)-3-methyl-1-phenyl-1H-pyrazolo[3,4-b]pyridine-5-carbonitrile (40)

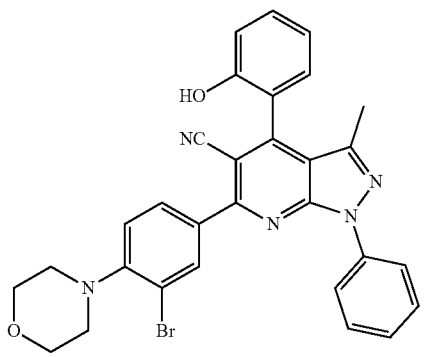 [SMILES: Cc1nn(-c2ccccc2)c2nc(-c3ccc(N4CCOCC4)c(Br)c3)c(C#N)c(-c3ccccc3O)c12]

Synthesized from 3-[3-bromo-4-(morpholin-4-yl)phenyl]-3-oxopropanenitrile, 5-amino-3-methyl-1-phenylpyrazole and 2-hydroxybenzaldehyde on a 1 mmol scale according to the general procedure for the synthesis of pyrazolo[3,4-b]pyridines. The crude product was purified via trituration with methanol to yield the final product as a beige powder (149 mg, 26%), decomposes at 268° C., HRMS (ESI) m/z calculated for $C_{30}H_{24}BrN_5O_2$ [M+H]$^+$ 566.1191, found 566.1181.

$^1$H NMR (CDCl$_3$, 400 MHz): δ=2.13 (s, 3H), 3.11 (m, 4H), 3.8 (m, 4H), 7.07 (m, 2H), 7.45 (m, 4H), 7.6 (t, J=7.9 Hz, 2H), 7.98 (dd, J=8.3 Hz, 1H), 8.2 (m, 3H), 10.05 (s, 1H).

$^{13}$C NMR (DMSO-d$_6$, 101 MHz): δ=13.7, 51.9, 66.8, 102.4, 114.5, 116.5, 117.9, 118.5, 119.6, 121.2, 121.5, 121.6, 126.9, 129.7, 130.3, 130.7, 132.0, 134.0, 134.8, 138.8, 144.6, 150.0, 150.9, 152.1, 155.0, 158.5.

6-(3-ethylphenyl)-4-(2-hydroxyphenyl)-3-methyl-1-phenyl-1H-pyrazolo[3,4-b]pyridine-5-carbonitrile (41)

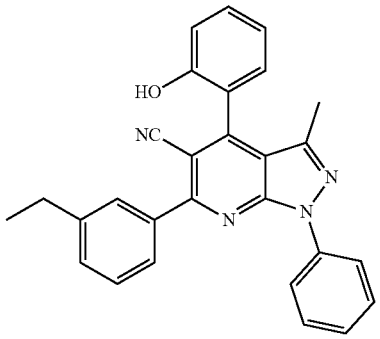 [SMILES: CCc1cccc(-c2nc3c(c(C)nn3-c3ccccc3)c(-c3ccccc3O)c2C#N)c1]

Synthesized from 3-(3-ethylphenyl)-3-oxopropanenitrile, 5-amino-3-methyl-1-phenylpyrazole and 2-hydroxybenzaldehyde on a 0.87 mmol scale according to the general procedure for the synthesis of pyrazolo[3,4-b]pyridines. The crude product was purified via reverse-phase HPLC using a 50-95% acetonitrile gradient in water (0.1% TFA) to yield the final product as a fine yellow powder (126 mg, 33%), m.p. 178-179° C., HRMS (ESI) m/z calculated for $C_{28}H_{22}N_4O$ [M+H]$^+$ 431.1872, found 431.1865.

$^1$H NMR (CDCl$_3$, 400 MHz): δ=1.32 (t, J=7.6 Hz, 3H), 2.22 (s, 3H), 2.78 (q, J=7.7 Hz, 2H), 7.00 (d, J=8.2 Hz, 1H), 7.14-7.18 (m, 1H), 7.31-7.39 (m, 3H), 7.43-7.47 (m, 2H), 7.49-7.54 (m, 2H), 7.82-7.85 (m, 2H), 8.31 (d, J=8.2 Hz, 2H).

$^{13}$C NMR (CDCl$_3$, 101 MHz): δ=13.6, 15.4, 28.8, 102.2, 114.2, 116.4, 120.7, 121.1, 121.4, 126.4, 126.9, 128.5, 129.1, 129.1, 129.8, 130.3, 131.6, 137.9, 138.7, 144.4, 144.5, 149.8, 149.8, 150.3, 153.1, 161.1.

6-(4-ethylphenyl)-4-(2-hydroxyphenyl)-1,3-diphenyl-1H-pyrazolo[3,4-b]pyridine-5-carbonitrile (42)

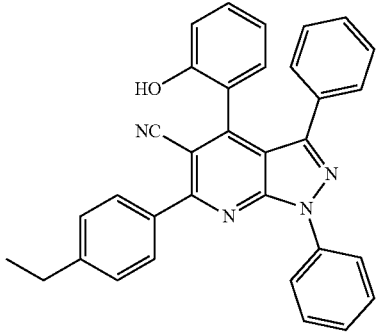 [SMILES: CCc1ccc(-c2nc3c(c(-c4ccccc4)nn3-c3ccccc3)c(-c3ccccc3O)c2C#N)cc1]

Synthesized from 3-(4-ethylphenyl)-3-oxopropanenitrile, 1,3-diphenyl-1H-pyrazol-5-amine and 2-hydroxybenzaldehyde on a 1 mmol scale according to the general procedure for the synthesis of pyrazolo[3,4-b]pyridines. The crude product was purified via reverse-phase HPLC using a 50-95% acetonitrile gradient in water (0.1% TFA) to yield the final product as an off-white powder (85 mg, 17%), m.p. 248-249° C., HRMS (ESI) m/z calculated for $C_{33}H_{24}N_4O$ [M+H]$^+$ 493.2028, found 493.2027.

¹H NMR (CDCl₃, 400 MHz): δ=1.27 (m, 3H), 2.74 (d, J=7.6 Hz, 2H), 6.74 (m, 2H), 7.2 (m, 7H), 7.45 (m, 3H), 7.64 (m, 2H), 7.92, (d, J=8.3 Hz, 2H), 8.31 (d, J=7.5 Hz, 2H), 9.83 (s, 1H).
¹³C NMR (DMSO-d₆, 101 MHz): δ=15.8, 28.5, 103.5, 113.0, 116.1, 118.0, 119.2, 121.7, 122.2, 127.4, 127.9, 128.4, 128.7, 129.0, 129.8, 129.9, 130.7, 131.6, 131.7, 135.6, 138.8, 146.7, 147.7, 150.4, 151.1, 155.0, 160.6.

3-cyclopropyl-6-(4-ethylphenyl)-4-(2-hydroxyphenyl)-1-phenyl-1H-pyrazolo[3,4-b]pyridine-5-carbonitrile (43)

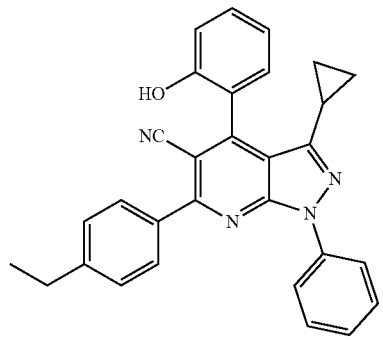 [SMILES: CCc1ccc(-c2nc3c(c(C4CC4)nn3-c3ccccc3)c(-c3ccccc3O)c2C#N)cc1]

Synthesized from 3-(4-ethylphenyl)-3-oxopropanenitrile, 3-cyclopropyl-1-phenyl-1H-pyrazol-5-amine and 2-hydroxybenzaldehyde on a 1 mmol scale according to the general procedure for the synthesis of pyrazolo[3,4-b]pyridines. The crude product was purified via reverse-phase HPLC using a 75:25 acetonitrile/water eluent (0.1% TFA) to yield the final product as a light brown powder (78 mg, 6%), m.p. 122-124° C., HRMS (ESI) m/z calculated for $C_{30}H_{24}N_4O$ [M+H]⁺ 457.2028, found 457.2028.
¹H NMR (CDCl₃, 400 MHz): δ=0.72 (m, 2H), 1.01 (m, 1H), 1.10 (m, 1H), 1.32 (t, J=7.6 Hz, 3H), 1.51 (m, 1H), 2.76 (q, J=7.6 Hz, 2H), 7.02 (d, J=8.1 Hz, 1H), 7.16 (t, J=7.6 Hz, 1H), 7.30 (t, J=7.4 Hz, 1H), 7.40 (m, 4H), 7.51 (t, J=7.6 Hz, 2H), 7.98 (d, J=8.0 Hz, 2H), 8.31 (d, J=8.0 Hz, 2H).
¹³C NMR (DMSO-d₆, 101 MHz): δ=7.8, 8.2, 15.3, 28.0, 102.1, 114.1, 115.8, 117.5, 119.0, 120.9, 121.0, 126.3, 127.9, 129.2, 129.3, 130.2, 131.3, 135.2, 138.4, 146.1, 149.1, 149.7, 150.4, 154.5, 160.0.

6-(4-ethylphenyl)-4-(2-hydroxyphenyl)-3-methyl-1-(2-methylphenyl)-1H-pyrazolo[3,4-b]pyridine-5-carbonitrile (44)

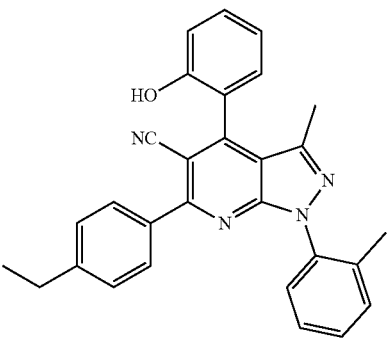 [SMILES: CCc1ccc(-c2nc3c(c(C)nn3-c3ccccc3C)c(-c3ccccc3O)c2C#N)cc1]

Synthesized from 3-(4-ethylphenyl)-3-oxopropanenitrile, 3-methyl-1-(2-methylphenyl)-1H-pyrazol-5-amine and 2-hydroxybenzaldehyde on a 1 mmol scale according to the general procedure for the synthesis of pyrazolo[3,4-b]pyridines. The crude product was purified via trituration with methanol to yield the final product as an off-white powder (141 mg, 32%), m.p. 311-313° C., HRMS (ESI) m/z calculated for $C_{29}H_{24}N_4O$ [M+H]⁺ 445.2028, found 445.2024.
¹H NMR (CDC₃, 400 MHz): δ=1.22 (t, J=7.6 Hz, 3H), 2.16 (m, 6H), 2.68 (q, J=7.5 Hz, 2H), 7.05 (t, J=7.4 Hz, 1H), 7.13 (s, 1H), 7.43 (m, 8H), 7.74 (d, J=8.1 Hz, 2H), 10.04 (s, 1H).
¹³C NMR (DMSO-d₆, 101 MHz): δ=13.7, 15.7, 18.4, 28.5, 102.1, 113.0, 116.5, 118.1, 119.6, 121.5, 127.1, 128.2, 129.5, 129.7, 130.8, 131.5, 131.8, 135.4, 135.7, 137.0, 144.0, 146.4, 150.8, 151.1, 155.0, 160.6.

6-(4-ethylphenyl)-4-(2-hydroxyphenyl)-3-methyl-1-(3-methylphenyl)-1H-pyrazolo[3,4-b]pyridine-5-carbonitrile (45)

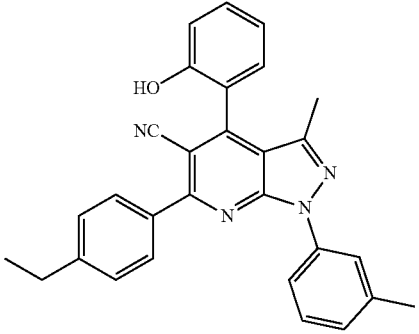 [SMILES: CCc1ccc(-c2nc3c(c(C)nn3-c3cccc(C)c3)c(-c3ccccc3O)c2C#N)cc1]

Synthesized from 3-(4-ethylphenyl)-3-oxopropanenitrile, 3-methyl-1-(3-methylphenyl)-1H-pyrazol-5-amine and 2-hydroxybenzaldehyde on a 1 mmol scale according to the general procedure for the synthesis of pyrazolo[3,4-b]pyridines. The crude product was purified via trituration with methanol to yield the final product as an off-white powder (52 mg, 11%), m.p. 235-237° C., HRMS (ESI) m/z calculated for $C_{29}H_{24}N_4O$ [M+H]⁺ 445.2028, found 445.2023.
¹H NMR (CDCl₃, 400 MHz): δ=1.26 (t, J=7.6 Hz, 3H), 2.12 (s, 3H), 2.41 (s, 3H), 2.73 (q, J=7.5 Hz, 2H), 7.04 (m, 1H), 7.11 (d, J=8.1 Hz, 1H), 7.18 (d, J=7.5 Hz, 1H), 7.44 (m, 5H), 7.89 (d, J=7.9 Hz, 2H), 8.01 (s, 1H), 8.09 (d, J=8.1 Hz, 1H), 10.02 (s, 1H).
¹³C NMR (DMSO-d₆, 101 MHz): δ=13.7, 15.8, 21.7, 28.5, 102.4, 114.3, 116.4, 118.0, 118.6, 119.6, 121.2, 121.9, 127.5, 128.4, 129.5, 129.8, 130.7, 131.9, 135.7, 138.8, 139.2, 144.5, 146.6, 150.1, 150.9, 154.9, 160.4.

6-(4-ethylphenyl)-4-(2-hydroxyphenyl)-3-methyl-1-(4-methylphenyl)-1H-pyrazolo[3,4-b]pyridine-5-carbonitrile (46)

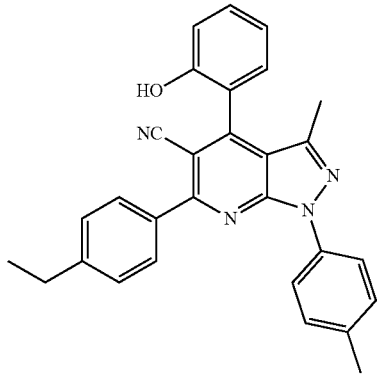 [SMILES: CCc1ccc(-c2nc3c(c(C)nn3-c3ccc(C)cc3)c(-c3ccccc3O)c2C#N)cc1]

Synthesized from 3-(4-ethylphenyl)-3-oxopropanenitrile, 3-methyl-1-(4-methylphenyl)-1H-pyrazol-5-amine and 2-hydroxybenzaldehyde on a 1 mmol scale according to the general procedure for the synthesis of pyrazolo[3,4-b]pyridines. The crude product was purified via trituration with methanol to yield the final product as an light brown powder (43 mg, 10%), m.p. 120-122° C., HRMS (ESI) m/z calculated for $C_{29}H_{24}N_4O$ [M+H]$^+$ 445.2028, found 445.2024.

$^1$H NMR (CDCl$_3$, 400 MHz): δ=1.32 (t, J=7.6 Hz, 3H), 2.20 (s, 3H), 2.42 (s, 3H), 2.76 (q, J=7.6 Hz, 2H), 7.02 (d, J=8.0 Hz, 1H), 7.16 (t, J=7.6 Hz, 1H), 7.35 (m, 5H), 7.46 (t, J=7.6 Hz, 1H), 7.96 (d, J=8.0 Hz, 2H), 8.15 (d, J=8.0 Hz, 2H).

$^{13}$C NMR (DMSO-d$_6$, 101 MHz): δ=13.6, 15.3, 21.0, 28.8, 102.0, 113.9, 116.4, 117.9, 120.9, 121.2, 121.3, 128.0, 129.6, 129.7, 130.4, 131.6, 135.4, 136.1, 136.4, 144.0, 146.6, 149.4, 150.2, 152.9, 160.6.

Biological Assays

3D7 Parasite Growth-Inhibition Assay

Asynchronous parasites were maintained in culture based on the method of Trager and Jensen. All synthesized inhibitors were tested against the chloroquine sensitive *Plasmodium falciparum* strain 3D7 (MRA-102) provided by the MR4 Unit of the American Type Culture Collection (ATCC, Manassas, Va.). Parasites were grown in the presence of fresh group 0-positive erythrocytes (Key Biologics, LLC, Memphis, Tenn.) in petri dishes at a hematocrit of 4-6% in complete RPMI 1640 supplemented with 0.5% AlbuMAX II (Life Technologies). Cultures were incubated at 37° C. in a gas mixture of 90% N$_2$, 5% O$_2$, and 5% CO$_2$. For EC$_{50}$ determinations, 20 μL of RPMI 1640 with 5 μg/mL gentamicin were dispensed per well in a 384-well assay plate (product number 8807BC; Corning). Test articles were prepared as stock solutions in DMSO. Drug plates were prepared by serially diluting (ten, 3-fold dilutions) stock solutions into a 384-well clear polypropylene plate (Corning, 3657). Test articles were manually transferred (73 nL) from the drug plate to the assay plate by hydrodynamic pin transfer using a pin tool (AFIX384FP1, V&P Scientific) adapted for manual transfer (BGPK, VP 381D-N, V&P Scientific) and equipped with FP1S50 pins (V&P Scientific). Next, 20 μL of a synchronized culture suspension (1% rings and 4% hematocrit) was added per well, resulting in a final hematocrit and parasitemia of 2% and 1%, respectively. Assay plates were incubated for 72 h, and the parasitemia was determined as previously described. Briefly, 10 μL of the following solution in phosphate-buffered saline (PBS) was added per well: 10× SYBR green I, 0.5% Triton X-100 [vol/vol], 0.5 mg/mL saponin. Assay plates were shaken for 1 min, incubated in the dark for 90 min. Fluorescence was measured on a Clariostar plate reader (BMG Labtech) at excitation/emission wavelengths of 485 nm/535 nm. Assay endpoints were normalized from 0% (DMSO only) to 100% inhibition (16 μM Mefloquine) and fit to a semi-log plot using n=5 replicates. The curve fit and EC50 values were determined using the Collaborative Drug Discovery software and standard Hill equation.

BJ Mammalian Cell Proliferation Assay

The BJ cell line was purchased from the American Type Culture Collection (ATCC, Manassas, Va.) and cultured according to recommendations. Cell culture media was purchased from ATCC. Cells were routinely tested for *mycoplasma* contamination using the MycoAlert *Mycoplasma* Detection Kit (Lonza). Exponentially growing cells were plated in 384-well polystyrene, white, flat bottom, low flange, tissue culture treated assay plates (Corning, 3570) using a Matrix Wellmate liquid dispenser (Thermo Fisher), and incubated overnight at 37° C. in a humidified 5% CO$_2$ incubator. Each cell line was plated to a previously validated density to ensure logarithmic growth. For BJ, the cells were plated to 1000/cells per well in 30 microliters of complete media. Test articles were prepared as stock solutions in DMSO. Drug plates were prepared by serially diluting (ten, 3-fold dilutions) stock solutions into a 384-well clear polypropylene plate (Corning, 3657). Test articles were manually transferred (73 nL) from the drug plate to the assay plate by hydrodynamic pin transfer using a pin tool (AFIX384FP1, V&P Scientific) adapted for manual transfer (BGPK, VP 381D-N, V&P Scientific) and equipped with FP1S50 pins (V&P Scientific). After drugging, the plates were incubated at 37° C. in a humidified 5% CO$_2$ incubator for 72 hours, and then cell viability was measured using Cell TiterGlo (Promega, G7573) according to the manufacturer's recommendation. Luminescence was measured on a Clariostar plate reader (BMG Labtech). Assay endpoints were normalized from 0% (DMSO only) to 100% inhibition (58 μM Idarubicin) and fit to a semi-log plot using n=6 replicates. The curve fit and EC$_{50}$ values were determined using the Collaborative Drug Discovery software and standard Hill equation.

FACS Killing Rate Assay

The IC$_{50}$ of the drug were first determined using a previously reported 48 h $^3$H-hypoxanthine incorporation assay. Briefly, a culture of parasitized erythrocytes of strain 3D7 (Malaria Research and Reference Reagent Resource Center MR4) with a 0.5% parasitemia and 2% hematocrit (≥80% ring-stage population) in a media containing RPMI-1640 (Sigma, 25 mM HEPES and NaHCO$_3$) supplemented with 2% D-sucrose (Merck), 0.3% L-glutamine (Merck), 5 g/L AlbuMAX II (Gibco) solution and 5 μM hypoxanthine (Fluka) is exposed to 3-fold serial dilutions of compounds. Plates were incubated 48 h at 37° C. in 5% CO$_2$, 5% O$_2$ and 90% N$_2$. After 24 h of incubation, $^3$H-hypoxanthine is added and the plates are incubated for another 24 h. The plates were then harvested on a glass fiber filter (TOMTEC Cell harvester 96). Filters are dried and melt-on scintillator sheets were used to determine the incorporation of $^3$H-hypoxanthine. Radioactivity is measured using a microbeta counter, with two replicates measured for each compound. Data were normalized using the incorporation of the positive control (parasitized red blood cells with no drug). IC$_{50}$ was calculated using Microsoft Excel and Grafit software.

The parasite killing profile is estimated by culturing unlabeled erythrocytes infected with the 3D7 strain in the presence of the tested compound at a concentration corresponding to 10× the $IC_{50}$ determined previously using the 48 h $^3$H-hypoxanthine incorporation assay. Parasites are drug treated for 24 and 48 h. Tested compounds are renewed after the first 24 h of treatment by taking out old media and replenishing with new culture media with fresh drug. After treatment, the compound is removed and the culture is diluted (⅓$^{rd}$ dilution) using fresh erythrocytes (2% hematocrit) previously labeled with CFDA-SE (carboxyfluorescein diacetate succinimidyl ester, Life Technologies). CFDA-SE labeled erythrocytes can be prepared by incubating a 1% hematocrit in RPMI 1640 media with 10 μM CFDA-SE at 37° C. for 30 minutes, then washing the cells twice with media and maintained at 50% hematocrit at 4° C. for up to 24 h before use. Following a further 48 h incubation in standard conditions, the ability of treated parasites to establish new infections in fresh, labeled erythrocytes is detected by quantification of double stained erythrocytes using two-color flow cytometry (Attune N×T Flow Cytometer, ThermoFisher) after labeling of parasite DNA with Hoescht 33342 (Sigma). The Hoescht 33342 is excited by a laser at 405 nm and detected by a 440/50 filter (VL1). CFDA-SE is excited by a blue laser 488 nm and detected by a 530/30 filter. Samples were analyzed using the Attune N×T software package. Parasite viability is shown as the percentage of infected CFDA-SE stained erythrocytes in drug treated samples at 24 or 48 h, using labeled erythrocytes and labeling of parasite DNA from untreated cultures as a control. Chloroquine, pyrimethamine, atovaquone and artesunate are used in each assay to validate the assay and allow for comparative classification on the killing rate of the tested compound.

*Plasmodium falciparum*: Male/Female Gamete Formation Assay

Asexual cultures of *P. falciparum* 3D7 parasites were used to seed gametocyte cultures at 1% parasitemia and 4% hematocrit as previously described. Culture medium (RPMI medium with 25 mM HEPES, 50 mg/L hypoxanthine, 2 g/L sodium bicarbonate and 10% human serum) was replaced daily for at least 14 day with all solutions, pipettes and work surfaces treated at 37° C. Typical cultures follow the pattern of asexual parasitemia rising to a peak and crashing at days 4-5, with stage II gametocytes visible at day 7, stage III visible at day 9, stage IV visible at day 11, and stage V visible at day 14 with high levels of exflagellation.

To detect males, sterile 1.5 mL tubes containing 150 μL of culture medium and each tested compound (1 μM as a DMSO solution with a maximum concentration of 0.5% DMSO overall) and a control (0.5% DMSO only) were pre-warmed to 37° C. in a heater block. While these tubes are warming, cells in the gametocyte culture were left to settle until the cells had settled on the bottom of the flask, then half off the culture medium was removed to concentrate the cells, then the cells were resuspended. 50 μL of this cell suspension was quickly added to each assay tube. These tubes were quickly gassed with a mixture of 3% $O_2$, 5% $CO_2$ and 92% $N_2$, sealed, and placed into an incubator at 37° C. After the incubation period, the tubes were removed in small groups of no more than 7 at a time and assessed. The assay should always be performed in small batches due to the time-dependent nature of exflagellation. Exflagellation was tested by extracting a 200 μL sample of culture and briefly centrifuging the cells. The pellet was then resuspended in 10 μL a RPMI medium with 25 mM HEPES, 50 mg/L hypoxantine, 2 g/L sodium bicarbonate, 100 μM xanthurenic acid and 20% human serum, then introduced into the chamber of a disposable hemocytometer slide (Immune Systems). After 20 minutes, exflagellation was observed at 10× magnification in a single random field of view using a 5 second time lapse captured at 4 frames per second. An algorithm was then used to compare the frames using ImageJ to identify which cells moved, indicating exflagellation centers detected over time. This was repeated with five samples across three independent cultures, with the data normalized to account for differing absolute exflagellation levels between cultures before being compared.

To detect females, the gametocyte cultures were prepared as previously described above, with the exception that day 16 cultures were used due to the slightly slower development of females in culture. The 4B7 anti-Pfs25 antibody (MR4) was coupled to Cy3 by use of an Amersham CyDye monoclonal antibody labeling kit (GE Healthcare) according to the manufacturer's instructions. The labeled antibody was used at a 1:500 dilution of a 0.5 mg/mL IgG stock solution. 48 h after staining an ImageJ algorithm was used to count fluorescent cells using the particle counter function.

To determine $EC_{50}$ values, the number of exflagellation centers per field, mean oocyst intensity and prevalence of infection were normalized to the respective DMSO treated control and % inhibition calculated. Tested compounds were prepared as a DMSO solutions from 25 μM to 0.026 μM across 22 points. Percentage inhibition data obtained from each individual parameter was fitted to a four-parameter logistic equation with variable slope using GraphPad Prism 6.07 for which compound concentrations were first transformed to their respective $log_{10}$ values. The data were then fitted using these transformed values without defining constraints. The $IC_{50}$ values were then calculated from the anti-log of the x values corresponding to the 50% inhibition obtained.

*Plasmodium Berghei* Luciferase Liver Stage Bioluminescence Assay

*P. berghei* luciferase sporozoites were obtained by dissection of infected *A. stephensi* mosquito salivary glands supplied by the New York University Insectary as previously described (Swann, et al.), with the sporozoites kept on ice until needed. *P. berghei* was used due to the fact that it has higher infection rates against HepG2 cells expressing the CD81 receptor, making it more receptive to screening assays. HepG2-A16-CD81EGFP cells which were stably transformed to express a GFP-CD81 fusion protein were cultured at 37° C. and 5% $CO_2$ in DMEM supplemented with 10% FBS, 0.29 mg/mL glutamine, 100 units penicillin and 100 μg/mL of streptomycin (Invitrogen, Carlsbad, USA). HepG2-A16-CD81EGFP cells (3×10$^3$) in 5 μL of medium (2×10$^5$ cells/mL, 5% FBS, 5× penicillin/streptomycin/glutamine) were seeded into 1536-well, white, solid-bottom plates (Greiner Bio-One) 20-26 h prior to infection. 50 nL of compound in DMSO (0.5% final DMSO concentration per well) was transferred with an Acoustic Transfer System (Biosero) in to the assay plates (50 μM final concentration) 18 h prior to infection. Atovaquone (12-point serial dilution starting at 0.25 μM) and 0.5% DMSO were used as positive and negative controls, respectively. Freshly dissected *P. berghei* luciferase sporozoites were re-suspended in media and their concentration adjusted to 200 sporozoites/μL. Penicillin, glutamine and streptomycin were also added at 5× concentration for a final 5×-fold concentration in the well (the increased antibiotic concentration does not interfere with parasite or HepG2 cell growth). The HepG2-A16-CD81EGFP cells were then infected with 1×10$^3$ sporozoites per well (5 μL) using a single tip bottle valve liquid handler (GNF), and the plates were centrifuged for 3 min. at room temperature and at 330 g (Eppendorf 5810 R) on normal acceleration and brake setting. The plates were then incubated at 37° C. for 48 h in 5% $CO_2$ with high humidity to minimize age effect caused by evaporation of the media. After incubation, the plates were assessed by testing the luciferase expression. This was done by removing the media by spinning the inverted plates at 150 g for 1 minute. 2 µL of BrightGlo (Promega) was dispensed with the MicroFlo liquid handler (BioTek) into the emptied 1536 wells. The plates were held for at least 2 minutes with the Bright-Glo reagent in the wells (per manufacturer instructions) for the process to occur. The plates were then loaded and read by an EnVision Multilabel plate reader (PerkinElmer) using a luminescence protocol. $IC_{50}$ values were obtained using measured bioluminescence intensity and a non-linear variable slope protocol in CDD Vault, an online collaborative drug discovery informatics program.

HepG2 Cytotoxicity Bioluminescence Assay

HepG2-A16-CD81EGFP cells which were stably transformed to express a GFP-CD81 fusion protein were cultured at 37° C. and 5% $CO_2$ in DMEM supplemented with 10% FBS, 0.29 mg/mL glutamine, 100 units penicillin and 100 µg/mL of streptomycin (Invitrogen, Carlsbad, USA). HepG2-A16-CD81EGFP cells ($3\times10^3$) in 5 µL of medium ($2\times10^5$ cells/mL, 5% FBS, 5× penicillin/streptomycin/glutamine) were seeded into 1536-well, white, solid-bottom plates (Greiner Bio-One) 20-26 h prior to compound addition. 50 nL of compound in DMSO (0.5% final DMSO concentration per well) was transferred with an Acoustic Transfer System (Biosero) in to the assay plates (50 µM final concentration). Puromycin (12-point serial dilution starting at 25 µM) and 0.5% DMSO were used as positive and negative controls, respectively. The plates were then incubated at 37° C. for 48 h in 5% $CO_2$ with high humidity. The HepG2-A16-CD81EGFP cells were not infected with $1\times10^3$ sporozoites per well (5 µL) such as in the *P. berghei* bioluminescence assay. To maintain similar conditions, the 5 µL additional volume was accomplished by using the same screening media with no infected sporozoites. No centrifugation was performed using only the media addition. The plates were then incubated at 37° C. for 48 h in 5% $CO_2$ with high humidity to minimize age effect caused by evaporation of the media. The HepG2 cytotoxicity was assessed to determine the number of viable cells in culture based on quantitation of the ATP present, which signals the presence of metabolically active cells. This was achieved by removing the media by spinning the inverted plates at 150 g for 1 minute followed by the addition of 2 µL of CellTiterGlo (Promega) diluted 1:2 with deionized water into the emptied 1536 wells, using the MicroFlo liquid handler (BioTek). Immediately after the addition of the CellTiterGlo, the plates were read by an EnVision Multilabel plate reader (PerkinElmer) using a luminescence protocol. $IC_{50}$ values were obtained using measured bioluminescence intensity and a non-linear variable slope protocol in CDD Vault, an online collaborative drug discovery informatics program.

Solubility Assay

Compound solubility was determined by UV-Vis spectrophotometry as follows: A stock solution of each compound was prepared in DMSO to a final concentration of 10 mM. Each compound was diluted to final concentrations of 50 µM, 75 µM, 100 µM and 150 µM on a UV-transparent 96-well microplate in 50% (v/v) DMSO and 50% (v/v) 1×PBS, pH 7.4. Each concentration was plated in triplicate. The absorbance spectra were measured from 200-550 nm on a SpectraMax $M2^e$ Microplate Reader (Molecular Devices) or xMark™ Microplate Absorbance Spectrophotometer (Bio-Rad). The molar extinction coefficient at lambda max for each compound was determined using the Beer-Lambert law. Solubility was determined by combining 6 µL of 10 mM stock compound with 594 µL 1×PBS, pH 7.4 in a 2 mL screw-cap microfuge tube with an O-ring (100 µM final compound concentration). Samples were stored sealed at room temperature for 18 hours. Next, 150 µL aliquots were added, in triplicate, to a 0.2 µm AcroPrep™ Advance 96-Well Filter Plate (PALL) and centrifuged at 1,500×g for 3 minutes at 25° C. Next, 75 µL of filtrate was mixed with 75 µL of DMSO on a UV-transparent 96-well microplate and absorbance measured from 200-550 nm. Absorbance at lambda max for each measurement was corrected for Rayleigh scattering by linear extrapolation of baseline absorbance and compound solubility in the filtrate was reported as the average ±standard deviation.

General Methods $^1H$ and $^{13}C$ Nuclear Magnetic Resonance (NMR) spectra were obtained on a 300 or 400 MHz instrument using $CDCl_3$, DMSO-$d_6$ or acetone-$d_6$ as the solvent. Chemical shifts were reported as δ values in parts per million (ppm) relative to the solvent. All reactions were performed open to the atmosphere unless indicated otherwise. Analytical thin layer chromatography (TLC) was performed on aluminum-backed 250 µm layer silica plates visualized with either 254 or 365 nm wavelengths. Sonication was performed in an Ultrasonic Cleaner GB928. All solvents were used without purification and no attempts were made to exclude atmospheric moisture. Glassware was dried for at least 1 h in a 90° C. oven prior to use. All reported yields are isolated yields. Frontrunner compounds (10, 17 & 27) were assayed to confirm=95% purity as determined using an HPLC system consisting of a Shimadzu Prominence UFLC with LC-20ADXR pumps, SIL-20AXR autosampler, CTO-20AC column oven, and SPD-M20A DAD detector. All HRMS samples were prepared at 1 mg/mL in MeOH, then diluted 1:20 in MeOH for testing with 2 µL injection volume and mass was detected with an ABSciex TripleTOF 5600+ with CDS (Calibrant Delivery System) and DuoSpray Ion Source.

Binding Energy Computations

After completion of the production runs, binding energies were estimated using the MMPBSA.py module of AmberTools18.[31] The simulations used the single trajectory method, and binding energies were calculated using the MM/PBSA and MM/GBSA algorithms.[22] The PBSA simulation used ionic strength of 0.15 mM (istrng=0.150) and employed default radii from the prmtop file (radiopt=0). The GBSA simulation used generalized Born Method two (igb=5) with 0.15 M salt concentration. Binding energy values were determined over the final 20-ps sample of each 50-ns trajectory.

Example 1: Pyrazolo[3,4-b]Pyridines Display Antimalarial Activity

Results suggest that they display comparable activity against drug resistant strains while simultaneously displaying no cytotoxicity against a human cell line. t should be noted that the pyrazolopyridine core itself has been reported to have antimalarial activity in a prior publication, but it was only utilized as a replacement core for chloroquine and only targeting the asexual blood stage of *Plasmodium*.[10] It also appears that phenol hydroxyl group is important to activity, as well as substitution about the phenyl ring at the 2-pyridine position. A library of compounds related to 1 was created to better understand not only these moieties, but also to probe modifications about the pyrazole ring as well. Three series of compounds investigating the importance of the phenol hydroxyl group, the effect of varying the p-ethylphenyl system, and the substitutions about the pyrazole ring, respectively (FIG. 1) were synthesized.

been reported, including a report detailing a microwave-mediated procedure in acetic acid. the microwave procedure was initially used due to prior successes utilizing a microwave-mediated Pictet-Spengler reaction for the preparation of a previous β-carboline library[13], however, the reported procedure was not reproducible. A number of other reported

TABLE 1

Bioactivity and cytotoxicity of lead pyrazolo[3,4-b]pyridines against *P. falciparum*.

| Compound | $R_1$ | $R_2$ | $EC_{50}$ 3D7[a] (μM) | $EC_{50}$ V1S[b] strain (μM) | $EC_{50}$ BJ[c] (μM) |
|---|---|---|---|---|---|
| 1 (RG-0013862) | H | 4-ethylphenyl | 0.97 ± 0.135 | 0.404 ± 0.102 | >23 |
| 2 | Et | 4-ethylphenyl | >15 | >15 | — |
| 3 | H | 4-methoxyphenyl | 0.461 ± 0.126 | 0.922 ± 0.106 | >23 |
| 4 | H | 3-methoxyphenyl | 0.555 ± 0.213 | 0.834 ± 0.137 | >23 |
| 5 | H | phenyl | 1.19 ± 0.692 | 0.791 ± 0.148 | >23 |

[a]$EC_{50}$ values for the clinically susceptible 3D7 strain are reported as the mean ± SD of five measurements.
[b]$EC_{50}$ values for the multi-drug resistant VIS strain are reported as the mean ± SD of four measuremnts.
[c]Human fibroblast cells.

Example 2: Scheme 1. Synthesis of Pyrazolo[3,4-b]pyridines

A number of one-pot, multicomponent synthetic procedures for the preparation of pyrazolo[3,4-b]pyridines have been reported, including a report detailing a microwave-mediated procedure in acetic acid. procedures were then repeated using benzaldehyde, 2-cyanoacetophenone and 3-methyl-1-phenyl-1H-pyrazol-5-amine as model substrates. Heating the reagents overnight in DMF alone at 100° C. overnight provided the highest conversion as observed by $^1$H NMR. The product could then be isolated in modest yields after purification (Scheme 1).

Scheme 1. Synthesis of pyrazolo[3,4-b]pyridines.

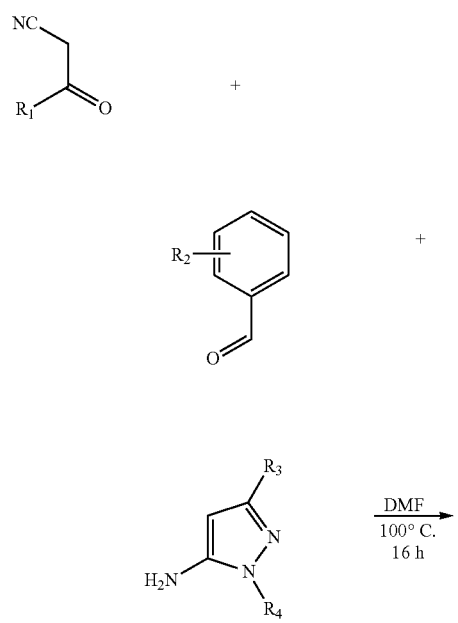

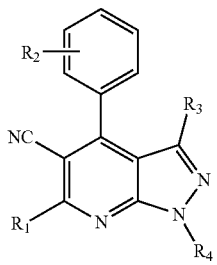

The advantage of this 3-component system was that it allows for easy and selective modification of functional groups in order to prepare the series of modifications outlined in FIG. 1 by selectively varying the appropriate starting reagent, many of which are commercially available.

The first collection of compounds (Series I) was synthesized by varying the aldehyde, as these compounds are commercially available and the final product could be synthesized in a single step. As a positive control, lead compound 1 was also synthesized. After confirming the identity and purity the compounds by NMR and HRMS, the activity of these compounds against the chloroquine sensitive *P. falciparum* 3D7 strain (MRA-102) grown in the presence of O-positive erythrocytes, as well as the cytotoxicity against the human BJ cell line (Table 2) was determined.

TABLE 2

Summary of Series I compounds: antimalarial activity, cytotoxicity, therapeutic index, melting point and solubility.

Series I

| Compound | R | $EC_{50}$ 3D7[a] (μM) | $EC_{50}$ BJ[b] (μM) | T.I. | m.p. (° C.) | Solubility (μM)[c] |
|---|---|---|---|---|---|---|
| 1 | 2-HO-phenyl | 0.397 ± 0.135 | >20 | 50 | 267-269 | 3.1 ± 0.4 |
| 6 | 2-O₂N-phenyl | 0.692 ± 0.056 | >20 | 29 | 225-226 | 1.2 ± 1 |
| 7 | 2-NC-phenyl | 0.427 ± 0.096 | >20 | 47 | 201-203 | 2.4 ± 3 |

TABLE 2-continued
Summary of Series I compounds: antimalarial activity, cytotoxicity, therapeutic index, melting point and solubility.
Series I
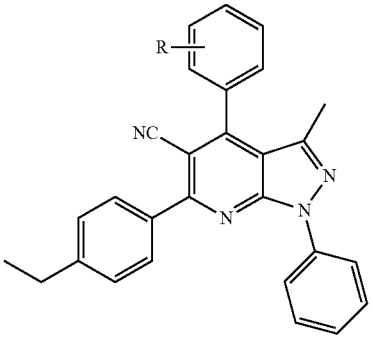
| Compound | R | EC$_{50}$ 3D7$^a$ (μM) | EC$_{50}$ BJ$^b$ (μM) | T.I. | m.p. (° C.) | Solubility (μM)$^c$ |
|---|---|---|---|---|---|---|
| 8 | 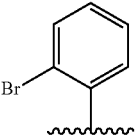 | 0.505 ± 0.067 | >20 | 40 | 205-207 | 8.5 ± 0.9 |
| 9 | 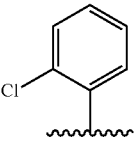 [SMILES: *c1ccccc1Cl] | 0.502 ± 0.104 | >20 | 40 | 208-209 | 1.5 ± 1 |
| 10 |  | 0.363 ± 0.048 | >20 | 55 | 198-199 | 1.7 ± 1 |
| 11 | 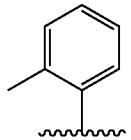 [SMILES: *c1ccccc1C] | 0.783 ± 0.084 | >20 | 26 | 197-199 | 1.7 ± 3 |
| 12 | 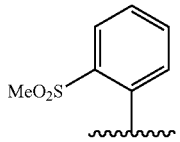 | 0.508 ± 0.124 | >20 | 39 | 203-204 | 6.0 ± 1 |
| 13 | 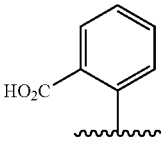 [SMILES: *c1ccccc1C(=O)O] | 0.258 ± 0.047 | >20 | 78 | 196-198 | 2.2 ± 0.9 |
| 14 |  | 1.41 ± 0.359 | >20 | 14 | 198-200 | 33 ± 8 |

TABLE 2-continued

Summary of Series I compounds: antimalarial activity, cytotoxicity, therapeutic index, melting point and solubility.

Series I

| Compound | R | EC$_{50}$ 3D7$^a$ (μM) | EC$_{50}$ BJ$^b$ (μM) | T.I. | m.p. (° C.) | Solubility (μM)$^c$ |
|---|---|---|---|---|---|---|
| 15 | 2-CF$_3$-C$_6$H$_4$ | 0.704 ± 0.232 | >20 | 28 | 193-195 | 11 ± 6 |
| 16 | 2-MeO-C$_6$H$_4$ | 0.554 ± 0.050 | >20 | 36 | 196-198 | 7.8 ± 2 |
| 17 | 2-CF$_3$O-C$_6$H$_4$ | 0.278 ± 0.018 | >20 | 72 | 160-162 | 9.9 ± 4 |
| 18 | C$_6$H$_5$ | 1.79 ± 0.146 | >20 | 11 | 198-199 | 47 ± 20 |
| 19 | 3-HO-C$_6$H$_4$ | 2.04 ± 0.343 | >20 | 10 | 172-174 | 18 ± 3 |
| 20 | 4-HO-C$_6$H$_4$ | 1.80 ± 0.340 | >20 | 11 | 238-240 | 5.7 ± 2 |
| 21 | 2-MeO$_2$C-C$_6$H$_4$ | 0.242 ± 0.016 | >20 | 83 | 141-143 | 17 ± 2 |

TABLE 2-continued

Summary of Series I compounds: antimalarial activity, cytotoxicity, therapeutic index, melting point and solubility.

Series I

[Structure of Series I scaffold shown]

| Compound | R | EC$_{50}$ 3D7[a] (μM) | EC$_{50}$ BJ[b] (μM) | T.I. | m.p. (° C.) | Solubility (μM)[c] |
|---|---|---|---|---|---|---|
| 22 | 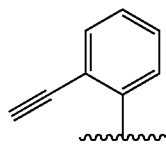 [SMILES: *c1ccccc1C#C] | 1.33 ± 0.330 | >20 | 15 | 148-150 | 46 ± 20 |

[a]EC$_{50}$ values are reported as the mean ± SD of five measurements. Assay endpoints were normalized from 0% (DMSO only) to 100% inhibition (16 μM Mefloquine).
[b]EC$_{50}$ values are reported as the mean ± SD of six measurements. Assay endpoints were normalized from 0% (DMSO only) to 100% inhibition (58 μM Idarubicin).
[c]Solubility in PBS buffer, pH 7.4, with DMSO used as the carrier vehicle. The detection limit of the solubility assay was 100 μM. Albendazole (1.5 ± 1 μM) and carbamazepine (>100 μM) were used as poorly soluble and highly soluble standards, respectively. Values are reported as the mean ± SD of three measurements.

A few derivatives showed some modest improvement in potency, with a chloro (10) and trifluoromethoxy (17) providing an alternative to the hydroxyl group, which would be expected to be metabolically vulnerable. Movement or elimination of the hydroxyl group (18, 19 and 20) had a strongly deleterious effect, as well as replacement of the o-hydroxy with either a carboxylic acid (14) or an ethynyl group (22). Steric hinderance is a possible explanation for this loss of activity, however both a methyl sulfone (13) and a methyl ester (21) displayed activity in a similar range to 1. Most compounds also had fairly high melting points, likely due to extensive pi-pi stacking interactions and the relatively high molecular weights. Solubility values were also on the low side as expected due to the lipophilic nature of most of these compounds.

Example 3: Scheme 2. Synthesis of α-Cyanoketones

The second series of compounds (Series II) were prepared by varying the α-cyanoketone utilized in the reaction. While only a handful of appropriate α-cyanoketones are commercially available, they are readily prepared from widely available methyl ketone derivatives via a two-step procedure consisting of an α-bromination by CuBr$_2$, followed by a nucleophilic substitution with NaCN (Scheme 2). These compounds were then tested against both the *P. falciparum* 3D7 strain and the human BJ cell line (Table 3).

Scheme 2. Synthesis of α-cyanoketones.

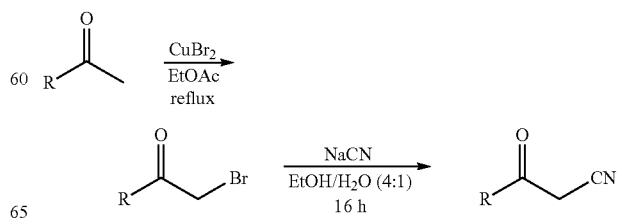

TABLE 3

Summary of Series II compounds: antimalarial activity, cytotoxicity, therapeutic index, melting point and solubility.

Series II

| Compound | R | EC$_{50}$ 3D7$^a$ (μM) | EC$_{50}$ BJ$^b$ (μM) | T.I. | m.p. (° C.) | Solubility (μM)$^c$ |
|---|---|---|---|---|---|---|
| 1 | 4-ethylphenyl | 0.397 ± 0.135 | >20 | 50 | 267-269 | 3.1 ± 0.4 |
| 23 | 4-methylphenyl | 0.384 ± 0.078 | 22.2 ± 2.23 | 58 | 269-270 | 26 ± 0.5 |
| 24 | 3-methylphenyl | 0.283 ± 0.010 | >20 | 71 | 261-262 | 42 ± 6 |
| 25 | 2-methylphenyl | 1.32 ± 0.076 | 21.0 ± 2.51 | 16 | 243-244 | 21 ± 10 |
| 26 | 4-isopropylphenyl | 0.096 ± 0.018 | 22.6 ± 0.351 | 235 | 265-267 | 9.8 ± 1 |
| 27 | 4-tert-butylphenyl | 0.0692 ± 0.016 | 21.3 ± 2.47 | 308 | 219-221 | 9.6 ± 7 |
| 28 | 4-propylphenyl | 0.113 ± 0.024 | 22.5 ± 0.859 | 199 | 240-241 | 6.5 ± 2 |

TABLE 3-continued
Summary of Series II compounds: antimalarial activity, cytotoxicity, therapeutic index, melting point and solubility.
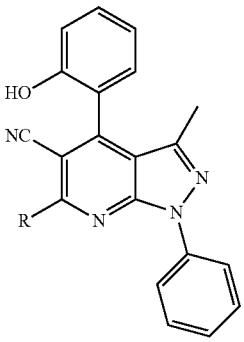
Series II
| Compound | R | EC$_{50}$ 3D7$^a$ (μM) | EC$_{50}$ BJ$^b$ (μM) | T.I. | m.p. (° C.) | Solubility (μM)$^c$ |
|---|---|---|---|---|---|---|
| 29 | 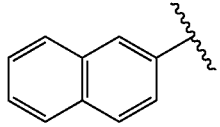 [SMILES: *c1ccc2ccccc2c1] | 0.131 ± 0.029 | >20 | 153 | 241-242 | 1.8 ± 2 |
| 30 | 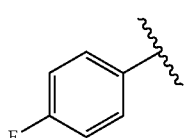 | 0.254 ± 0.032 | 22.9 ± 0.841 | 90 | 254-256 | 3.5 ± 2 |
| 31 | 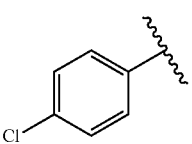 [SMILES: *c1ccc(Cl)cc1] | 0.452 ± 0.167 | >20 | 44 | 234-236 | 6.0 ± 2 |
| 32 | 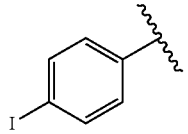 [SMILES: *c1ccc(I)cc1] | 0.247 ± 0.019 | >20 | 81 | 281-282 | 3.8 ± 2 |
| 33 | 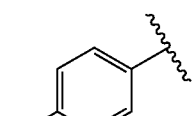 | 0.127 ± 0.008 | 19.0 ± 3.37 | 150 | 289-291 | 1.5 ± 0.4 |
| 34 | 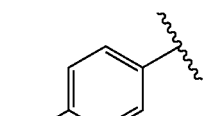 | 0.312 ± 0.036 | >20 | 64 | 165-166 | 1.7 ± 0.2 |
| 35 |  | 0.274 ± 0.019 | >20 | 73 | 257-258 | 6.0 ± 7 |

TABLE 3-continued

Summary of Series II compounds: antimalarial activity, cytotoxicity, therapeutic index, melting point and solubility.

Series II

Core structure: 4-(2-hydroxyphenyl)-5-cyano-3-methyl-1-phenyl-6-R-1H-pyrazolo[3,4-b]pyridine

| Compound | R | EC$_{50}$ 3D7[a] (μM) | EC$_{50}$ BJ[b] (μM) | T.I. | m.p. (°C) | Solubility (μM)[c] |
|---|---|---|---|---|---|---|
| 36 | benzo[1,3]dioxol-5-yl | 0.236 ± 0.050 | 23.0 ± 0.376 | 97 | 240-242 | 11 ± 2 |
| 37 | 4-(methylsulfonyl)phenyl | 0.711 ± 0.094 | >20 | 28 | 222-224 | 5 ± 2 |
| 38 | 5,6,7,8-tetrahydronaphthalen-2-yl | 0.214 ± 0.032 | >20 | 93 | 236-238 | 13 ± 4 |
| 39 | 2,3-dihydrobenzo[1,4]dioxin-6-yl | 0.370 ± 0.058 | >20 | 54 | 293-294 | 11 ± 2 |
| 40 | 3-bromo-4-morpholinophenyl | 0.115 ± 0.011 | >20 | 174 | 268[d] | <1 |
| 41 | 3-ethylphenyl | 0.138 ± 0.034 | >20 | 145 | 178-179 | 11 ± 6 |

[a]EC$_{50}$ values are reported as the mean ± SD of five measurements. Assay endpoints were normalized from 0% (DMSO only) to 100% inhibition (16 μM Mefloquine).
[b]EC$_{50}$ values are reprted as the mean ± SD of six measurements. Assay endpoints were normalized from 0% (DMSO only) to 100% inhibition (58 μM Idarubicin).
[c]Solubility in PBS buffer, pH 7.4, with DMSO used as the carrier vehicle. The detection limit of the solubility assay was 100 μM. Albendazole (1.5 ± 1 μM) and carbamazepine (>100 μM) were used as poorly soluble and highly soluble standards, respectively. Values are reported as the mean ± SD of three measurements.
[d]Decomposes at this temperature.

Most alkyl-substituted phenyl rings (23-28) were tolerated with little effect on observed potency, with a para-tbutylphenyl group displaying the most potent activity and highest therapeutic index (27). A notable exception was observed for 25, where the possible explanation for loss of activity could be the prevention of a planar configuration by the ortho-methyl group, suggesting that a co-planar orientation with the pyrazolo[3,4-b]pyridine is preferred in the binding region. A number of other para-substituted phenyl compounds were investigated (30-35, 37 and 40) and gave no significant change in activity, with the exception of a methyl sulfone (37). Even a para-morpholino phenyl group (40) displayed comparable activity to lead compound 1. Indeed, larger aromatic and heteroaromatic ring systems were also tolerated with negligible change in relative activity (29, 38-39). The wide range of substitutional flexibility makes this substitution point of the pyrazolo[3,4-b]pyridine core an attractive point to modify in future pharmacokinetic studies, both in terms of bioavailability and solubility.

Lastly, a small group of compounds (Series III) was made to investigate some simple substitutions about the pyrazole system, as the original screening set contained no variability about this area of the core scaffold. Only a few pyrazole-5-amines are readily commercially available, but it has been recently reported a rapid microwave-mediated synthesis of various substituted pyrazole-5-amines that affords access to these substrates in a manner of minutes utilizing a simple aqueous workup. Utilizing this methodology, a small number of compounds were prepared which was analyzed as previous substrates (Table 4).

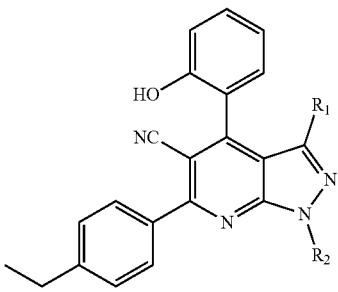

Series III

TABLE 4

Summary of Series III compounds: antimalarial activity, cytotoxicity, therapeutic index, melting point and solubility.

| Compound | $R_1$ | $R_2$ | $EC_{50}$ 3D7[a] (μM) | $EC_{50}$ BJ[b] (μM) | T.I. | m.p. (° C.) | Solubility (μM)[c] |
|---|---|---|---|---|---|---|---|
| 1 | Me | Ph | 0.397 ± 0.135 | >20 | 50 | 267-269 | 3.1 ± 0.4 |
| 42 | Ph | Ph | 0.123 ± 0.025 | >20 | 163 | 248-249 | 30 ± 4 |
| 43 | cyclopropyl | Ph | 0.152 ± 0.041 | >20 | 132 | 122-124 | 21 ± 2 |
| 44 | Me | o-tolyl | 1.04 ± 0.171 | >20 | 19 | 311-313 | 9.6 ± 3 |
| 45 | Me | m-tolyl | 0.094 ± 0.009 | >20 | 213 | 235-237 | 4.8 ± 2 |
| 46 | Me | p-tolyl | 0.139 ± 0.019 | >20 | 144 | 120-122 | 8.9 ± 7 |

[a]$EC_{50}$ values are reported as the mean ± SD of five measurements. Assay endpoints were normalized from 0% (DMSO only) to 100% inhibition (16 μM Mefloquine).
[b]$EC_{50}$ values are reported as the mean ± SD of six measurements. Assay endpoints were normalized from 0% (DMSO only) to 100% inhibition (58 μM Idarubicin).
[c]Solublity in PBS buffer, pH 7.4, with DMSO used as the carrier vehicle. The detection limit of the solubility assay was 100 μM. Albendazole (1.5 ± 1 μm) and carbamazepine (>100 μM) were used as poorly soluble and highly soluble standards, respectively. Values are reported as the mean ± SD of three measurements.

Although only small handful of compounds were prepared, a number of alkyl substitutions were tolerated with the exception of 44, possibly due to either the inability of the phenyl ring to achieve planarity with the pyrazolo[3,4-b]pyridine core or due to steric repulsion. Solubility remains fairly low for these compounds, still likely due to the lipophilic nature of the scaffold. Interestingly, incorporation of a cyclopropyl ring (43) and a para-methyl substitution (46) gave modest potency improvement, along with a significant reduction in the observed melting point and some improvement in the observed solubility.

In total, the in vitro results demonstrate that the ortho-hydroxy group in 1 is required for good potency (Table 1), although some small substitutions to less metabolically sensitive isosteres are tolerated. In contrast, variation of the 2-pyridinyl aryl system (Series II) shows that a large range of substitutions are tolerated without significant changes in observed potency. A few additions to the N-aryl pyrazole system also showed slight improvement (Series III), although it is difficult to draw conclusions from such a small set of derivatives. In general, melting points remain high and solubility low due to the large molecular weight of some derivatives.

Example 4. Efficacy of Selected Compounds Versus Blood States of *Plasmodium*

Three compounds were selected as frontrunner compounds for further efficacy studies. Compound 27 was selected due to the fact that it had the highest observed potency and therapeutic index, while 10 and 17 were selected due to their modest improvement in activity versus the initial lead compound and presented a chloro- and trifluoromethyl-substitution, respectively, in place of the metabolically sensitive ortho-hydroxy group.

Figure 3:
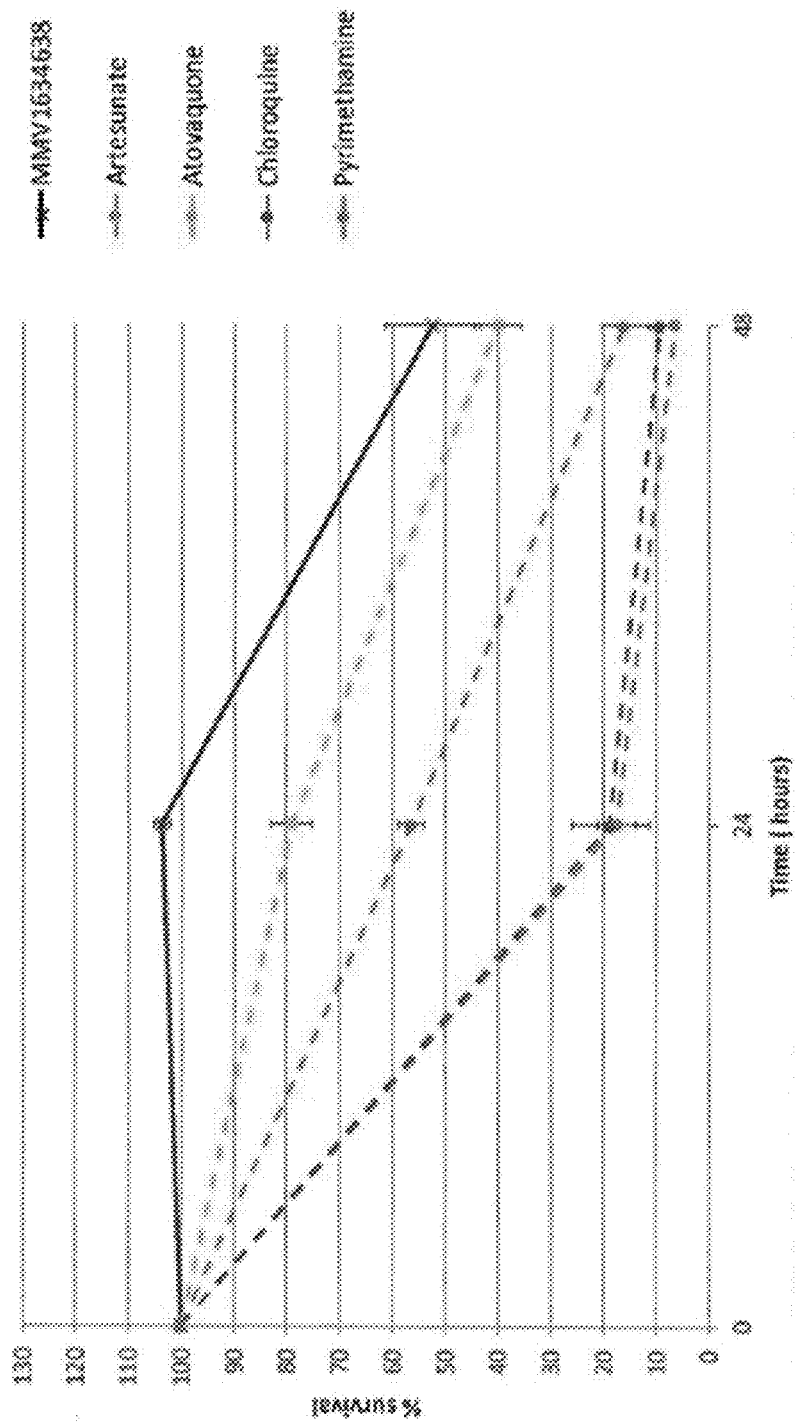
FIG. 3 shows the killing rate profile of compound 10.
Figure 4:
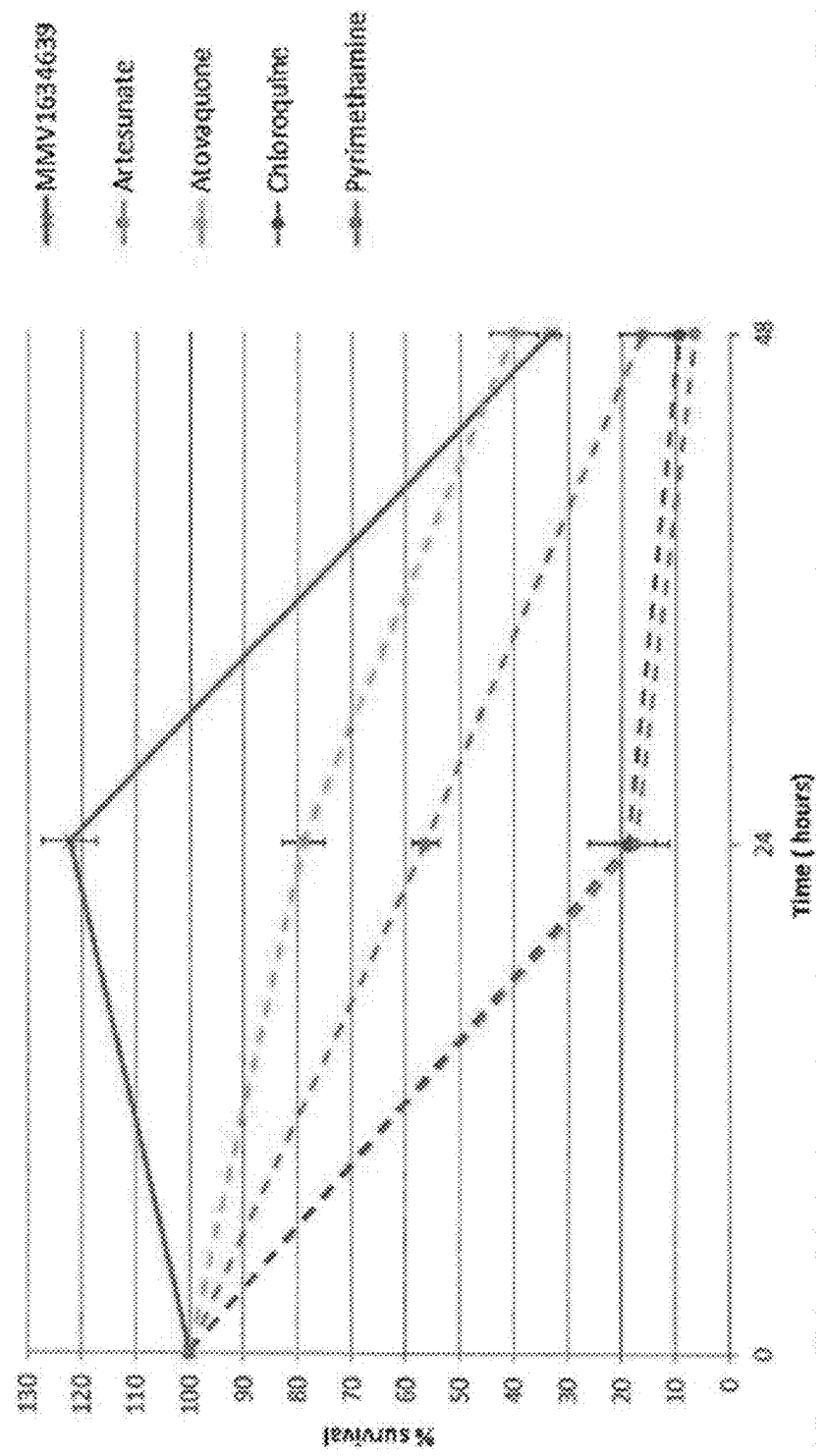
FIG. 4 shows the killing rate profile of compound 17.
Figure 5:
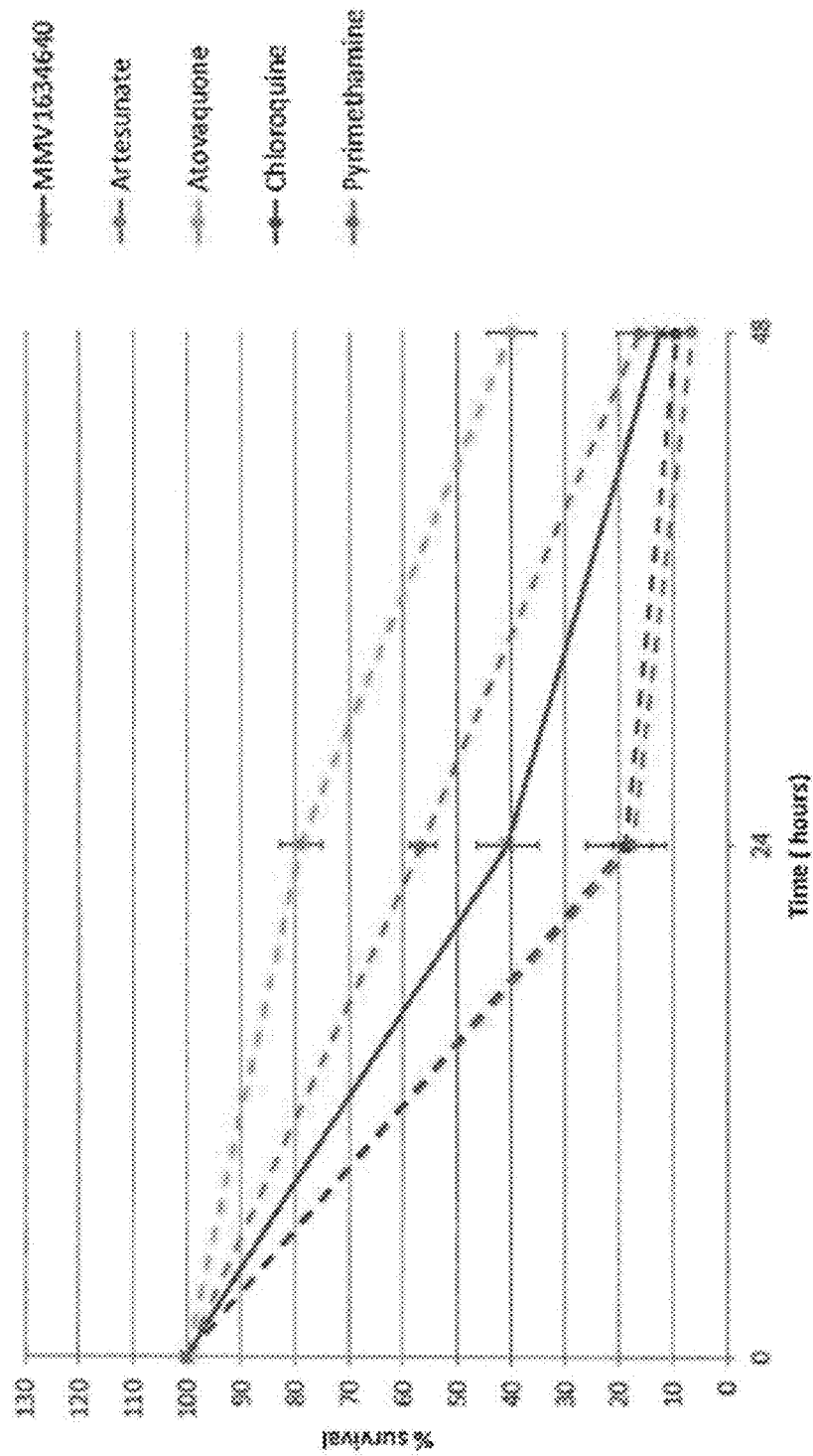
FIG. 5 shows the killing rate profile of compound 27.

In order to determine how quickly the selected frontrunner compounds killed blood stage parasites, a double-colorimetric fluorescence-activated cell sorting (FACS) analysis was used to measure new invasions of pre-stained erythrocytes by drug treated parasites. Two time points (24 h and 48 h) were used to distinguish the rate of killing profile in comparison to chloroquine, pyrimethamine, atovaquone and artesunate, which were used as standard controls (Table 5, FIG. 3). All three compounds presented a moderate to slow killing profile with compounds 10 and 17 displaying a slow killing profile nearly identical to atovaquone, with no inhibition of parasite growth until after 24 h (FIG. 3 and FIG. 4). In contrast, compound 27 displayed a moderate killing profile similar to pyrimethamine (Table 7. FIG. 5).

TABLE 5

Blood stage assays of compounds 10, 17 and 27.

| Cmpd. | Structure | % Survival (24 h)$^a$ | % Survival (48 h)$^a$ | Male Gamete Inhibition$^b$ | Female Gamete Inhibition$^c$ | Gametocyte EC$_{50}$ (μM) |
|---|---|---|---|---|---|---|
| 10 | 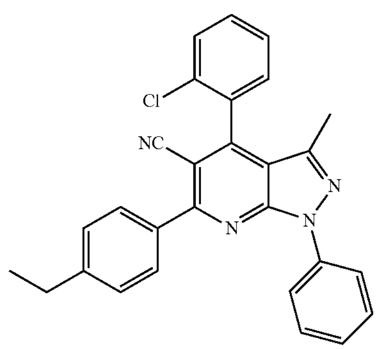 [SMILES: CCc1ccc(-c2nc3c(c(C)nn3-c3ccccc3)c(-c3ccccc3Cl)c2C#N)cc1] | 103.63 ± 1.51% | 52.33 ± 9.07% | 9.61% | 11.55% | >25 |
| 17 | 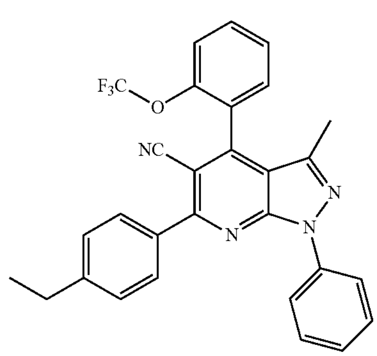 [SMILES: CCc1ccc(-c2nc3c(c(C)nn3-c3ccccc3)c(-c3ccccc3OC(F)(F)F)c2C#N)cc1] | 12.21 ± 5.02% | 32.98 ± 1.55% | 2.69% | −3.94% | >25 |

TABLE 5-continued

Blood stage assays of compounds 10, 17 and 27.

| Cmpd. | Structure | % Survival (24 h)[a] | % Survival (48 h)[a] | Male Gamete Inhibition[b] | Female Gamete Inhibition[c] | Gametocyte $EC_{50}$ (µM) |
|---|---|---|---|---|---|---|
| 27 | 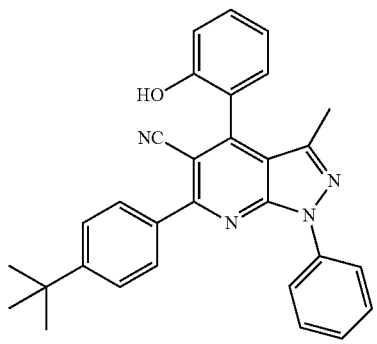 [SMILES: Cc1nn(-c2ccccc2)c2nc(-c3ccc(C(C)(C)C)cc3)c(C#N)c(-c3ccccc3O)c12] | 40.70 ± 5.60% | 12.40 ± 2.37% | 2.48% | −2.29% | >25 |

[a]Values are reported as the mean ± SD of two measurements.
[b]Insert Explanation
[c]Insert Explanation The ability of the selected compounds to inhibit the sexual stages of the parasite were also investigated (Table 5), since transmission is mediated exclusively by the gametocytes of Plasmodium. Moreover, sexually mature stage V gametocytes have shown sex-specific sensitivity to most antimalarial compounds. The three frontrunner compounds were tested at a 1 µM concentration to measure the effect on the growth of both male and female gametocytes, with the results indicating that the compounds are equally ineffective against both. This finding is significant because most clinically approved antimalarials show a marked difference in inhibition against male versus female gametocytes. The only known compound with a similar profile is atovaquone, suggesting that the frontrunner compounds may share a similar mode of action.

TABLE 7

Comparative killing profiles of all compounds versus control compounds.

| | Treatment Time | | |
|---|---|---|---|
| Compound | % Survival at 0 h | % Survival at 24 h | % Survival at 48 h |
| 10 | 100 | 103.63 ± 1.51 | 52.33 ± 9.07 |
| 17 | 100 | 122.21 ± 5.02 | 32.98 ± 1.55 |
| 27 | 100 | 40.70 ± 5.60 | 12.40 ± 2.37 |

TABLE 7-continued

Comparative killing profiles of all compounds versus control compounds.

| | Treatment Time | | |
|---|---|---|---|
| Compound | % Survival at 0 h | % Survival at 24 h | % Survival at 48 h |
| Artesunate | 100 | 17.50 ± 3.68 | 6.44 ± 0.51 |
| Atovaquone | 100 | 78.96 ± 3.89 | 39.89 ± 4.37 |
| Chloroquine | 100 | 18.69 ± 7.34 | 9.21 ± 2.08 |
| Pyrimethamine | 100 | 56.37 ± 2.55 | 16.02 ± 4.36 |

Example 5: Liver Stage Activity of Frontrunner Compounds

Hepatic human transformed cells (HepG2) were pretreated with the frontrunner compounds for 18 hours then were infected with freshly dissected P. berghei Luciferase sporozoites. After 48 hours of incubation, the viability of P. berghei exoerythrocytic forms was measured by bioluminescence. The cytotoxicity of the compounds against HepG2 cells was also determined (Table 6). All three compounds continued to display low cytotoxicity, and compounds 10 and 17 maintained sub-micromolar potency against the liver stage of the parasite.

TABLE 6

*In vivo liver stage assays of compounds 17, 27 and 32.*

| Cmpd. | Structure | P. berghei liver stage $IC_{50}$ in HepG2 cells ($\mu M$)[a] | $EC_{50}$ HepG2 cells ($\mu M$)[a] |
|---|---|---|---|
| 10 | 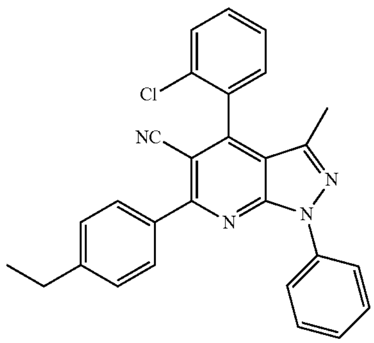 [SMILES: CCc1ccc(-c2nc3c(c(C)nn3-c3ccccc3)c(-c3ccccc3Cl)c2C#N)cc1] | 0.928 ± 0.257 | >50 |
| 17 | 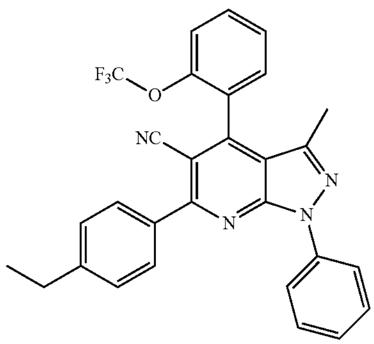 [SMILES: CCc1ccc(-c2nc3c(c(C)nn3-c3ccccc3)c(-c3ccccc3OC(F)(F)F)c2C#N)cc1] | 0.570 ± 0.020 | >25 |
| 27 | 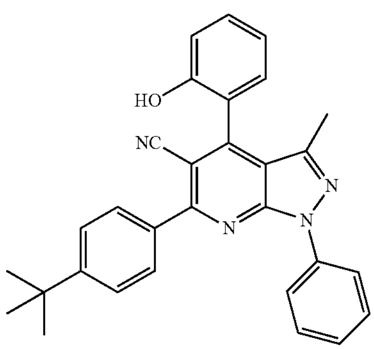 [SMILES: Cc1nn(-c2ccccc2)c2nc(-c3ccc(C(C)(C)C)cc3)c(C#N)c(-c3ccccc3O)c12] | 3.05 ± 0.325 | 24.4 ± 1.06 |

[a]Values are reported as the mean ± SD of two measurements.

It will be understood that various details of the presently disclosed subject matter can be changed without departing from the scope of the subject matter disclosed herein. Furthermore, the foregoing description is for the purpose of illustration only, and not for the purpose of limitation.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. "World Malaria Report 2018" World Health Organization; Geneva, Switzerland. 2018. https://www.who.int/malaria/publications/world-malaria-report-2018/en/
2. Ridley, R. G. "Medical Need, Scientific Opportunity and the Drive for Antimalarial Drugs." Nature, 2002, 415, 686-693.
3. Spangenberg, T.; Burrows, J. N.; Kowalczyk, S.; McDonald, S.; Wells, T. N.; Willis, P. "The Open Access Malaria Box: A Drug Discovery Catalyst for Neglected Diseases." PLoS One, 2013, 8, 62901-62908.
4. (a) Phillips, M. A.; Burrows, J. N.; Manyandoo, C.; van Huijsduijnen, R. H.; van Voorhis, W. C.; Wells, T. N. C. "Malaria." Nat. Rev. Dis. Prim. 2017, 3, 17050. (b) Durrows, J. N.; Burlot, E.; Campo, B.; Cherbuin, S.; Jeanneret, S.; Leroy, D.; Spangenberg, T.; Waterson, D.; Wells, T N. C.; Willis, P. "Antimalarial Drug Discovery—The Path towards Eradication." Parasitology 2014, 141, 128-139. (c) Flannery, E. L.; Chatterjee, A. K.; Winzeler, E. A. "Antimalarial Drug Discovery: Approaches and Progress toward New Medicines." Nat. Rev. Microbiol.

2013, 11, 849-862. (d) Renslo, A. R. "Antimalarial Drug Discovery: From Quinine to the Dream of Eradication." ACS Med. Chem. Lett. 2013, 4, 1126-1128.
5. (a) Njoroge, M.; Njuguna, N. M.; Mutai, P.; Ongarora, D. S. B.; Smith, P. W.; Chibale, K. "Recent Approaches to Chemical Discovery and Development Against Malaria and the Neglected Tropical Diseases Human African Trypanosomiasis and Schistosomiasis." Chem. Rev. 2014, 114, 11138-11163. (b) Crompton, P. D.; Pierce, S. K.; Miller, L. H. "Advances and Challenges in Malaria Vaccine Development." J. Clin. Invest. 2010, 120, 4168-4178. (c) Sauerwein, R. W.; Roestenberg, M.; Moorthy, V. S. "Experimental Human Challenge Infections Can Accelerate Clinical Malaria Vaccine Development." Nat. Rev. Immunool. 2010, 11, 57.
6. Blasco, B.; Leroy, D.; Fidock, D. A. "Antimalarial Drug Resistance: Linking *Plasmodium falciparum* Parasite Biology to the Clinic." Nat. Med. 2017, 3, 17050.
7. (a) Dondorp, A. M.; Nosten, F.; Yi, P.; Das, D.; Phyo, A. P.; Taming, J.; Lwin, K. M.; Ariey, F.; Hanpthakpong, W.; Lee, S. J.; Ringwald, P.; Silamut, K.; Imwong, M.; Chotivanich, K.; Lim, P.; Herdman, T.; An, S. S.; Yeung, S.; Singhasivanon, P.; Day, N. P.; Lindegardh, N.; Socheat, D.; White, N. J. "Artemisinin Resistance in *Plasmodium falciparum* Malaria." N. Engl. J. Med. 2009, 361, 455-467. (b) Haldar, K.; Bhattacharjee, S.; Safekui, I. "Drug Resistance in *Plasmodium*." Nat. Rev. Micro. 2018, 16, 156-170.
8. Gamo, F. J. "Antimalarial Drug Resistance: New Treatment Options for *Plasmodium*." Drug Dis. Today: Technol. 2014, 11, 81-88.
9. Guiguemde, W. A.; Shelat, A. A.; Bouck, D.; Duffy, S.; Crowther, G. J.; Davis, P. H.; Smithson, D. C.; Connelly, M.; Clark, J.; Zhu, F.; Jimenez-Diaz, M. B.; Martinez, M. S.; Wilson, E. B.; Tripathi, A. K.; Gut, J.; Sharlow, E. R.; Bathurst, I.; El Mazouni, F.; Fowble, J. W.; Forquer, I.; McGinley, P. L.; Castro, S.; Angulo-Barturen, I.; Ferrer, S.; Rosenthal, P J.; DeRisi, J. L.; Sullivan, D. J.; Lazo, J. S.; van Voorhis, W. C.; Avery, V. M.; Guy, R. K. "Chemical Genetics of *Plasmodium falciparum*." Nature, 2010, 465, 311-315.
10. (a) Quiroga, J.; Trilleras, J.; Insuasty, B.; Abonia, R.; Nogueras, M.; Cobo, J. "Regioselective Formylation of Pyrazolo[3,4-b]pyridine and Pyrazolo[1,5-a]pyrimidine Systems using Vilsmeier-Haack Conditions." Tet. Lett. 2008, 49, 2689-2691. (b) Hill, M. D.; Fang, H.; Brown, J. M.; Molski, T.; Easton, A.; Han, X.; Miller, R.; Hill-Drzewi, M.; Gallagher, L.; Matchett, M.; Gulianello, M.; Balakrishnan, A.; Bertekap, R. L.; Santone, K. S.; Whiterock, V. J.; Zhuo, X.; Bronson, J. J.; Macor, J. E.; Degnan, A. P. "Development of 1H-Pyrazolo[3,4-b]pyridines as Metabotropic Glutamate Receptor 5 Positive Allosteric Modulators." ACS Med. Chem. Lett. 2016, 7, 1082-1086. (c) Dzvinchuk, I. B. "Synthesis of 5-(1H-Benzimidazol-2-yl)-1H-pyrazolo-[3,4-b]pyridines by the p-(Dimethylamino)benzaldehyde Modification of Hantzsch Reaction." Chem. Heterocycl. Compd. 2007, 43, 474-479. (d) Jachak, M. N.; Avhale, A. B.; Ghotekar, B. K.; Kendre, D. B.; Toche, R. B. "Synthesis of Pyrazole [3,4-b]pyridines Using Ammonium Acetate as Green Reagent in Multi-component Reactions." J Heterocyclic Chem. 2008, 45, 1221-1224. (e) Shi, C.; Shi, D.; Kim, S. H.; Huang, Z.; Ji, S.; Ji, M. "A Novel and Efficient One-Pot Synthesis of Furo[3',4':5,6]pyrido[2,3-c]pyrazole Derivatives Using Organocatalysts." Tetrahedron, 2008, 64, 2425-2432. (f) Patil, S. G.; Bhadke, V. V.; Bagul, R. R. "Synthesis of Pyrazolo[3,4-b]pyridines Using Basic Ionic Liquiz [bmIm]OH." J. Chem. Pharm. Res. 2012, 4, 2751-2754.
11. El-Borai, M. A.; Rizk, H. F.; Abd-Aal, M. F.; El-Deeb, I. Y. "Synthesis of Pyrazolo[3,4-b]pyridines under Microwave Irradiation in Multi-Component Reactions and their Antitumor and Antimicrobial Activities Part 1." Eur. J. Med. Chem. 2012, 48, 92-96.
12. Bayih, A. G.; Folefoc, A.; Mohon, A. N.; Eagon, S.; Anderson, M.; Pillai, D. R. "In Vitro and In Vivo Anti-Malarial Activity of Novel Harmine-Analog Heat Shock Protein 90 Inhibitors: A Possible Partner for Artemisinin." Malar. J. 2016, 15, 579. (b) Eagon, S.; Anderson, M. O. "Microwave-Assisted Synthesis of Tetrahydro-β-carbolines and β-Carbolines." Eur. J. Org. Chem. 2014, 1654-1665.
13. Eagon, S.; Ball-Jones, N.; Haddenham, D. H.; Saavedra, J.; DeLieto, C.; Buckman, M.; Singaram, B. "Enantioselective Reduction of α-Substituted Ketones Mediated by the Boronate Ester TarB-NO2." Tet. Lett. 2010, 51, 6418-6421.
14. Everson, N.; Yniguez, K.; Loop, L.; Lazaro, H.; Belanger, B.; Koch, G.; Bach, J.; Manjunath, A.; Schioldager, R.; Law, J.; Grabenauer, M.; Eagon, S. "Microwave synthesis if 1-Aryl-1H-pyrazole-5-amines." Tet. Lett. 2019, 60, 72-74.
15. Delves, M. J.; Ruecker, A.; Straschil, U.; Lelievre, J.; Marques, S.; Lopez-Barragan, M. J.; Herreros, E.; Sinden, R. E. "Male and Female *Plasmodium falciparum* Mature Gametocytes Show Different Responses to Antimalarial Drugs." Antimicrob. Agents Chemother. 2013, 57, 3268-3274.
16. Trager, W.; Jensen, J. "Human malaria parasites in continuous culture." Science 1976, 193, 673-675.
17. Smilkstein, M.; Sriwilaijaroen, N.; Kelley, J. X.; Wilairat, P., Riscoe, M. "Simple and inexpensive fluorescence-based technique for high-throughput antimalarial drug screening." Antimicrob. Agents Chemother. 2004, 48, 1803-1806.
18. Linares, M.; Viera, S.; Crespo, B.; Franco, V.; Gomez-Lorenzo, M. G.; Jimenez-Diaz, M. B.; Angulo-Barturen, I.; Sanz, L. M.; Gamo, F. J. "Identifying Rapidly Parasiticidal Anti-Malaria Drugs Using a Simple and Reliable in Vitro Parasite Viability Fast Assay." Malar. J. 2015, 14, 441.
19. Bounkeua, V.; Li, F.; Vinetz, J. M. "In Vitro Generation of *Plasmodium falciparum* ookinetes." Am. J. Trop. Med. Hyg. 2010, 83, 1187-1194.
20. Swann, J.; Corey, V.; Scherer, C. A.; Kato, N.; Comer, E.; Maetani, M.; Antonova-Koch, Y.; Reimer, C.; Gagaring, K.; Ibanez, M.; Plouffe, D.; Zeeman, A.; Winzeler, E. A.; Meister, S. "High-Throughput Luciferase-Based Assay for the Discovery of Therapeutics that Prevent Malaria." ACS Infect. Dis. 2016, 2, 281-293.
21. Silvie, O.; Greco, C.; Franetich, J. F.; Dubart-Kupperschmitt, A.; Hannoun, L.; van Gemert, G. J.; Sauerwein, R. W.; Levy, S.; Boucheix, C.; Rubinstein, E.; Mazier, D. "Expression of Human CD81 Differently Affects Host Cell Susceptibility to Malaria Sporozoites Depending on the *Plasmodium* Species." Cell Microbiol. 2006, 8, 1134-1146.
22. Trott, O.; Olson, A. J. "AutoDock Vina: Improving the Speed and Accuracy of Docking with a New Scoring Function, Efficient Optimization, and Multithreading." *J. Comput. Chem.* 2010, 31, 455-461.

23. Li, H.; Leung, K.; Wong, M. "iDock: A Multithreaded Virtual Screening Tool for Flexible Ligand Docking." *CIBCB,* 2015, 34, 115-126.
24. Koes, D. R.; Baumgartner, M. P.; Camacho, C. J. "Lessons Learned in Empirical Scoring with Smina from the CSAR 2011 Benchmarking Exercise." *J. Chem. Inf Model.* 2013, 53, 1893-1904.
25. (a) Zhang, Y.; Clark, J. A.; Connelly, M. C.; Zhu, F.; Min, J.; Guiguemde, W. A.; Pradhan, A.; Iyer, L.; Furimsky, A.; Gow, J.; Parman, T.; El Mazouni, F.; Phillips, M. A.; Kyle, D. E.; Mirsalis, J.; Guy, R. K. "Lead Optimization of 3-Carboxyl-4(1)-Quinolones to Deliver Orally Bioavalable Antimalarials." *J. Med. Chem.* 2012, 55, 4025-4219. (b) Neelarapu, R.; Maignan, J. R.; Lichorowic, C. L.; Monatyrskyi, A.; Mutka, T. S.; LaCrue, A. N.; Blake, L. D.; Casandra, D.; Mashkouri, S.; Burrows, J. N.; Willis, P. A.; Kyle, D. E.; Manetsch, R. "Design and Synthesis of Orally Bioavailable Piperazine Substituted 4(1H)-Quinolones with Potent Antimalarial Activity: Structure-Activity and Structure-Property Relationship Studies." *J. Med. Chem.* 2018, 61, 1450-1473.
26. Capper, M. J.; O'Neill, P. M.; Fisher, N.; Strange, R. W.; Moss, D.; Ward, S. A.; Berry, N. G.; Lawrenson, A. S.; Hasnain, S. S.; Biagini, G. A.; Antonyuk, S. V. "Antimalarial 4(1)-Pyridones Bind to the $Q_i$ Site of Cytochrome $bc_1$." *Proc. Natl. Acad. Sci. U.S.A.,* 2015, 112, 755-760.
27. Barton, V.; Fisher, N.; Baigini, G. A.; Ward, S. A.; O'Neill, P. M. "Inhibiting *Plasmodium* Cytochrome $bc_1$: A Complex Issue." *Curr. Opin. Chem. Biol.* 2010, 14, 440-446.
28. O'Boyle, N. M.; Banck, M.; James, C. A.; Morley, C.; Vandermeersch, T.; Hutchison, G.
R. "Open Babel: An Open Chemical Toolbox." J. Chem. Inform. 2011, 3, 33.
29. Masters, L.; Eagon, S.; Heying, M. Evaluation of consensus scoring methods for AutoDock Vina, smina and idock. J. Mol. Graph. Model. 2020, 96, 107532.
30. Case, D. A.; Ben-Shalom, I. Y.; Brozell, S. R.; Cerutti, D. S.; Cheatham, T. E.; Cruzeiro, V. W. D.; Darden, T. A.; Duke, R. E.; Ghoreishi, D.; Gilson, M. K.; Gohlke, H.; Goetz, A. W.; Greene, D.; Harris, R.; Homeyer, N.; Izadi, S.; Kovalenko, A.; Kurtman, T.; Lee, T. S.; LeGrand, S.; Li, P.; Lin, C.; Liu, J.; Luchko, T.; Luo, R.; Mermelstein, D. J.; Merz, K. M.; Miao,Y.; Monard, G.; Nguyen, C.; Nguyen, H.; Omelyan, I.; Onufriev, A.; Pan, F.; Qi, R.; Roe, D. R.; Roitberg, A.; Sagui, C.; Schott-Verdugo, S.; Shen, J.; Simmerling, C. L.; Smith, J.; Salomon-Ferrer, R.; Swails, J.; Walker, R. C.; Wang, J.; Wei, H.; Wolf, R. M.; Wu, X.; Xiao, L.; York, D. M.; Kollman, P. A. AMBER 2018, University of California, San Francisco.
31. (a) Kollman, P. A.; Massova, I.; Reyes, C.; Kuhn, B.; Huo, S.; Chong L.; Lee, M.; Lee, T.; Duan, Y.; Wang, W.; Donini, O.; Cieplak, P.; Srinivassan, J.; Case, D. A.; Cheatham, T. E. Calculating structures and free energies of complex molecules: combining molecular mechanics and continuum models. Acc. Chem. Res, 2000, 33, 889-897. (b) Genheden, S.; Ryde, U. The MM/PBSA and MM/GBSA methods to estimate ligand-binding affinities. Expert Opin. Drug Dis. 2015, 10, 449-461.
32. Lee, J.; Patel, D. S.; Stihle, J.; Park, S-J.; Kern, N. R.; Kim, S.; Lee, J.; Cheng, X.; Valvano, M. A.; Holst, O.; Knirel, Y.; Qi, Y.; Jo, S.; Klauda, J. B.; Widmalm, G.; Im, W. CHARMM-GUI membrane builder for complex biological membrane simulations with glycolipids and lipoglycans. J. Chem. Theory Comput. 2017, 15, 775-786.
33. Maier, J. A.; Martinez, C.; Kasavajhala, K.; Wickstrom, L.; Hauser, K. E.; Simmerling, C. ff14SB: Improving the accuracy of protein side chain and backbone parameters from ff99SB. J Chem Theory Comput. 2015, 11, 3696-3713.
34. Wang, J.; Wang, W.; Kollman, P. A.; Case, D. A. Development and testing of a general AMBER force field. J. Comput. Chem. 2004, 25, 1157-1174.
35. Jorgensen, W. L.; Chandrasekhar, J.; Madura, J. D.; Impey, R. W.; Klein, M. L. Comparison of simple potential functions for simulating liquid water. J. Chem. Phys. 1983, 79, 926-935.
36. (a) Goetz, A. W.; Williamson, M. J.; Xu, D.; Poole, D.; Le Grand, S.; Walker, R. C. Routine microsecond molecular dynamics simulations with AMBER on GPUs. 1. Generalized Born. J. Chem. Theory Comput. 2012, 8, 1542-1555. (b) Salomon-Ferrer, R.; Goetz, A. W.; Poole, D.; Le Grand, S.; Walker, R. C. Routine microsecond molecular dynamics simulations with AMBER on GPUs. 2. Explicit solvent particle mesh Ewald. J. Chem. Theory Comput. 2013, 9, 3878-3888.
37. Izaguirre, J. A.; Catarello, D. P.; Wozniak, J. M., Skeel, R. D. Langevin stabilization of molecular dynamics. J. Chem. Phys. 2001, 114, 2090-2098. Ryckaert, J. P.; Ciccotti, G.; Berendsen, H. J. C. Numerical integration of the cartesian equations of motion of a system with constraints: molecular dynamics of n-alkanes. J. Comput. Phys. 1977, 23, 327-341.
38. Essmann U.; Perera, L.; Berkowitz, M. L.; Darden, T.; Lee, H.; Pedersen, L. G. A smooth particle mesh Ewald method. J. Chem. Phys. 1995, 103, 8577-8593.
39. Humphrey, W.; Dalke, A.; Schulten, K. VMD: Visual molecular dynamics. J. Mol. Graph. 1996, 14, 27-38

It will be understood that various details of the presently disclosed subject matter can be changed without departing from the scope of the subject matter disclosed herein.

Furthermore, the foregoing description is for the purpose of illustration only, and not for the purpose of limitation.

The invention claimed is:

1. A compound of the following formula:

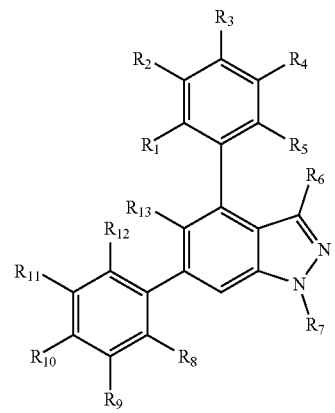

wherein $R_1$-$R_5$ is H, hydroxyl, halo, haloalkyl, alkoxy haloalkoxy, carboxyl, alkoxycarbonyl, lower alkyl, sulfonyl, alkylsulfonyl, amino, imino, nitro, cyano, or alkynyl;

$R_6$ is alkyl, unsubstituted or substituted cycloalkyl, substituted or unsubstituted aryl excluding phenyl, or substituted or unsubstituted heteroaryl;

$R_7$ is alkyl excluding methyl; or $R_7$ is unsubstituted or substituted cycloalkyl, substituted or unsubstituted aryl, or substituted or unsubstituted heteroaryl;

R$_8$-R$_{12}$ is H, OH, alkyl, alkoxy, halo, haloalkyl, alkoxy, branched or unbranched alkyl, haloalkyl, halo, cyano, nitro, sulfonyl, alkylsulfonyl, or heterocycloalkyl;
R$_{13}$ is cyano, nitro, imino, or alkynyl; and
R$_{10}$ may optionally form a 5 or 6 membered substituted or unsubstituted heterocycle with R$_{11}$.

2. The compound of claim 1 of the following formula:

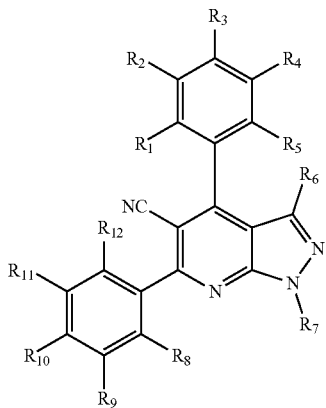

wherein R$_1$-R$_5$ is H, hydroxyl, halo, haloalkyl, alkoxy haloalkoxy, carboxyl, alkoxycarbonyl, lower alkyl, sulfonyl, alkylsulfonyl, amino, imino, nitro, cyano, or alkynyl;
R$_6$ is alkyl, unsubstituted or substituted cycloalkyl, substituted or unsubstituted aryl excluding phenyl, or substituted or unsubstituted heteroaryl;
R$_7$ is alkyl excluding methyl; or R$_7$ is unsubstituted or substituted cycloalkyl, substituted or unsubstituted aryl, or substituted or unsubstituted heteroaryl;
R$_8$-R$_{12}$ is H, OH, alkyl, alkoxy, halo, haloalkyl, alkoxy, branched or unbranched alkyl, haloalkyl, halo, cyano, nitro, sulfonyl, alkylsulfonyl, or heterocycloalkyl; and
R$_{10}$ may optionally form a 5 or 6 membered substituted or unsubstituted heterocycle with R$_{11}$.

3. The compound of claim 2, wherein
R$_1$-R$_5$ is H, hydroxyl, halo, haloalkyl, alkoxy haloalkoxy, carboxyl, alkoxycarbonyl, lower alkyl, sulfonyl, alkylsulfonyl, amino, imino, nitro, cyano, or alkynyl;
R$_6$ is methyl;
R$_7$ is phenyl;
R$_8$-R$_9$ is H;
R$_{10}$ is lower alkyl; and
R$_{11}$-R$_{12}$ is H.

4. The compound of claim 3 selected from:

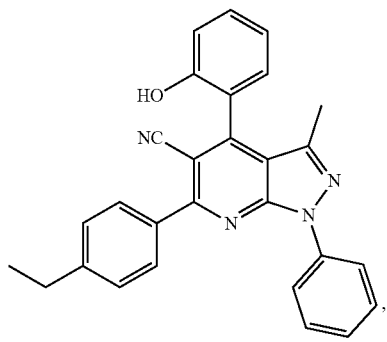

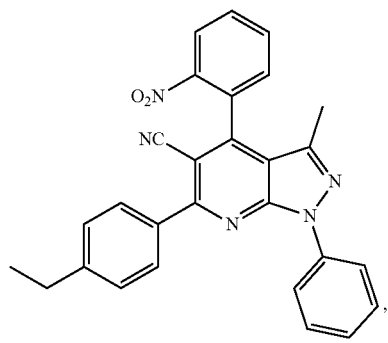

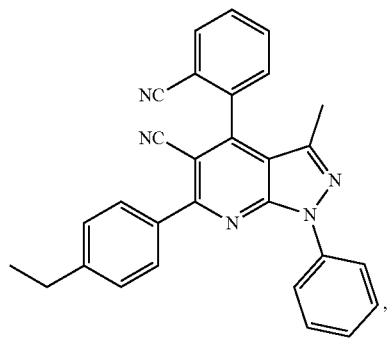

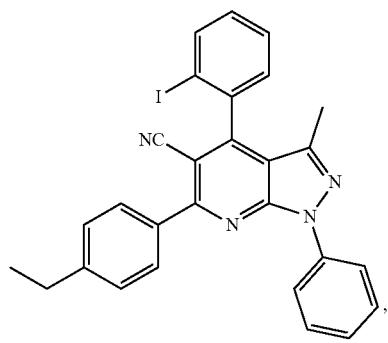

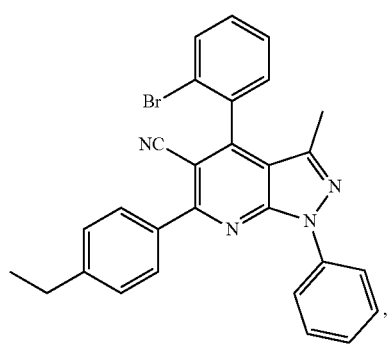

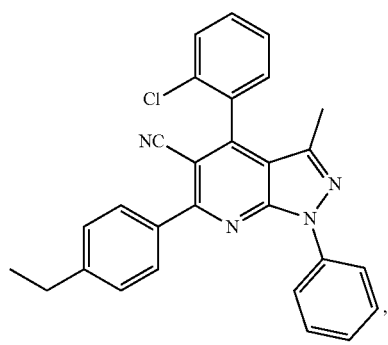

99
-continued
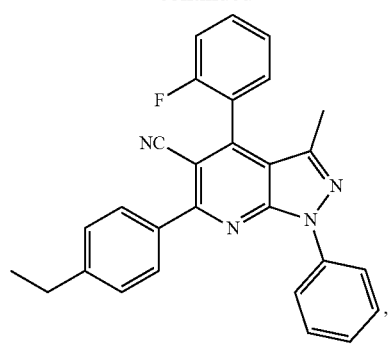
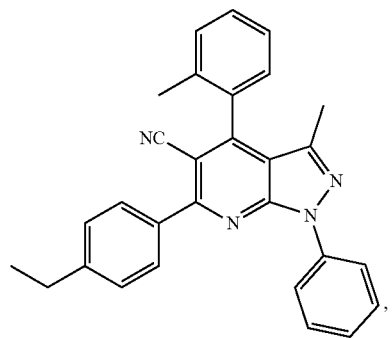
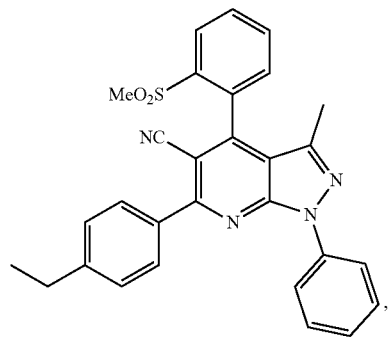
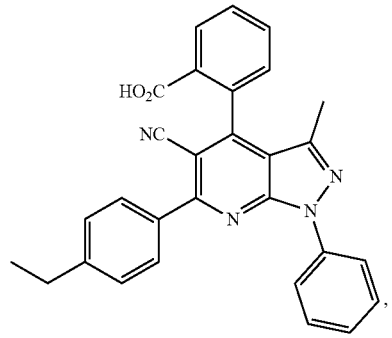
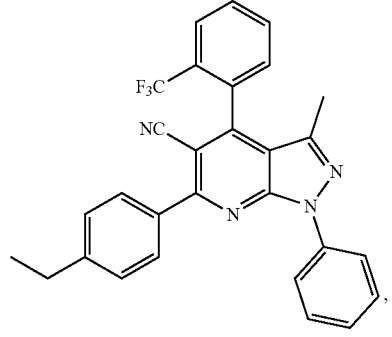
100
-continued
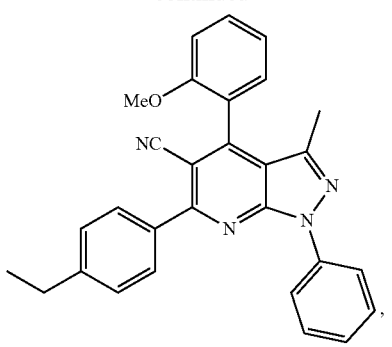
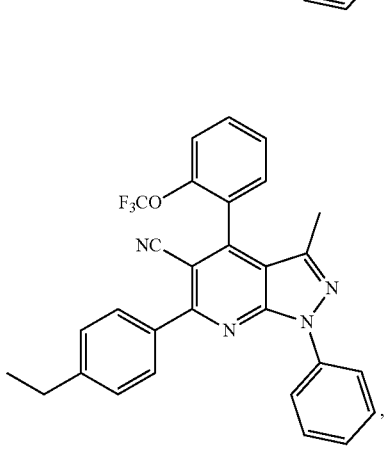
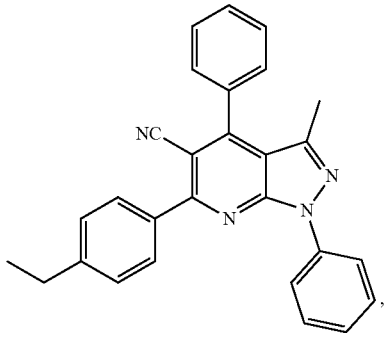
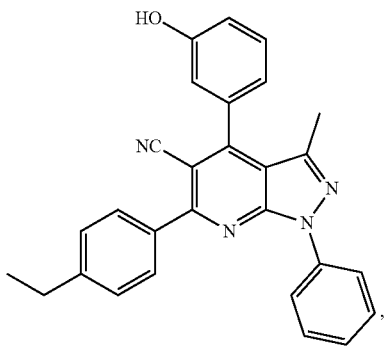

-continued

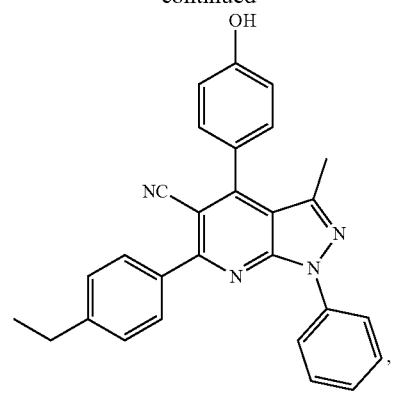

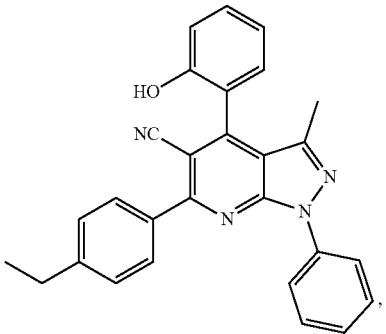

, and

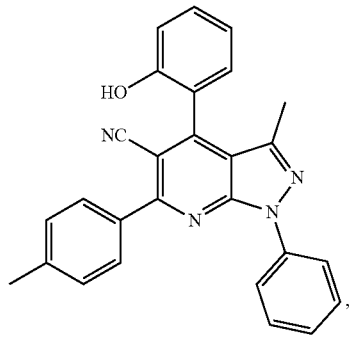

.

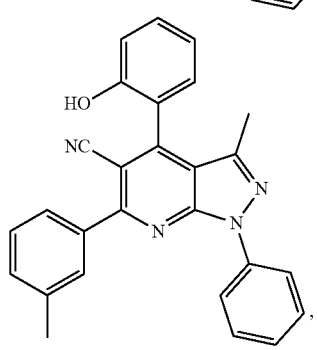

5. The compound of claim 2, wherein $R_1$ is OH;

$R_2$-$R_5$ is H;

$R_6$ is lower alkyl;

$R_7$ is phenyl;

$R_8$-$R_{12}$ is H, OH, alkyl, alkoxy, halo, haloalkyl, alkoxy, branched or unbranched alkyl, haloalkyl, halo, cyano, nitro, sulfonyl, alkylsulfonyl, or heterocycloalkyl; and $R_{10}$ may optionally form a 5 or 6 membered substituted or unsubstituted heterocycle with $R_{11}$.

6. The compound of claim 5, selected from

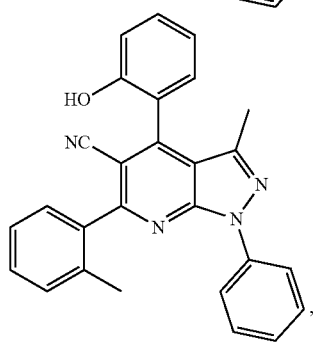

,

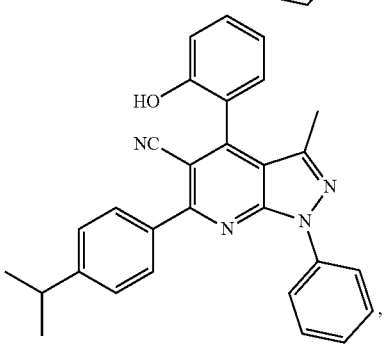

,

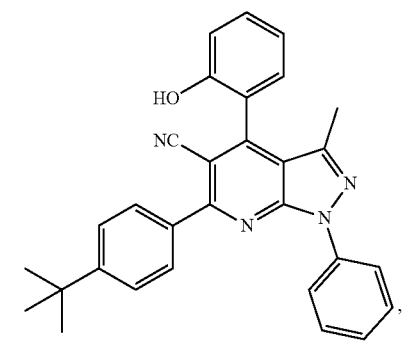
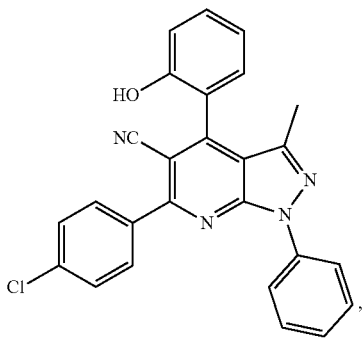
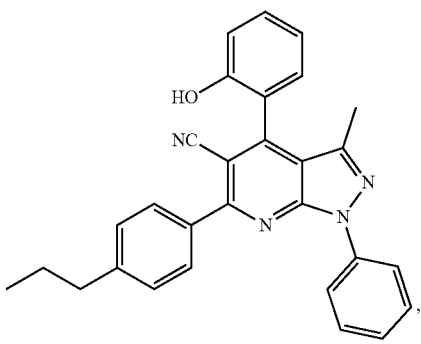
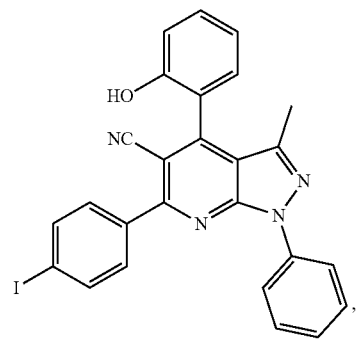
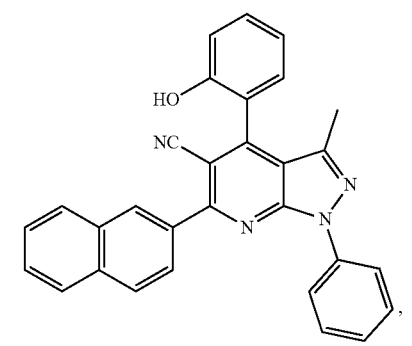
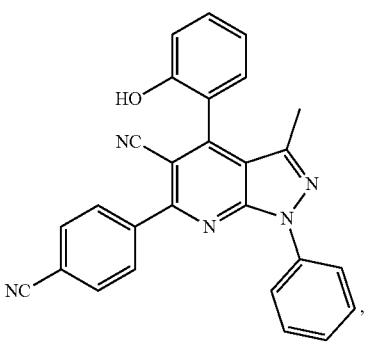
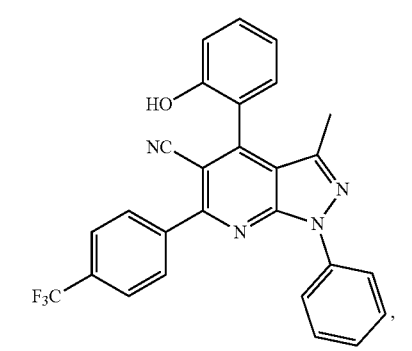
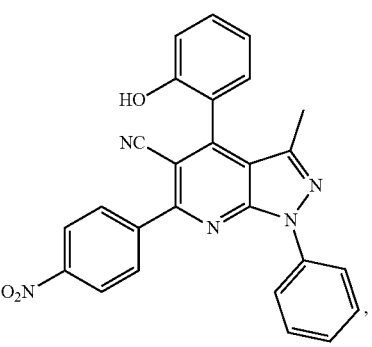
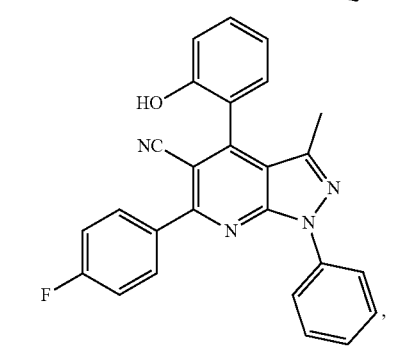
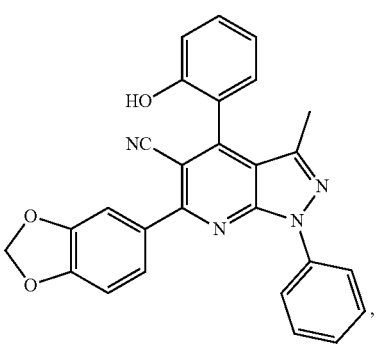

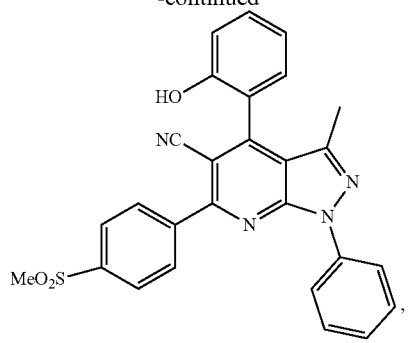

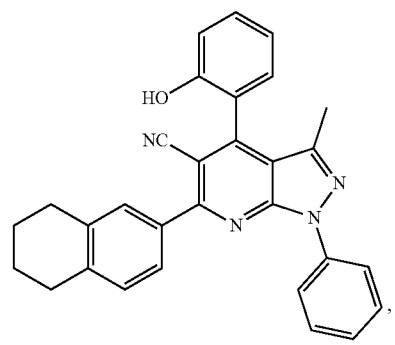

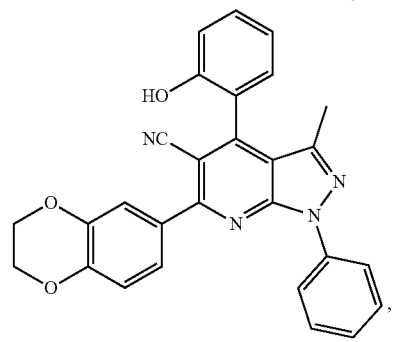

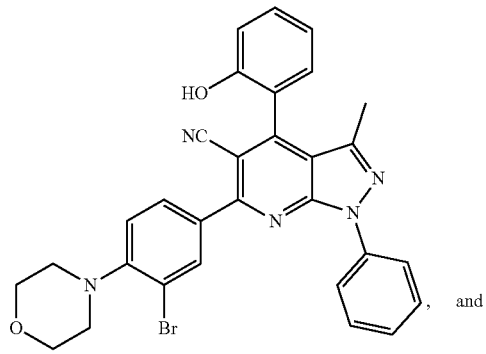, and

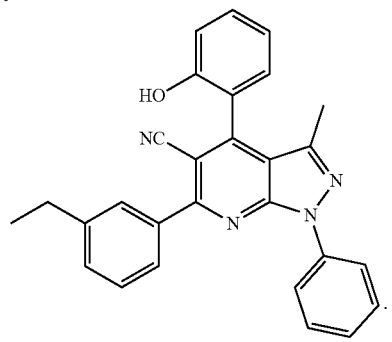.

7. The compound of claim 2, wherein
$R_1$ is OH;
$R_2$-$R_5$ is H;
$R_6$ is alkyl, unsubstituted or substituted cycloalkyl, substituted or unsubstituted aryl excluding phenyl, or substituted or unsubstituted heteroaryl;
$R_7$ is alkyl excluding methyl; or $R_7$ is unsubstituted or substituted cycloalkyl, substituted or unsubstituted aryl, or substituted or unsubstituted heteroaryl;
$R_8$-$R_9$ is H;
$R_{10}$ is lower alkyl; and
$R_{11}$-$R_{12}$ is H.

8. The compound of claim 7 selected from:

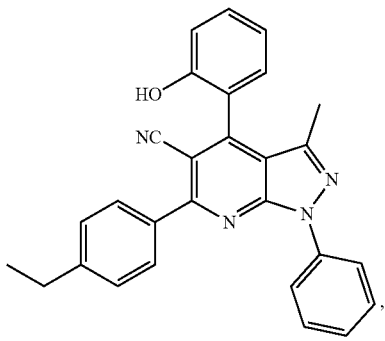

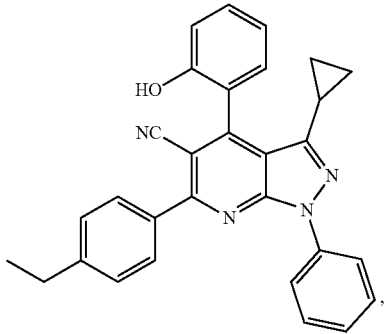

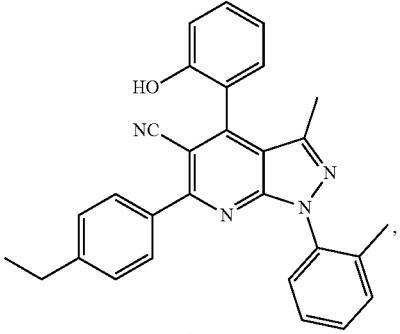

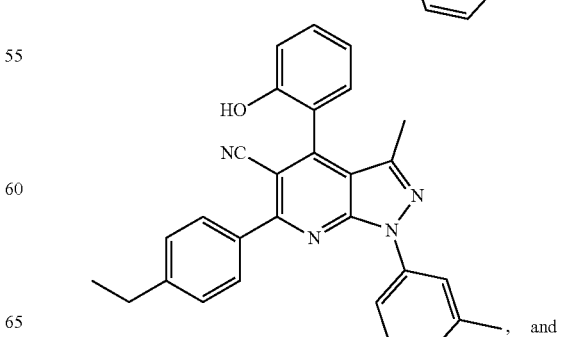, and

-continued

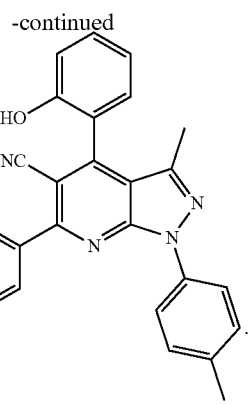

9. A pharmaceutical composition, comprising a compound of the following formula:

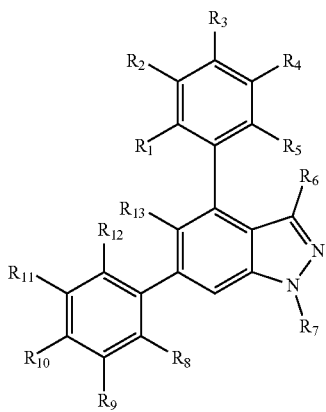

wherein $R_1$-$R_5$ is H, hydroxyl, halo, haloalkyl, alkoxy haloalkoxy, carboxyl, alkoxycarbonyl, lower alkyl, sulfonyl, alkylsulfonyl, amino, imino, nitro, cyano, or alkynyl;

$R_6$ is alkyl, unsubstituted or substituted cycloalkyl, substituted or unsubstituted aryl excluding phenyl, or substituted or unsubstituted heteroaryl;

$R_7$ is alkyl excluding methyl; or $R_7$ is unsubstituted or substituted cycloalkyl, substituted or unsubstituted aryl, or substituted or unsubstituted heteroaryl;

$R_8$-$R_{12}$ is H, OH, alkyl, alkoxy, halo, haloalkyl, alkoxy, branched or unbranched alkyl, haloalkyl, halo, cyano, nitro, sulfonyl, alkylsulfonyl, or heterocycloalkyl;

$R_{13}$ is cyano, nitro, imino, or alkynyl; and $R_{10}$ may optionally form a 5 or 6 membered substituted or unsubstituted heterocycle with $R_{11}$; and a pharmaceutically acceptable carrier.

10. A method for inhibiting the growth of *Plasmodium* comprising administering to cells infected with *Plasmodium* the compound of claim 1.

11. The method of claim 10, wherein the *Plasmodium* is *Plasmodium falciparum*.

12. The method of claim 10, wherein the *Plasmodium* is drug resistant.

13. The method of claim 12, wherein the *Plasmodium* is atovaquone-resistant.

14. The method of claim 10, wherein the cells are in a subject.

15. The method of claim 14, wherein the subject is a human.

* * * * *